(12) United States Patent
Jiang

(10) Patent No.: US 9,856,239 B1
(45) Date of Patent: *Jan. 2, 2018

(54) CARBOXYLIC ACID COMPOUND, METHOD FOR PREPARATION THEREOF, AND USE THEREOF

(71) Applicant: INVENTISBIO SHANGHAI LTD., Shanghai (CN)

(72) Inventor: Yueheng Jiang, Shanghai (CN)

(73) Assignee: InventisBio Shanghai Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/723,785

(22) Filed: Oct. 3, 2017

Related U.S. Application Data

(63) Continuation of application No. 15/501,387, filed as application No. PCT/CN2015/086605 on Aug. 11, 2015, now Pat. No. 9,809,580.

(30) Foreign Application Priority Data

Aug. 13, 2014 (CN) .......................... 2014 1 0398333

(51) Int. Cl.
| | | |
|---|---|---|
| C07D 405/10 | (2006.01) | |
| C07D 213/68 | (2006.01) | |
| C07D 401/04 | (2006.01) | |
| C07D 213/57 | (2006.01) | |
| C07D 213/74 | (2006.01) | |
| C07D 213/70 | (2006.01) | |
| C07B 59/00 | (2006.01) | |
| C07C 323/63 | (2006.01) | |

(52) U.S. Cl.
CPC .......... *C07D 405/10* (2013.01); *C07B 59/002* (2013.01); *C07C 323/63* (2013.01); *C07D 213/57* (2013.01); *C07D 213/68* (2013.01); *C07D 213/70* (2013.01); *C07D 213/74* (2013.01); *C07D 401/04* (2013.01); *C07B 2200/05* (2013.01); *C07C 2601/02* (2017.05)

(58) Field of Classification Search
None
See application file for complete search history.

(56) References Cited

U.S. PATENT DOCUMENTS

2017/0233376 A1* 8/2017 Jiang ..................... C07D 405/10
514/307

FOREIGN PATENT DOCUMENTS

| CN | 1791572 A | 6/2006 |
|---|---|---|
| CN | 103068801 A | 4/2013 |
| WO | WO 2004/089885 A1 | 10/2004 |
| WO | WO 2011/159839 A2 | 12/2011 |

OTHER PUBLICATIONS

Zhou, B. et al., "Amine-accelerated Manganese-Catalyzed Aromatic C—H Conjugate Addition to α, β-unsaturated Carbonyls," Chemical Communications, 50:14558-14561 (2014), The Royal Society of Chemistry, United Kingdom.
Du, J. et al., "Rhodium-Catalyzed Direct Amination of Arenes with Nitrosobenzenes: A New Route to Diarylamines," Chemistry, a European Journal, 20:1-6 (2014) Wiley-VCH, Germany.
Guino, M. et al., "Silicaethylphosphatrioxaadamantane—A New Support for Palladium Catalysts and Evaluation in Suzuki Coupling Reactions," Journal of Molecular Catalysis A: Chemical, 293(1-2) 25-30 (2008), Elsevier, Netherands.
English translation of International Search Report of PCT/CN2015/086605 dated Nov. 24, 2015, WIPO, China.
Silverman, R.B. et al., "The Organic Chemistry of Drug and Drug Action", Academic Press, pp. 352-355 (1992), Elsevier, Netherlands.

* cited by examiner

*Primary Examiner* — Karl J Puttlitz
(74) *Attorney, Agent, or Firm* — Rubin and Rudman LLP; Xiaoxiang Liu

(57) ABSTRACT

The present invention relates to the technical field of medicine, and specifically relates to the carboxylic acid compound represented by the chemical formula I or chemical formula II, and a pharmaceutically acceptable salt, a prodrug, and a solvate thereof, and a method for preparation thereof, as well as a pharmaceutical composition containing the described substances, and a use thereof.

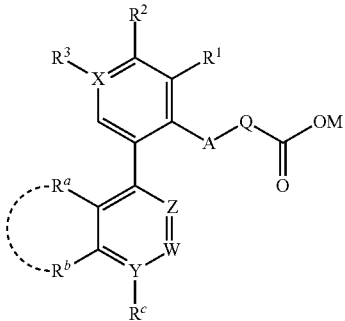

[Chemical Formula I]

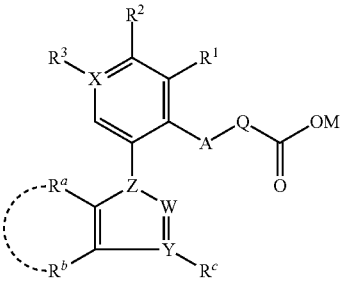

[Chemical Formula II]

23 Claims, No Drawings

CARBOXYLIC ACID COMPOUND, METHOD FOR PREPARATION THEREOF, AND USE THEREOF

TECHNICAL FIELD

The invention relates to pharmaceutical technical field, specifically, to carboxylic acid compounds and pharmaceutically acceptable salts, prodrugs, and solvates thereof and preparation methods thereof, and to pharmaceutical compositions comprising the same and uses thereof.

BACKGROUND TECHNIQUE

Uric acid is the final metabolite of diet and purine in human body. In vivo environment (pH 7.4, 37 degrees), uric acid is present in blood mainly in the form of sodium salt of uric acid, the serum uric acid value of normal people is generally lower than 6 mg/dL. When uric acid in serum exceeds 7 mg/dL (Shi, et al., Nature 2003, 425: 516-523), sodium salt of uric acid will crystallize out and precipitate on joints and other parts of the body, and result in disorders such as gout, urinary stones, kidney stones, etc. Patients with gout are often accompanied with other complications, including hypertension, diabetes, hyperlipidemia, dyslipidemia, atherosclerosis, obesity, metabolic disease, nephropathy, cardiovascular disease, and respiratory disease, etc. (Rock, Et al., Nature Reviews Rheumatology 2013, 9: 13-23). In 2002, Japanese scientists Endou group reported that anion transport channel protein URAT1 is a major protein responsible for reabsorption of uric acid in kidney, they also found that the blood uric acid in people with URAT1 gene mutation (causing the synthesis of such protein being interrupted, inducing nonfunctional proteins) is only one-tenth of that in normal people (Enomoto et. al., Nature 2002 417: 447-452). These findings in human genetics demonstrate that URAT1 anion transport protein in kidney plays very important role in concentration of uric acid in blood, and indicates that URAT1 is a very good and specific target of a drug for reducing blood uric acid.

The main objective in the treatment of gout and its complications caused by higher level of blood uric acid is to reduce blood uric acid to lower than 6 mg/dL, the main methods are as follows: 1) to inhibit the generation of uric acid, such as allopurinol, febuxostat, which are drugs for inhibiting Xanthine oxidase; 2) to inhibit the reabsorption of uric acid, such as benzbromarone and probenecid, and lesinurad which is currently in clinical research, all of which are drugs for inhibiting kidney URAT1 anion transport channel protein.

In addition to URAT1, there are other cation transport channel proteins in kidney, such as Glut9 and OAT1 etc., which are also found to be able to reabsorb uric acid back to blood from renal tubules. Kidney is a major excretion pathway of uric acid in human body (70%), intestinal system (via ABCG2 etc.,) is responsible for excreting approximate 30% of uric acid (Sakurai, et. al., Current Opinion in Nephology and Hypertension 2013, 22: 545-550).

Human urate anion transporter 1, hURAT1, a member of anion transporter family, is located at luminal surface side of epithelial cells of renal proximal convoluted tubules, mainly participates in the reabsorption of uric acid in renal proximal convoluted tubules. URAT1 accomplishes reabsorption of uric acid and excretion of small amount of uric acid by exchanging univalent anions within cells with uric acid in lumens. Anion transport channel proteins located in renal proximal convoluted tubules also comprise anion transport channel protein OAT4, which has 42% of similarity with URAT1 (amino acids of protein). Therefore, generally, a potent URAT1 inhibitor will also inhibit OAT4 and some other anion transport channel proteins.

At present, all the clinical drugs for reducing blood uric acid have some side effects, for example, allopurinol will cause life-threatening hypersensitivity in some populations, febuxostat has cardiovascular side effects, and benzbromarone has liver toxicity and has been taken back by Sanofi from some markets. Therefore, it is urgent to search for novel, efficient and low-toxic drugs for reducing blood uric acid, and this will have great clinical significance and application prospects.

Thioacetate compounds have been reported in the prior art, e.g., a class of phenylthioacetate compounds were reported in CN102939279A, a class of thioacetate compounds were reported in CN103068801A, wherein thioacetate compounds in CN103068801A are obtained from the compounds in CN102939279A by essentially replacing carbons of benzene groups in skeletons of the compounds in CN102939279A with 1 to 4 N atoms.

Since categories of drugs for gout treatment are very limited in market, it is important to develop anti-gout drugs with high efficiency and low toxicity.

CONTENTS OF THE INVENTION

According to one aspect of the present invention, one objective of the present invention is to design and synthesize a carboxylic acid compound, and pharmaceutically acceptable salts, prodrugs, and solvates thereof.

According to another aspect of the present invention, another objective of the present invention is to provide a preparation method of the carboxylic acid compound, and pharmaceutically acceptable salts, prodrugs, and solvates thereof.

According to another aspect of the present invention, another objective of the present invention is to provide a use of the carboxylic acid compound, and pharmaceutically acceptable salts, prodrugs, and solvates thereof in the preparation of a drug for promoting the excretion of uric acid with URAT1 as a target.

According to another aspect of the present invention, another objective of the present invention is to provide a pharmaceutical composition comprising one or more selected from the carboxylic acid compound, and pharmaceutically acceptable salts, prodrugs, and solvates thereof.

The carboxylic acid compound according to the present invention is represented by the following Chemical Formula I:

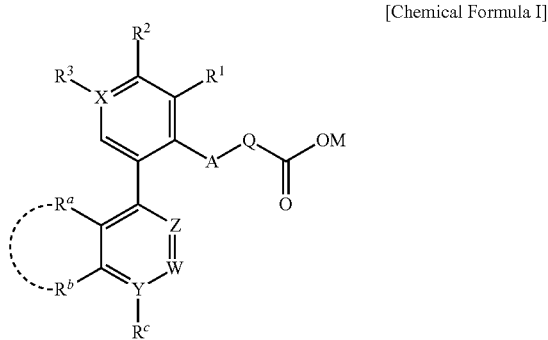

[Chemical Formula I]

Wherein,

X is C or N;

Y, W and Z are each independently C or N;

A is S, N, SO$_2$, O or absent;

Q is substituted or unsubstituted C1-6 straight-chain or branched-chain alkylene, substituted or unsubstituted C3-6 cycloalkylene, substituted or unsubstituted C6-12 arylene, wherein substituent is —CD$_3$, C1-6 alkyl, C3-6 cycloalkyl, C3-6 cycloalkylene or halogen;

M is H, Na, K, Ca or C1-4 alkyl;

R$^1$, R$^2$ and R$^3$ are each independently hydrogen, halogen or absent;

R$^a$ and R$^b$ are each independently hydrogen, C1-6 alkyl or bond to each other to form a substituted or unsubstituted C6-10 aromatic ring structure, wherein the substituent in the substituted C6-10 aromatic ring structure is halogen, C1-3 alkyl or C1-3 alkoxy;

R$^c$ is —CN, carboxyl, hydroxyl-substituted or unsubstituted C1-6 alkyl, hydroxyl-substituted or unsubstituted C3-6 cycloalkyl, hydroxyl-substituted or unsubstituted 3- to 6-membered heterocycloalkyl containing 1 to 3 heteroatoms selected from O, S and N.

Preferably,

X is C or N;

Y, W and Z are each independently C or N;

A is S, N, SO$_2$, O or absent;

Q is substituted or unsubstituted C1-3 straight-chain or branched-chain alkylene, substituted or unsubstituted C3-5 cycloalkylene, phenyl, wherein substituent is —CD$_3$, C1-3 alkyl, C3-5 cycloalkyl, C3-5 cycloalkylene or halogen selected from fluorine, chlorine, bromine and iodine;

M is H, Na, K, Ca or C1-4 alkyl;

R$^1$, R$^2$ and R$^3$ are each independently hydrogen, halogen or absent;

R$^a$ and R$^b$ are each independently hydrogen, C1-3 alkyl or bond to each other to form a substituted or unsubstituted benzene ring structure, wherein the substituent in the substituted benzene ring structure is halogen, C1-3 alkyl or C1-3 alkoxy;

R$^c$ is —CN, carboxyl, hydroxyl-substituted or unsubstituted C1-3 alkyl, hydroxyl-substituted or unsubstituted C3-5 cycloalkyl, hydroxyl-substituted or unsubstituted 3- to 5-membered heterocycloalkyl containing 1 to 3 heteroatoms selected from O, S and N.

More preferably,

X is C or N;

Y, W and Z are each independently C or N;

A is S, N, SO$_2$, O or absent;

Q is substituted or unsubstituted C1-3 straight-chain or branched-chain alkylene,

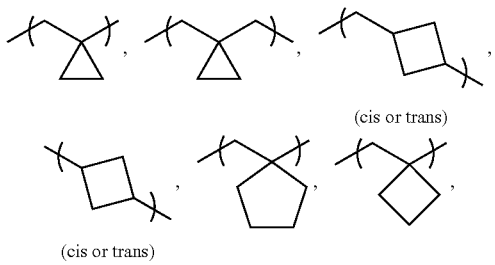

(cis or trans)

phenyl, wherein substituent is methyl, ethyl, propyl, —CD$_3$, C3-5 cycloalkyl, C3-5 cycloalkylene or fluorine;

M is H;

R$^1$, R$^2$ and R$^3$ are each independently hydrogen, halogen or absent;

R$^a$ and R$^b$ are each independently hydrogen, or bond to each other to form a benzene ring;

R$^c$ is —CN, carboxyl, methyl, ethyl, propyl, hydroxymethyl, hydroxyethyl, hydroxypropyl, cyclopropyl, cyclobutyl, hydroxyl-substituted cyclopropyl, hydroxyl-substituted cyclobutyl, oxiranyl, oxetanyl, hydroxyl-substituted oxiranyl or hydroxyl-substituted oxetanyl.

Further preferably,

X is C or N;

Y, W and Z are each independently C or N;

A is S;

Q is substituted or unsubstituted ethylene, propylene, isopropylidene,

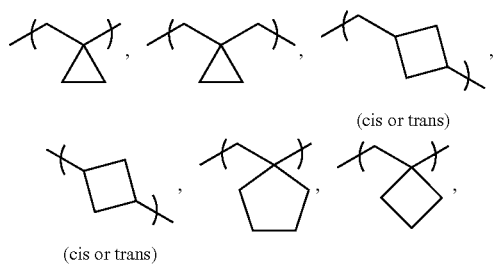

(cis or trans)

phenyl, wherein substituent is methyl, ethyl, propyl, —CD$_3$, cyclopropyl, cyclobutyl, cyclopentyl, cyclopropylidene, cyclobutylidene, cyclopentylidene or fluorine;

M is H;

R$^1$, R$^2$ and R$^3$ are each independently hydrogen, halogen or absent;

R$^a$ and R$^b$ are each independently hydrogen, or bond to each other to form a benzene ring;

R$^c$ is —CN, carboxyl, methyl, ethyl, propyl, hydroxymethyl, hydroxyethyl, hydroxypropyl, cyclopropyl, cyclobutyl, hydroxyl-substituted cyclopropyl, hydroxyl-substituted cyclobutyl, oxiranyl, oxetanyl, hydroxyl-substituted oxiranyl or hydroxyl-substituted oxetanyl.

In one embodiment, the carboxylic acid compound according to the present invention is represented by the following chemical formula II:

[Chemical Formula II]

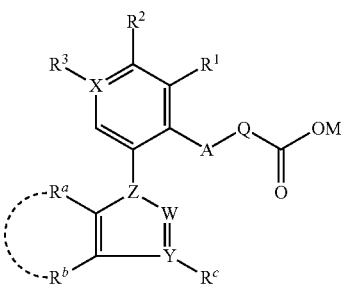

Wherein,

X is C or N;

Y, W and Z are each independently C or N;

A is S, N, SO$_2$, O or absent;

Q is substituted or unsubstituted C1-6 straight-chain or branched-chain alkylene, substituted or unsubstituted C3-6 cycloalkylene, substituted or unsubstituted C6-12 arylene, wherein substituent is —CD$_3$, C1-6 alkyl, C3-6 cycloalkyl, C3-6 cycloalkylene or halogen;

M is H, Na, K, Ca or C1-4 alkyl;

R$^1$, R$^2$ and R$^3$ are each independently hydrogen, halogen or absent;

R$^a$ and R$^b$ are each independently hydrogen, C1-6 alkyl or bond to each other to form a substituted or unsubstituted C6-10 aromatic ring structure, wherein the substituent in the substituted C6-10 aromatic ring structure is halogen, C1-3 alkyl or C1-3 alkoxy;

R$^c$ is —CN, carboxyl, hydroxyl-substituted or unsubstituted C1-6 alkyl, hydroxyl-substituted or unsubstituted C3-6 cycloalkyl, hydroxyl-substituted or unsubstituted 3- to 6-membered heterocycloalkyl containing 1 to 3 heteroatoms selected from O, S and N.

Preferably,

X is C or N;

Y, W and Z are each independently C or N;

A is S, N, SO$_2$, O or absent;

Q is substituted or unsubstituted C1-3 straight-chain or branched-chain alkylene, substituted or unsubstituted C3-5 cycloalkylene, phenyl, wherein substituent is —CD$_3$, C1-3 alkyl, C3-5 cycloalkyl, C3-5 cycloalkylene or halogen selected from fluorine, chlorine, bromine and iodine;

M is H, Na, K, Ca or C1-4 alkyl;

R$^1$, R$^2$ and R$^3$ are each independently hydrogen, halogen or absent;

R$^a$ and R$^b$ are each independently hydrogen, C1-3 alkyl or bond to each other to form a substituted or unsubstituted benzene ring structure, wherein the substituent in the substituted benzene ring structure is halogen, C1-3 alkyl or C1-3 alkoxy;

R$^c$ is —CN, carboxyl, hydroxyl-substituted or unsubstituted C1-3 alkyl, hydroxyl-substituted or unsubstituted C3-5 cycloalkyl, hydroxyl-substituted or unsubstituted 3- to 5-membered heterocycloalkyl containing 1 to 3 heteroatoms selected from O, S and N.

More preferably,

X is C or N;

Y, W and Z are each independently C or N;

A is S, N, SO$_2$, O or absent;

Q is substituted or unsubstituted C1-3 straight-chain or branched-chain alkylene,

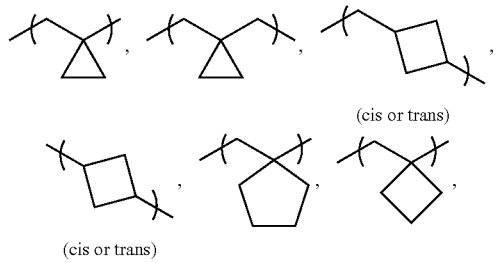

(cis or trans)

phenyl, wherein substituent is methyl, ethyl, propyl, —CD$_3$, C3-5 cycloalkyl, C3-5 cycloalkylene or fluorine;

M is H;

R$^1$, R$^2$ and R$^3$ are each independently hydrogen, halogen or absent;

R$^a$ and R$^b$ are each independently hydrogen, or bond to each other to form a benzene ring;

R$^c$ is —CN, carboxyl, methyl, ethyl, propyl, hydroxymethyl, hydroxyethyl, hydroxypropyl, cyclopropyl, cyclobutyl, hydroxyl-substituted cyclopropyl, hydroxyl-substituted cyclobutyl, oxiranyl, oxetanyl, hydroxyl-substituted oxiranyl or hydroxyl-substituted oxetanyl.

Further preferably,

X is C or N;

Y, W and Z are each independently C or N;

A is S;

Q is substituted or unsubstituted ethylene, propylene, isopropylidene,

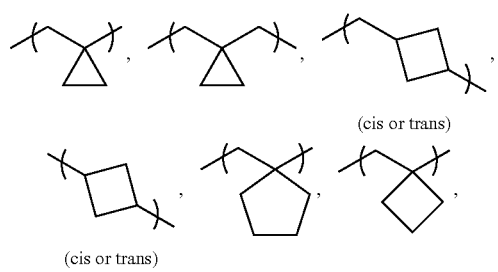

(cis or trans)

phenyl, wherein substituent is methyl, ethyl, propyl, —CD$_3$, cyclopropyl, cyclobutyl, cyclopentyl, cyclopropylidene, cyclobutylidene, cyclopentylidene or fluorine;

M is H;

R$^1$, R$^2$ and R$^3$ are each independently hydrogen, halogen or absent;

R$^a$ and R$^b$ are each independently hydrogen, or bond to each other to form a benzene ring;

R$^c$ is —CN, carboxyl, methyl, ethyl, propyl, hydroxymethyl, hydroxyethyl, hydroxypropyl, cyclopropyl, cyclobutyl, hydroxyl-substituted cyclopropyl, hydroxyl-substituted cyclobutyl, oxiranyl, oxetanyl, hydroxyl-substituted oxiranyl or hydroxyl-substituted oxetanyl.

According to another embodiment of the present invention, the carboxylic acid compound according to the present invention is selected from the following specific compounds 1 to 41:

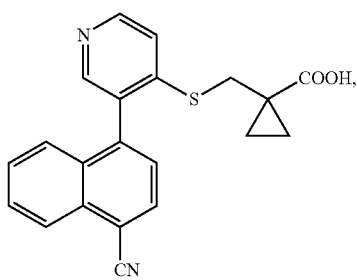

1

-continued
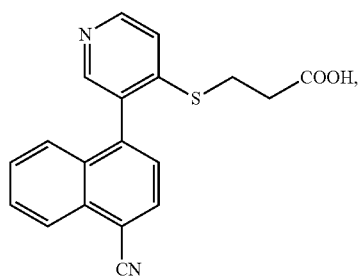
2
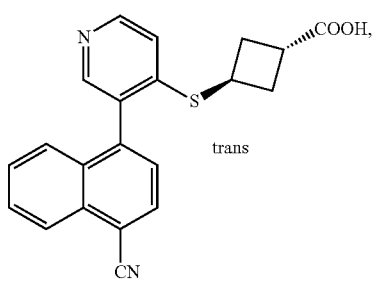
7
trans
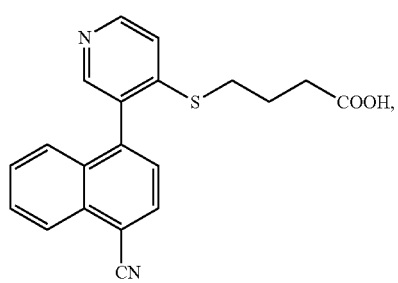
3
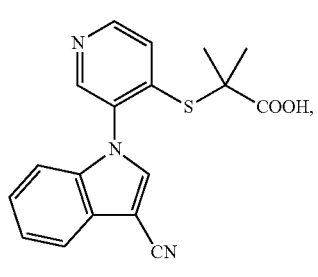
8
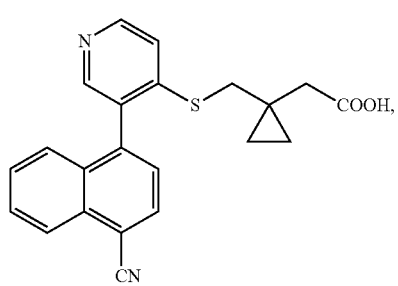
4
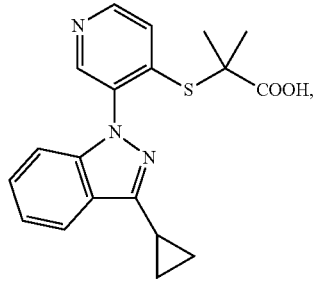
9
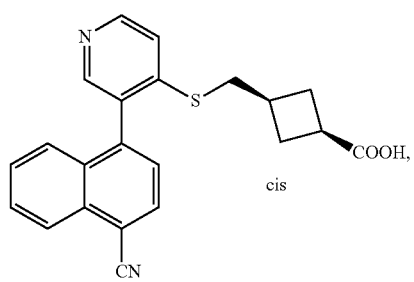
5
cis
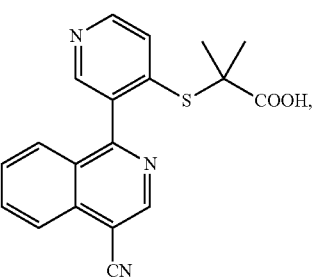
10
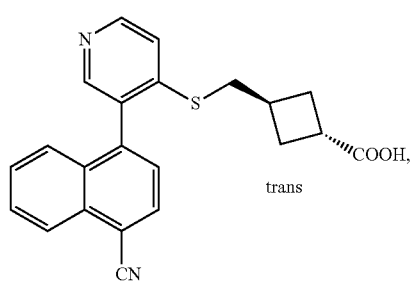
6
trans
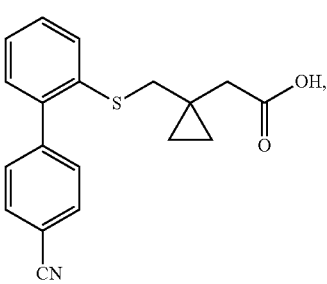
11

-continued

11
-continued
22
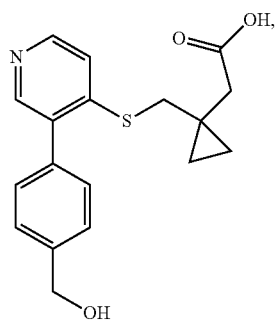
23
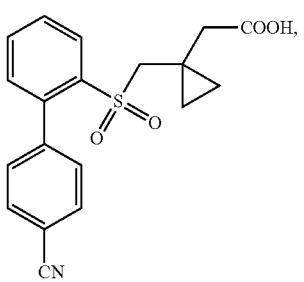
24
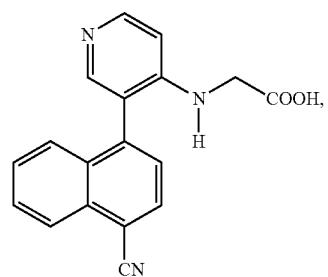
25
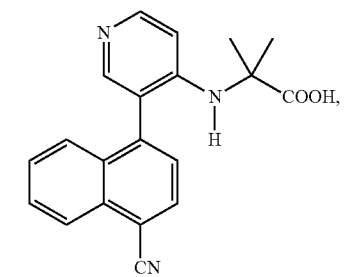
26
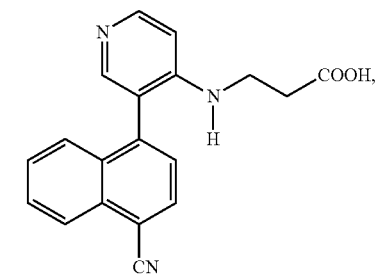
12
-continued
27
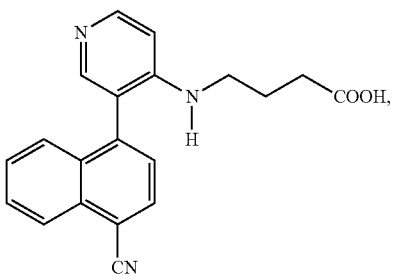
28
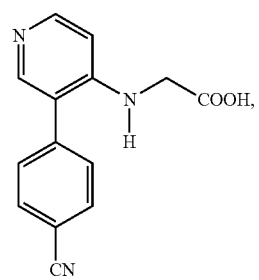
29
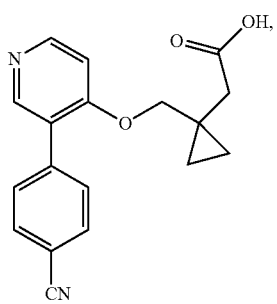
30
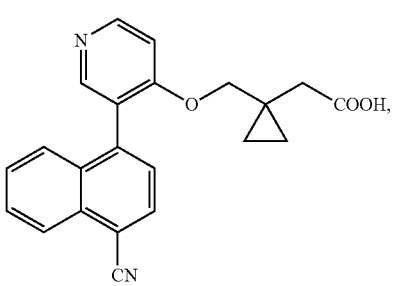
31
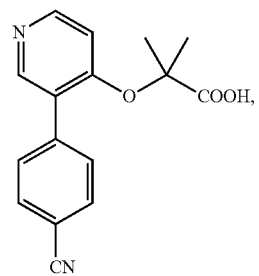

32

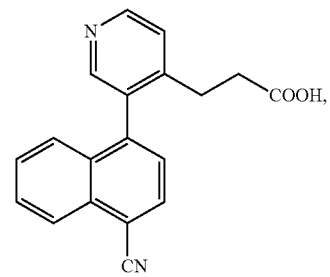

33

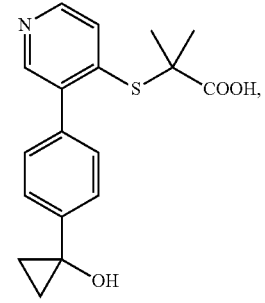

34

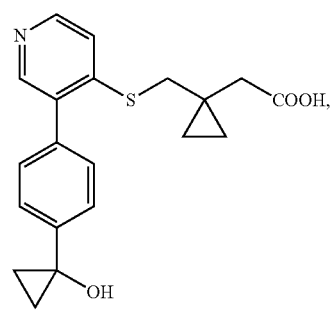

35

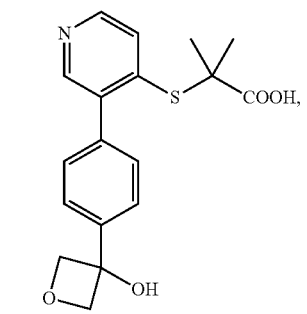

36

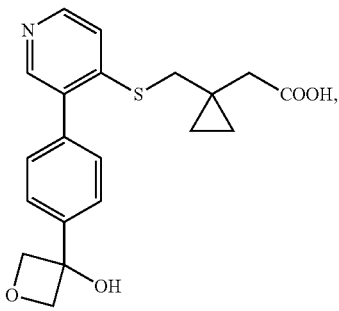

37

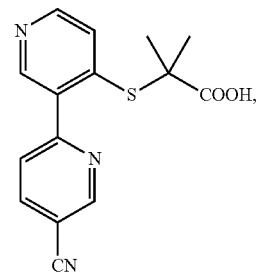

38

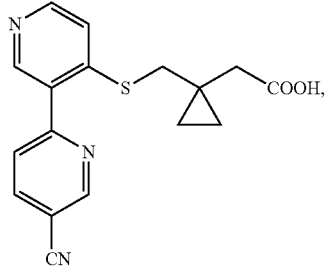

39

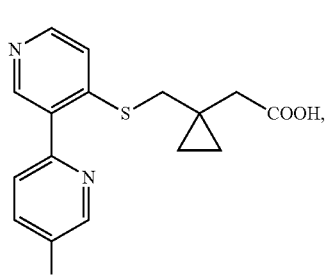

40

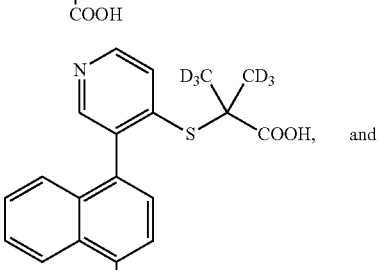

and

41

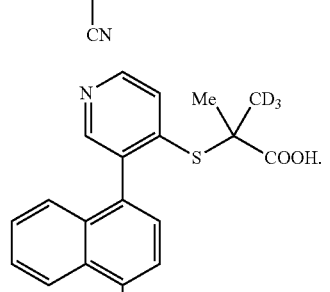

In the present invention, the pharmaceutically acceptable salts of the compounds in the present invention are not particularly limited, as long as they are pharmaceutically acceptable, examples include, but are not limited to, ammonium salts, alkali metal salts and alkaline-earth metal salts, such as ammonium salts, sodium salts, potassium salts, calcium salts and the like.

The present invention also includes isotopically-labeled compounds of the present invention, these isotopically-labeled compounds are identical to those recited herein, except that one or more atoms have an atomic mass or mass number different from the atomic mass or mass number usually found in nature. Examples of isotopes that can be incorporated into compounds of the invention include isotopes of hydrogen, carbon, nitrogen, oxygen, fluorine and chloride, such as $^2$H, $^3$H, $^{13}$C, $^{14}$C, $^{15}$N, $^{18}$O, $^{17}$O, $^{18}$F and $^{36}$Cl.

Certain isotopically-labeled compounds of the present invention (for example, compounds labeled with $^3$H and $^{14}$C) can be used in compounds and/or substrate tissue distribution assays. Tritiated (i.e., $^3$H) and carbon-14 (i.e., $^{14}$C) isotopes are particularly preferred for their ease of preparation and detection. Further, substitution with heavy isotopes such as deuterium (i.e., $^2$H) may produce certain therapeutic advantages resulting from greater metabolic stability (for example, extension of half-life in vivo or reduction of dose requirements), and thus being preferably used in certain conditions. The isotopically-labeled compounds of the present invention may generally be prepared by replacing non-isotope labeled agents with isotopically-labeled agents, by following the procedures similar to those disclosed in the flow routes and/or examples below.

In the present invention, the prodrugs of the compounds of the present invention are not particularly limited, as long as they can be metabolized in vivo into the compounds of the present invention, examples include, but are not limited to, esters etc., such as methyl ester, ethyl ester and the like.

Further objective of the present invention is to provide a preparation process of the carboxylic acid compound, and pharmaceutically acceptable salts, prodrugs, and solvates thereof, the process comprises:

Reaction Route 1:

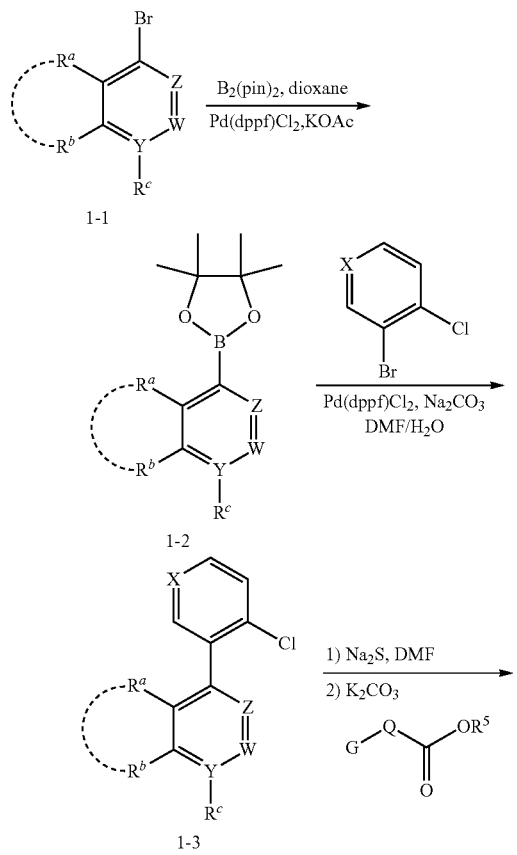

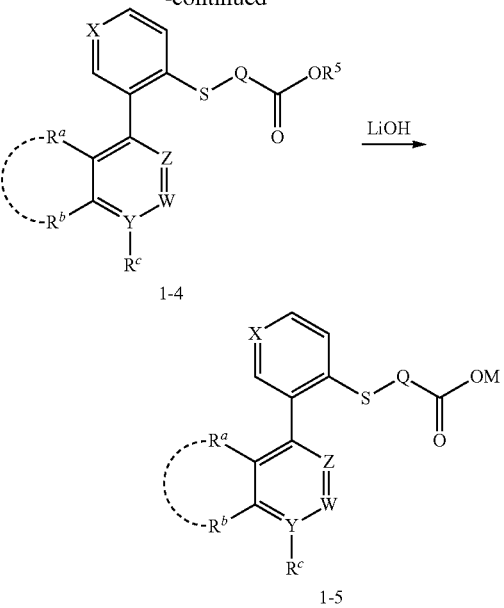

Step 1: The starting reactant 1-1 is dissolved in dioxane, then potassium acetate, bis(pinacolato)diboron (B$_2$(pin)$_2$) and palladium catalyst [1,1'-bis(diphenylphosphino)ferrocene]dichloropalladium are added thereto, the mixture is heated and reacted until the reaction is completed. The reaction solution is cooled, quenched by addition of ice water, extracted with ethyl acetate, then the organic phase is combined and washed with saturated brine. The organic phase is dried over sodium sulfate, then rotatory evaporated and purified by column chromatography, to give compound (1-2).

Step 2: 3-bromo-4-chloropyridine or 2-bromo-1-chlorobenzene is dissolved in dimethyl formamide and water, compound (1-2) obtained in step 1, sodium carbonate, palladium catalyst [1,1'-bis(diphenylphosphino) ferrocene] dichloropalladium are added thereto, then the resulting mixture is heated and reacted. The reaction solution is cooled, quenched in ice water, extracted with ethyl acetate, washed with saturated brine, and dried over anhydrous sodium sulfate, then rotatory evaporated and purified by column chromatography, to give compound (1-3).

Step 3: To compound (1-3) obtained in step 2 dissolved in dimethyl formamide, is added sodium sulfide, the resulting mixture is heated and reacted, then cooled down to room temperature, after that, anhydrous potassium carbonate and a reactant

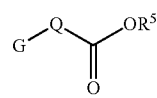

(which is determined by the structure of the final products) are added thereto, the reaction is carried out at higher temperature until the reaction is completed. The reaction solution is cooled, quenched in ice water and extracted with ethyl acetate, then the organic phase is dried over anhydrous sodium sulfate, filtered and rotatory evaporated, to give compound (1-4). The crude product is directly subject to the next step.

Step 4: The reaction is carried out overnight between compound (1-4) obtained in step 3 and lithium hydroxide in tetrahydrofuran and water at room temperature. Tetrahydrofuran is removed by concentration, and aqueous phase is extracted with dichloromethane and collected. Aqueous phase is then adjusted to pH 4-5 using 2N of hydrochloric acid regulating system, and extracted with dichloromethane. The organic phase is combined, dried and rotatory evaporated, to give the final compound of chemical formula (1-5).

Reaction Route 2:

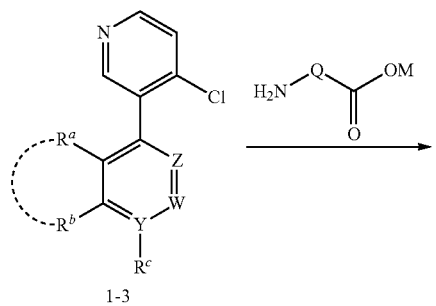

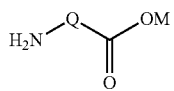

(which is determined by the structure of the final product) in phenol at higher temperature. Then, the reaction solution is cooled down to room temperature, added with ether and filtered. The filter cake is purified by preparative reverse phase chromatography to give the final product (2-1).

Reaction Route 3:

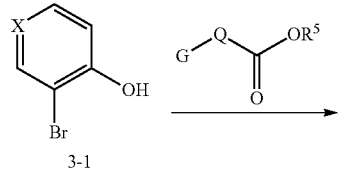

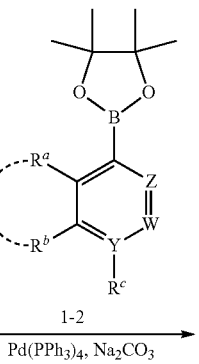

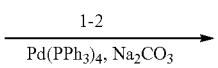

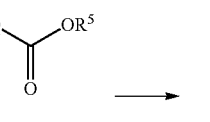

Step 1: A reactant

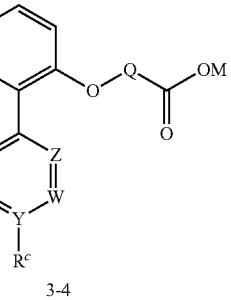

which is determined by the structure of final product, triphenylphosphine and diethyl azodicarboxylate are sequentially added to 3-bromopyridin-4-ol or 2-bromophenol (3-1) dissolved in tetrahydrofuran under the protection of nitrogen at 0° C., then the mixture is warmed to room temperature and reacted. The reaction solution is directly concentrated and then purified by preparative silica gel plate to give compound (3-2).

Step 2: The resulting compound (3-2), aqueous solution of sodium carbonate, compound (1-2) and tetrakis(triphenylphosphine) palladium(0) are added to dioxane, heated to 80° C. and reacted for 12 hours. Then the reaction solution is cooled down to room temperature, the reaction solution is added with ethyl acetate, and washed with water and brine. The organic phase is dried, filtered, concentrated and purified by preparative silica gel plate, to give compound (3-3).

Step 3: Compound (3-3), lithium hydroxide or sodium hydroxide are added to tetrahydrofuran/water, and the mixture was reacted at room temperature for hours. Then the pH of the reaction solution is adjusted with concentrated hydrochloric acid, and the reaction solution is added with ethyl acetate, washed with water and brine. The organic phase is dried, filtered, concentrated and purified by preparative silica gel plate, to give compound (3-4).

Reaction Route 4:

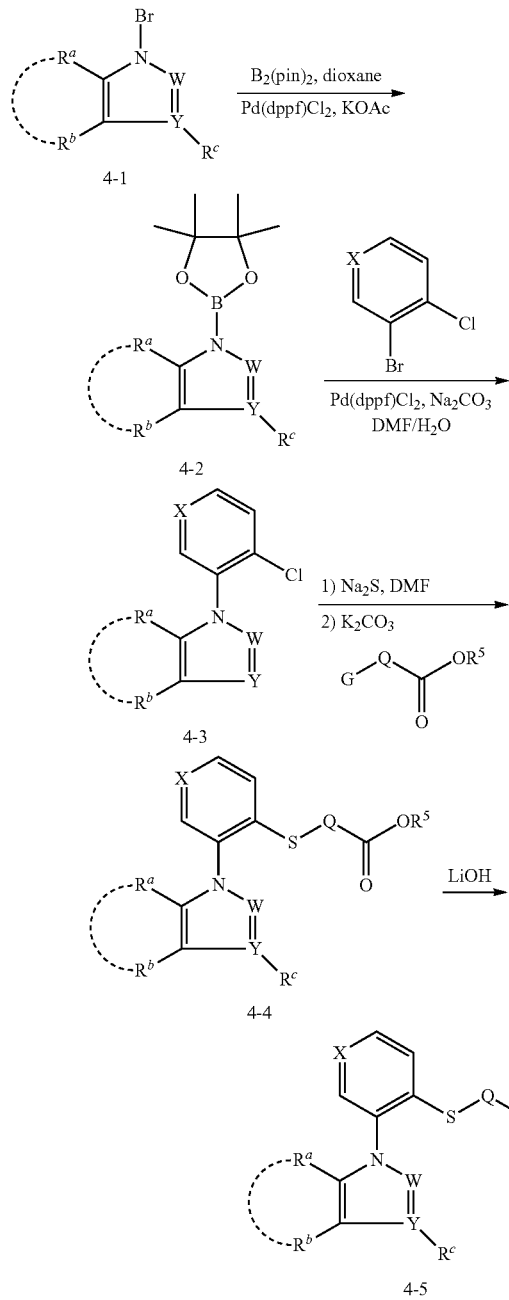

organic phase is dried over sodium sulfate, then rotatory evaporated and purified by column chromatography, to give compound (4-2).

Step 2: 3-bromo-4-chloropyridine or 2-bromo-1-chlorobenzene is dissolved in dimethyl formamide and water, compound (4-2) obtained in step 1, sodium carbonate, palladium catalyst [1,1'-bis(diphenylphosphino)ferrocene]dichloropalladium are added thereto at the same time, then the resulting mixture is heated and reacted. The reaction solution is cooled, quenched in ice water, extracted with ethyl acetate, washed with saturated brine, dried over sodium sulfate, then rotatory evaporated and purified by column chromatography, to give compound (4-3).

Step 3: To compound (4-3) obtained in step 2 dissolved in dimethyl formamide, is added sodium sulfide, the resulting mixture is heated and reacted, then cooled down to room temperature, after that, anhydrous potassium carbonate and a reactant (which is determined by the structure of the final product) are added thereto, and the reaction is carried out at higher temperature until the reaction is completed. The reaction solution is cooled, quenched in ice water and extracted with ethyl acetate, then the organic phase is dried over sodium sulfate, filtered and rotatory evaporated, to give compound (4-4). The crude product is directly subject to the next step.

Step 4: The reaction is carried out overnight between compound (4-4) obtained in step 3 and lithium hydroxide in tetrahydrofuran and water at room temperature. Tetrahydrofuran is removed by concentration, and aqueous phase is extracted with dichloromethane and collected. Then the aqueous phase is adjusted to pH 4-5 using 2N of hydrochloric acid regulating system, and extracted with dichloromethane. The organic phase is combined, dried, then rotatory evaporated, to give the final compound of chemical formula (4-5).

Reaction Route 5:

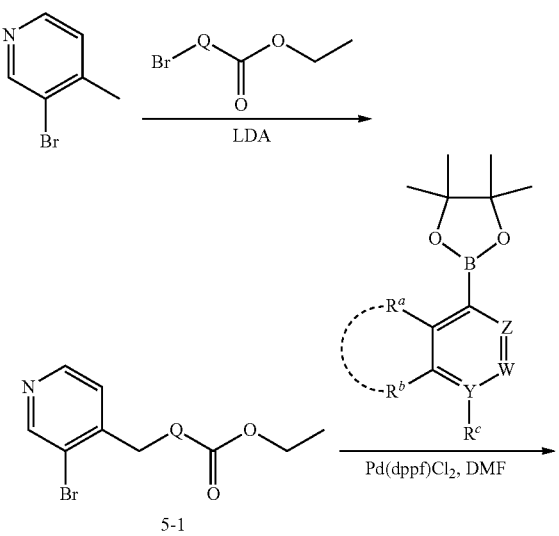

Step 1: The starting reactant 4-1 is dissolved in dioxane, then potassium acetate, bis(pinacolato)diboron ($B_2(pin)_2$) and palladium catalyst [1,1'-bis(diphenylphosphino)ferrocene]dichloropalladium are added thereto, then the mixture is heated and reacted until the reaction is completed. The reaction solution is cooled, quenched by addition of ice water and extracted with ethyl acetate, then the organic phase is combined and washed with saturated brine. The Step 1: 3-bromo-4-methylpyridine is dissolved in tetrahydrofuran, the solution is cooled and then lithium diisopropylamide (LDA) is added thereto and reacted, then the reactant

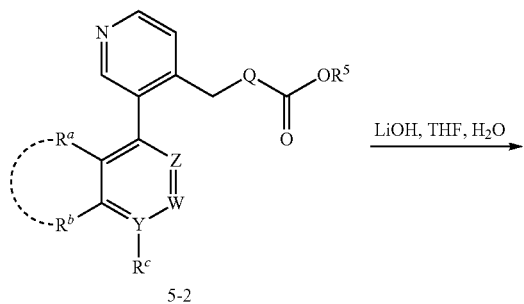

which is determined by the structure of the final product, is added dropwise thereto and the reaction is continued. Thereafter, the reaction is quenched with saturated sodium bicarbonate solution, and then the reaction solution is added with ethyl acetate, washed with water and brine. The organic phase is dried, filtered, concentrated and purified by preparative silica gel plate, to give compound (5-1).

Step 2: Compound (5-1), aqueous solution of sodium carbonate, compound (1-2), [1,1'-bis(diphenylphosphino)ferrocene]dichloropalladium are added to dimethyl formamide, heated until they reacted. The reaction solution is added with ethyl acetate, washed with water and brine. The organic phase is dried, filtered, concentrated and purified by preparative silica gel plate, to give compound (5-2).

Step 3: Compound (5-2) and lithium hydroxide are added to tetrahydrofuran/water and reacted at room temperature. The pH of reaction solution is adjusted with dilute hydrochloric acid (1 M), and then the reaction solution is added with ethyl acetate, washed with water and brine. The organic phase is dried, filtered, concentrated and purified by preparative silica gel plate, to give compound (5-3).

Step 1: Compound (1-3), anhydrous potassium carbonate and reactant

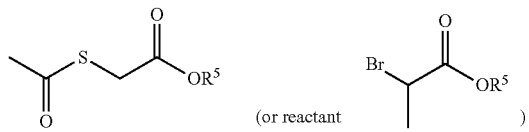

(or reactant)

are added to dimethyl formamide, stirred at room temperature, then stirred at higher temperature. The mixture is then cooled to room temperature, added with water and ethyl acetate, after that, the organic layer is washed with saturated brine, dried over sodium sulfate, and the solvent is distilled off under reduced pressure, to obtain a crude brown oil which is purified by column chromatography to yield compound (6-1-1) and compound (6-2-1) respectively.

Step 2: Compound (6-1-1) and compound (6-2-1) are dissolved in tetrahydrofuran respectively, and are slowly added by dropwise to suspension of sodium hydride in dimethyl formamide at 0° C. while stirring, a solution of Iodomethane-d3 in dimethyl formamide is further added thereto at 0° C., then the resulting mixture is stirred overnight at room temperature. The reaction is quenched by addition water, its pH is adjusted with 1 N hydrochloric acid, then the solvent is distilled off under reduced pressure, and the remaining oily substance is purified by preparative HPLC, to give compound (6-1-2) and compound (6-2-2) respectively.

Step 3: Compound (6-1-2) and lithium hydroxide are added to tetrahydrofuran/water (3 mL/1 mL), and reacted at room temperature. The reaction solution is adjusted to pH 4 with dilute hydrochloric acid (1 M), then the reaction solution is added with ethyl acetate and washed with brine. The organic phase is dried, filtered, concentrated and preparatively purified, to give compound (6-1-3).

According to another aspect of the invention, further provided herein is a use of the carboxylic acid compound, and pharmaceutically acceptable salts, prodrugs, and solvates thereof in the preparation of a drug that promotes the excretion of uric acid, preferably, a drug that promotes the excretion of uric acid with URAT1 as a target.

According to another aspect of the invention, further provided herein is a pharmaceutical composition comprising one or more selected from the carboxylic acid compound, and pharmaceutically acceptable salts, prodrugs, and solvates thereof, and optionally a pharmaceutically acceptable carrier.

According to another aspect of the invention, further provided herein is a use of the carboxylic acid compound, and pharmaceutically acceptable salts, prodrugs, and solvates thereof or pharmaceutical composition thereof in the preparation of a drug for the treatment or prevention of a disease or disorder caused by abnormal organ or tissue levels of uric acid in an individual.

Wherein, the disease or disorder caused by abnormal organ or tissue levels of uric acid in an individual includes: gout, gouty arthritis, a recurrent gout attack, hyperuricemia, joint inflammation, arthritis, urolithiasis, kidney disease, kidney stones, kidney failure, hypertension, cardiovascular disease, coronary heart disease, Lesch-Nyhan syndrome, Kelley-Seegmiller syndrome, plumbism, hyperparathyroidism, psoriasis and sarcoidosis.

Preferably, the disease or disorder is hyperuricemia in human and animals, or gout in human and animals.

According to another aspect of the invention, further provided herein is a use of the carboxylic acid compound, and pharmaceutically acceptable salts, prodrugs, and solvates thereof or the pharmaceutical composition thereof in the preparation of a drug for lowering blood levels of uric acid in human and animals.

According to another aspect of the invention, a use of the carboxylic acid compound, and pharmaceutically acceptable salts, prodrugs, and solvates thereof or the pharmaceutical composition thereof in the preparation of a drug for lowering blood levels of uric acid in human and animals.

Further provided herein is a combination of the carboxylic acid compound, and pharmaceutically acceptable salts, prodrugs, and solvates thereof or a pharmaceutical composition thereof with a second agent effective for the treatment of gout.

Wherein, the second agent is a xanthine oxidase inhibitor, a xanthine dehydrogenase inhibitor, a xanthine oxidoreductase inhibitor, or a combination thereof, preferably, allopurinol, febuxostat or a combination thereof.

The pharmaceutical composition or drugs provided herein can be in various forms, such as tablet, capsule, powder, syrup, solution, suspension and aerosol, etc., and can be present in suitable solid or liquid carriers or diluents and in disinfected instruments suitable for injection or infusion.

Various formulations of the pharmaceutical compositions or drugs of the present invention can be prepared according to conventional preparation processes in the pharmaceutical field. Unit dosage of these formulations contains 0.05 mg-200 mg compounds of formula (I) or (II), preferably, unit dosage of these formulations contains 0.1 mg-100 mg compounds of formula (I) or (II).

The compounds and pharmaceutical compositions of the present invention can be clinically used for mammals, including human and animals, and can be administered via oral, nasal, dermal, pulmonary, or gastrointestinal etc. administration routes, Oral route is the most preferable. The optimal preferred daily dosage is 0.001-10 mg/kg body weight, administered at one time, or 0.001-10 mg/kg body weight administered at divided doses. No matter what kinds of administration manners, the optimal dosage for an individual should be determined by specific treatment. Generally, the most suitable dosage can be obtained by gradually increasing dosages from a smaller dosage.

In the present invention, term "effective amount" may refer to an effective amount for dose and period of time required to achieve predicted effects. The effective amount may vary due to some factors, such as categories of diseases or syndromes of diseases during treatment, construction of a specific targeted organ being administered, body size of a patient or severity of diseases or syndromes. Without excessive experiments, those with common knowledge in the art can determine an effective amount for a specific compound by experience.

Technical Effects

The research on anti-uric acid activity demonstrates that the compounds of the present invention have superior activities in inhibiting the reabsorption of uric acid, and can be used as novel drugs for efficiently decreasing blood uric acid level, especially as URAT1 inhibitors.

SPECIFIC EMBODIMENTS

The present invention will be explained with reference to the specific examples below. It should be understood that, these examples are merely used for illustrating the present invention but not for limiting the scope of the invention. The experimental methods in the following examples, when detailed conditions are not specified, are carried out according to conventional conditions, or according to conditions provided or constructed by manufacturers. Unless defined or illustrated otherwise, all professional and scientific terms used herein have the same meaning as commonly known by a person skilled in the art. Additionally, any methods and materials similar or equivalent to the recorded contents can be used in the methods of the present invention.

In the synthetic processes of the following examples, starting materials were obtained from commercial sources, such as from Alfa Aesar (China) Chem Co. Ltd., Accela ChemBio Co. Ltd, PharmaBlock Sciences (Nanjing), Inc., Dalian Ally Chem Co. Ltd., Tianjin Fuchen chemical reagent factory, Beijing Jingqiu chemical product Co. Ltd., Zhangjiagang Aimate Chem Co. Ltd, Sinopharm chemical reagent Shaanxi Co., Ltd, etc.

EXAMPLES

Example 1: Synthesis of Compound 1

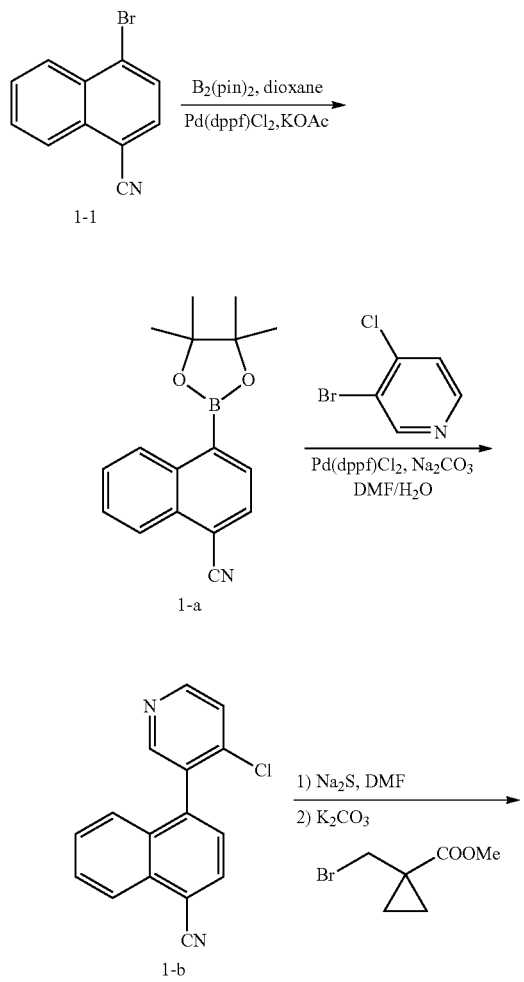

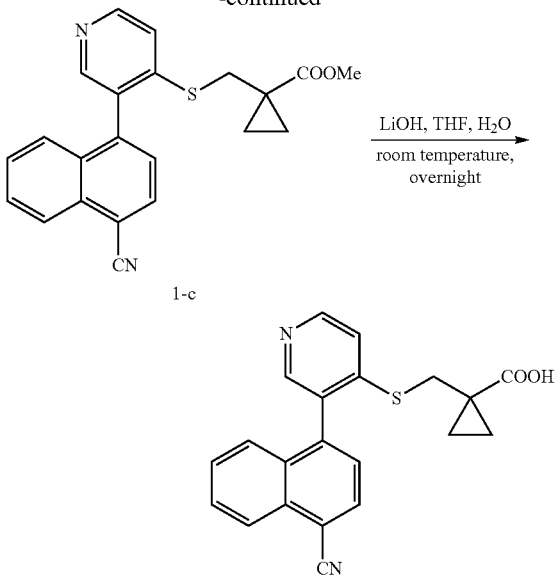

Step 1: Synthesis of 4-(4,4,5,5-tetramethyl-1,3,2-dioxaborolane-2-yl)-1-naphthonitrile (1-a)

In a three-necked flask (100 mL), potassium acetate (3.9 g, 39.8 mmol), bis(pinacolato)diboron ($B_2(pin)_2$) (4.0 g, 15.75 mmol) and palladium catalyst [1,1'-bis(diphenylphosphino)ferrocene]dichloropalladium (0.54 g, 0.66 mmol) were added to 4-bromo-1-naphthonitrile (3.0 g, 15.75 mmol) solution in dioxane (40 mL) under the protection of $N_2$, the mixture was heated to 90° C. and reacted for 3 hours until the reaction was completed. The reaction solution was cooled, quenched by addition of 100 mL ice water and extracted with ethyl acetate (100 mL, 3 times), then the organic phase was combined and washed with saturated brine (100 mL, 3 times). The organic phase was dried over sodium sulfate, then rotatory evaporated and purified by column chromatography (petroleum ether/ethyl acetate=20:1~10:1), to give an off-white solid product 4-(4,4,5,5-tetramethyl-1,3,2-dioxaborolane-2-yl)-1-naphthonitrile (1-a).

Step 2: Synthesis of 4-(4-chloropyridin-3-yl)-1-naphthonitrile (1-b)

In a three-necked flask (100 mL), 4-(4,4,5,5-tetramethyl-1,3,2-dioxaborolane-2-yl)-1-naphthonitrile (2.4 g, 8.6 mmol) obtained in step 1, sodium carbonate (2.8 g, 26.42 mmol), palladium catalyst [1,1'-bis(diphenylphosphino)ferrocene]dichloropalladium (0.35 g, 0.43 mmol) were added at the same time to 3-bromo-4-chloropyridine (1.6 g, 8.31 mmol) solution in dimethyl formamide (40 mL) and water (4.8 mL) under the protection of $N_2$, then the mixture was heated to 130° C. and reacted for 5 hours. The reaction solution was cooled, quenched by addition of 100 mL ice water, extracted with ethyl acetate (100 mL, 3 times), washed with saturated brine (100 mL, 3 times) and dried over sodium sulfate, then rotatory evaporated and purified by column chromatography (petroleum ether/ethyl acetate=10:1~petroleum ether/ethyl acetate/dichloromethane=1:1:1), to give an off-white solid product 4-(4-chloropyridin-3-yl)-1-naphthonitrile (1-b).

Step 3: Synthesis of methyl 1-(((3-(4-cyanonaphthalen-1-yl)pyridin-4-yl)thio)methyl)cyclopropanecarboxylate (1-c)

In a three-necked flask (100 mL), under the protection of N$_2$, 4-(4-chloropyridin-3-yl)-1-naphthonitrile (200 mg, 0.70 mmol) obtained in step 2 was dissolved in dimethyl formamide (20 mL), sodium sulfide (355 mg, 4.50 mmol) was added thereto, then the mixture was heated to 130° C. and reacted for about 1 hour, after being cooled down to room temperature, anhydrous potassium carbonate (523 mg, 3.70 mmol) and methyl 1-(bromomethyl)cyclopropanecarboxylate (440 mg, 2.20 mmol) are sequentially added thereto, and then the resulting mixture was heated to 130° C. and further reacted for about 1.1 hour until the reaction was completed. The reaction solution was cooled, added with 100 mL ice water to quench the reaction and extracted with ethyl acetate (100 mL, 3 times), then the organic phase was dried over anhydrous sodium sulfate, filtered and rotatory evaporated, to give 450 mg of yellow oily product methyl 1-(((3-(4-cyanonaphthalen-1-yl)pyridin-4-yl)thio)methyl)cyclopropanecarboxylate (1-c). The crude product was directly subject to the next step.

Step 4: Synthesis of 1-(((3-(4-cyanonaphthalen-1-yl)pyridin-4-yl)thio)methyl)cyclopropanecarboxylic acid (compound 1)

Methyl 1-(((3-(4-cyanonaphthalen-1-yl)pyridin-4-yl)thio)methyl)cyclopropanecarboxylate (450 mg, 1.20 mmol) obtained in step 3, lithium hydroxide (90 mg, 3.70 mmol), tetrahydrofuran (30 mL) and water (10 mL) were added into a three-necked flask (100 mL) under the protection of N$_2$, and the mixture was reacted overnight at room temperature. The resulting mixture was concentrated to remove tetrahydrofuran, aqueous phase was extracted 3 times with dichloromethane (50 mL), and the aqueous phase was collected. The aqueous phase was adjusted to pH=4-5 with 2N of hydrochloric acid regulating system, and then extracted with dichloromethane (100 mL, 3 times). The organic phase was combined, dried with sodium sulfate, and then rotatory evaporated. The crude product was prepared by high pressure to yield compound 1, a white solid product.

LC-MS (ES, m/z): 361 [M+H]$^+$. H-NMR (300 MHz, d$_6$-DMSO, ppm): δ 0.86-0.94 (m, 2H), 1.08-1.14 (m, 2H), 3.38 (s, 2H), 7.54-7.57 (d, J=8.1 Hz, 1H), 7.65-7.91 (m, 4H), 8.23-8.26 (d, J=8.4 Hz, 1H), 8.31-8.33 (d, J=7.5 Hz, 1H), 8.49 (s, 1H), 8.69-8.71 (d, J=6 Hz, 1H).

Example 2: Synthesis of Compound 2

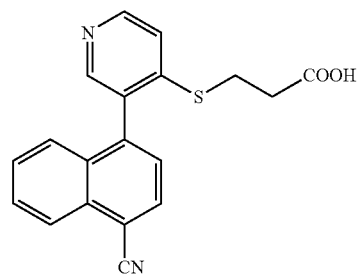 [SMILES: N#Cc1ccc(-c2cnccc2SCCC(=O)O)c2ccccc12]

Compound 2 was synthesized by a method similar to that in Example 1, except that methyl 1-(bromomethyl)cyclopropanecarboxylate was replaced with the corresponding compound in step 3.

LC-MS (ES, m/z): 335 [M+H]$^+$. H-NMR (300 MHz, CD$_3$OD, ppm): δ2.61-2.65 (m, 2H), 3.23-3.28 (m, 2H), 7.53-7.66 (m, 4H), 7.78-7.83 (m, 1H), 8.11-8.13 (d, J=7.2 Hz, 1H), 8.29-8.32 (d, J=8.4 Hz, 2H), 8.56 (m, 1H).

Example 3: Synthesis of Compound 3

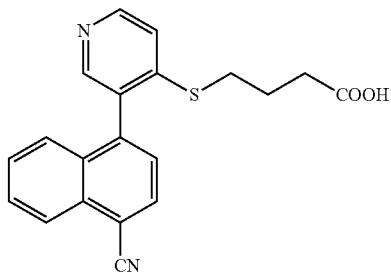 [SMILES: N#Cc1ccc(-c2cnccc2SCCCC(=O)O)c2ccccc12]

Compound 3 was synthesized by a method similar to that in Example 1, except that methyl 1-(bromomethyl)cyclopropanecarboxylate was replaced with the corresponding compound in step 3.

LC-MS (ES, m/z): 349 [M+H]$^+$. H-NMR (300 MHz, CDCl$_3$, ppm): δ1.69-1.79 (m, 2H), 2.24-2.29 (m, 2H), 2.95-3.00 (m, 2H), 7.47-7.50 (d, J=8.4 Hz, 1H), 7.57-7.70 (m, 3H), 7.82-7.88 (m, 1H), 8.12-8.31 (m, 3H), 8.58-8.60 (d, J=5.4 Hz, 1H), 12.15 (br, 1H).

Example 4: Synthesis of Compound 18

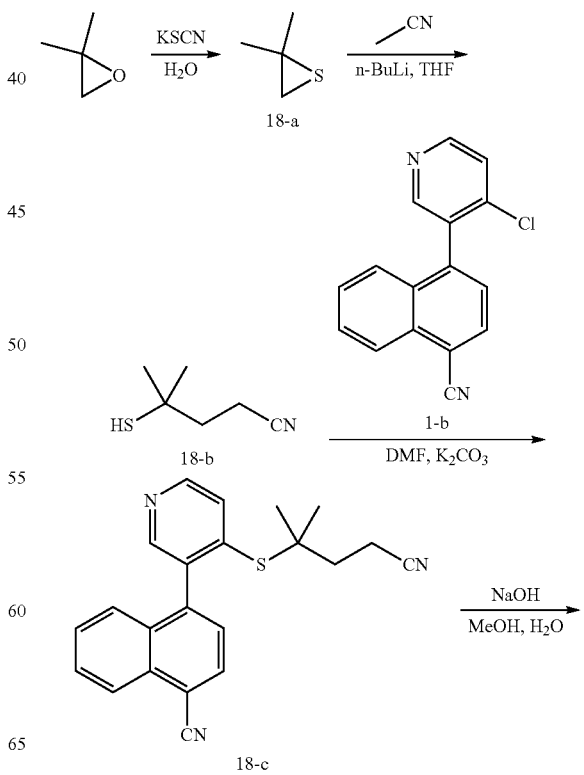

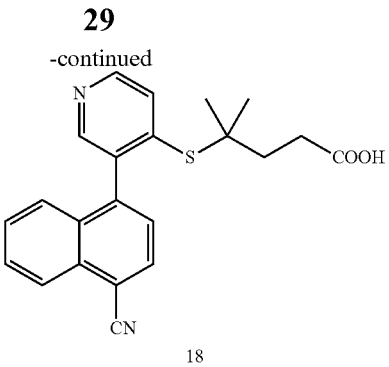

18

Step 1: Synthesis of 2,2-dimethylthiirane (18-a)

Potassium thiocyanate (9.7 g, 0.1 mol) was dissolved in water (10 mL), and 2,2-dimethyloxirane (7.2 g, 0.1 mol) was added thereto at room temperature. After the mixture was reacted for 4 hours, the supernatant was added dropwise to the aqueous solution (5 mL) of potassium thiocyanate (5 g, 0.05 mol), and the reaction was lasted for another 16 hours. The reaction solution was added with ether (50 mL) and water (30 mL), and the organic phase was further washed with brine (10 mL). Then the organic phase was dried, filtered and concentrated to yield a yellow oily product.

Step 2: Synthesis of 4-mercapto-4-methylpentanenitrile (18-b)

In a three-necked flask (100 mL), n-butyllithium (2.5 M in hexane, 3.6 mL, 9 mmol) was dissolved in tetrahydrofuran (10 mL) under the protection of nitrogen, the solution was cooled to −78° C., then acetonitrile (378 mg, 9 mmol) was added thereto, the mixture was reacted for 0.5 hour, to which was further added dropwise a solution of 18-a (800 mg, 9 mmol) in tetrahydrofuran (20 mL), the resulting mixture was heated to room temperature and reacted for another 4 hours. The reaction was quenched with 1 N hydrochloric acid (9 mL) at 0° C., then the reaction solution was added with ethyl acetate (50 mL), then washed with brine (10 mL). The organic phase was dried, filtered and concentrated to yield a yellow oily product.

Step 3: Synthesis of 4-(4-((4-cyano-2-methylbutan-2-yl)thio)pyridin-3-yl)-1-naphthonitrile (18-c)

In a single-necked flask (100 mL), 18-b (600 mg, 4.65 mmol), anhydrous potassium carbonate (641 mg, 4.65 mmol) and 1-b (300 mg, 1.13 mmol) were added to dimethyl formamide (15 mL), the mixture was heated to 130° C. and reacted for 2 hours. The reaction solution was cooled, added with ethyl acetate (50 mL), washed with water (30 mL) and brine (30 mL). The organic phase was dried, filtered, concentrated, and purified by silica gel column (petroleum ether/ethyl acetate=1:1) to yield a white solid.

Step 4: Synthesis of 4-((3-(4-cyanonaphthalen-1-yl)pyridin-4-yl)thio)-4-methylpentanoic acid (18)

18-c (190 mg, 0.53 mmol) and 1 M of aqueous solution of sodium hydroxide (2.1 mL, 2.1 mmol,) were added to tetrahydrofuran/methanol (2 mL/8 mL) in a single-necked flask (50 mL), and the mixture was reacted at 65° C. for 36 hours. The reaction solution was concentrated, adjusted to pH=4 with 1N hydrochloric acid, then it was added with ethyl acetate (50 mL) and washed with brine (50 mL). The organic phase was dried, filtered, concentrated and purified by preparative reverse phase chromatography to yield a white solid product.

LC-MS (ES, m/z): 377 [M+H]$^+$; H-NMR (400 MHz, DMSO-d6, ppm): δ 12.00 (s, 1H), 8.62 (d, J=5.2 Hz, 1H), 8.44 (s, 1H), 8.18-8.23 (m, 2H), 7.81 (m, 1H), 7.72 (d, J=5.2 Hz, 1H), 7.65 (m, 1H), 7.55 (d, J=7.6 Hz, 1H), 7.39 (d, J=8.4 Hz, 1H), 2.02 (m, 2H), 1.72 (m, 1.13 (s, 6H).

Example 5: Synthesis of Compound 4

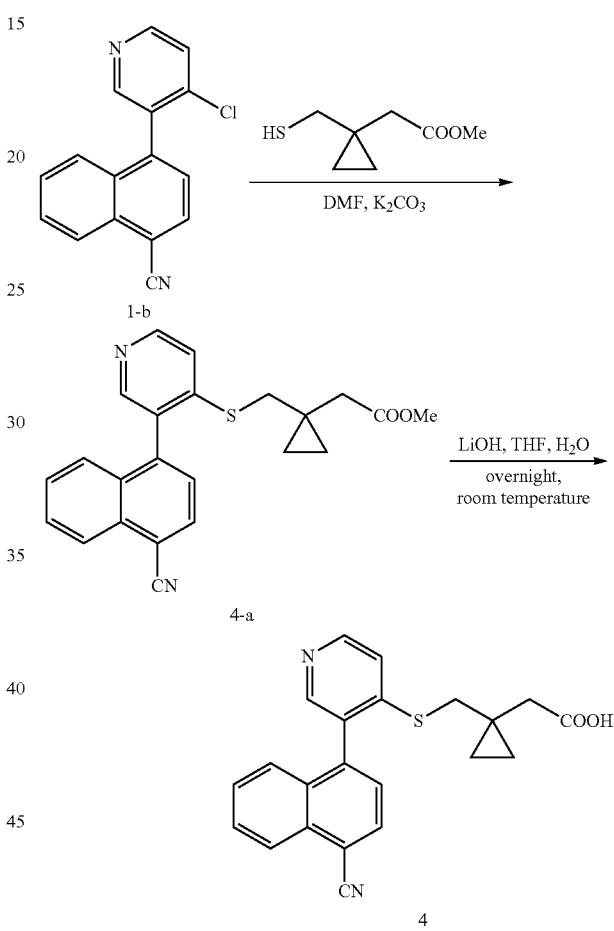

Step 1: Synthesis of methyl 2-1-(((3-(4-cyanonaphthalen-1-yl)pyridin-4-yl)thio)methyl)cyclopropyl) acetate (4-a)

In a three-necked flask (100 mL), under the protection of $N_2$, anhydrous potassium carbonate (523 mg, 3.70 mmol) and methyl 2-(1-(mercaptomethyl)cyclopropyl)acetate (300 mg, 1.90 mmol) were sequentially added to 4-(4-chloropyridin-3-yl)-1-naphthonitrile (200 mg, 0.70 mmol) solution in dimethyl formamide (20 mL), the mixture was heated to 130° C. and reacted for about 2 hour until the reaction was completed. The reaction solution was cooled, added with 100 mL ice water to quench the reaction, and extracted with ethyl acetate (100 mL, 3 times), then organic phase was reversely washed with saturated brine (100 mL, 4 times).

The organic phase was dried over anhydrous sodium sulfate, and then rotatory evaporated to yield a yellow oily product. The crude product was directly subject to the next step.

Step 2: Synthesis of 2-(1-(((3-(4-cyanonaphthalen-1-yl)pyridin-4-yl)thio)methyl)cyclopropyl)acetic acid (compound 4)

Methyl 2-(1-(((3-(4-cyanonaphthalen-1-yl)pyridin-4-yl)thio)methyl)cyclopropyl)acetate (417 mg, 1.07 mmol) obtained in step 1, lithium hydroxide (78 mg, 3.26 mmol), tetrahydrofuran (30 mL) and water (10 mL) were added into a three-necked flask (100 mL) under the protection of $N_2$, and the mixture was reacted overnight at room temperature. Then, the resulting solution was concentrated to remove tetrahydrofuran, aqueous phase was extracted 3 times with dichloromethane (50 mL), and the aqueous phase was collected. After that, the aqueous phase was adjusted to pH=4-5 with 2N of hydrochloric acid regulating system, and then extracted with dichloromethane (100 mL, 3 times). The organic phase was combined, dried over sodium sulfate, rotatory evaporated, prepared by high pressure, and then rotatory evaporated. The resultant was lyophilized to yield a white solid.

LC-MS (ES, m/z): 375 [M+H]$^+$. H-NMR (300 MHz, CDCl$_3$, ppm): δ 0.43 (m, 4H), 2.06-2.18 (m, 2H), 3.13-3.22 (m, 2H), 7.48-7.70 (m, 4H), 7.83-7.88 (m, 1H), 8.22-8.30 (m, 3H), 8.54-8.56 (d, J=5.4 Hz, 1H), 12.23 (br, 1H).

Example 6: Synthesis of Compound 5

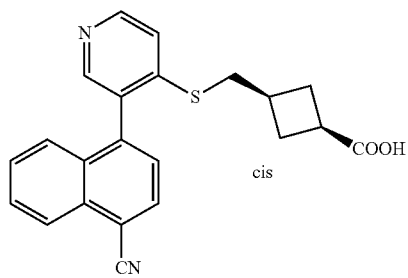 [SMILES: N#Cc1ccc(-c2cnccc2SC[C@H]2C[C@@H](C(=O)O)C2)c2ccccc12]

Compound 5 was synthesized by a method similar to that in Example 5, except that methyl 2-(1-(mercaptomethyl)cyclopropyl)acetate was replaced with the corresponding compound in step 1.

LC-MS (ES, m/z): 375 [M+H]$^+$. H-NMR (300 MHz, CDCl$_3$, ppm): δ 1.92-2.01 (m, 2H), 2.34-2.47 (m, 3H), 2.97-3.03 (m, 3H), 7.37-59 (m, 3H), 7.72-7.77 (t, J=7.8 Hz, 1H), 7.99-8.01 (d, J=7.2 Hz, 1H), 8.33-8.36 (d, J=8.4 Hz, 1H), 8.57-8.59 (d, J=5.4 Hz, 2H), 8.61-8.66 (m, 1H).

Example 7: Synthesis of Compound 6

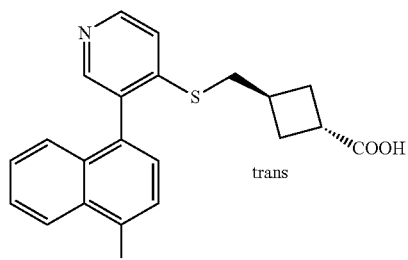

Compound 6 was synthesized by a method similar to that in Example 5, except that methyl 2-(1-(mercaptomethyl)cyclopropyl)acetate was replaced with the corresponding compound in step 1.

LC-MS (ES, m/z): 375 [M+H]$^+$. H-NMR (300 MHz, CDCl$_3$, ppm): δ 1.92-2.01 (m, 2H), 2.36-2.2.44 (m, 2H), 2.65-2.70 (m, 1H), 2.99-3.09 (m, 3H), 7.30-7.59 (m, 4H), 7.71-7.77 (m, 1H), 7.99-8.01 (d, J=7.2 Hz, 1H), 8.33-8.34 (m, 2H), 8.58-8.60 (m, 1H).

Example 8: Synthesis of Compound 12

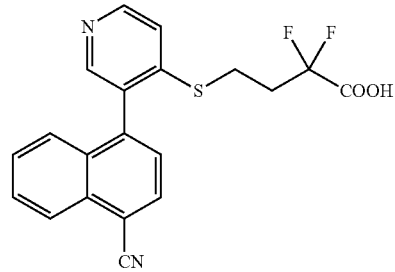 [SMILES: N#Cc1ccc(-c2cnccc2SCCC(F)(F)C(=O)O)c2ccccc12]

Compound 12 was synthesized by a method similar to that in Example 5, except that methyl 2-(1-(mercaptomethyl)cyclopropyl)acetate was replaced with the corresponding compound in step 1.

LC-MS (ES, m/z): 385 [M+H]$^+$. H-NMR (400 MHz, d$_6$-DMSO, ppm): δ 8.60 (d, J=6.4 Hz, 1H), 8.31 (s, 1H), 8.25 (d, J=7.6 Hz, 1H), 8.20 (d, J=8.4 Hz, 1H), 7.84-7.80 (m, 1H), 7.67-7.63 (m, 1H), 7.59 (d, J=7.2 Hz, 1H), 7.50 (d, J=6.4 Hz, 1H), 7.46 (d, J=8.4 Hz, 1H), 3.09 (t, J=8.0 Hz, 2H), 2.33-2.29 (m, 2H).

Example 9: Synthesis of Compound 13

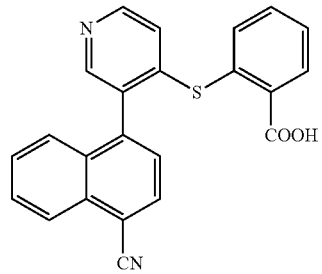 [SMILES: N#Cc1ccc(-c2cnccc2Sc2ccccc2C(=O)O)c2ccccc12]

Compound 13 was synthesized by a method similar to that in Example 5, except that methyl 2-(1-(mercaptomethyl)cyclopropyl)acetate was replaced with the corresponding compound in step 1.

LC-MS (ES, m/z): 383 [M+H]$^+$. H-NMR (300 MHz, d$_6$-DMSO, ppm): δ 7.19-7.21 (d, J=5.7 Hz, 1H), 7.45-7.56 (m, 3H), 7.67-7.72 (m, 3H), 7.83-7.90 (m, 2H), 8.22-8.30 (m, 2H), 8.60-8.62 (d, J=6.3 Hz, 2H).

Example 10: Synthesis of Compound 14

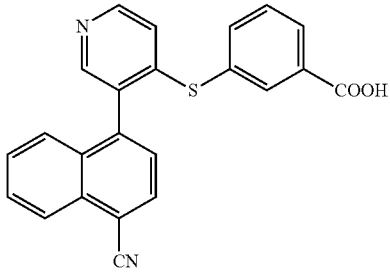 [SMILES: N#Cc1ccc(-c2cnccc2Sc2cccc(C(=O)O)c2)c2ccccc12]

Compound 14 was synthesized by a method similar to that in Example 5, except that methyl 2-(1-(mercaptomethyl)cyclopropyl)acetate was replaced with the corresponding compound in step 1.

LC-MS (ES, m/z): 383 [M+H]$^+$. H-NMR (300 MHz, d$_6$-DMSO, ppm): δ 7.02-7.04 (d, J=5.7 Hz, 1H), 7.58-7.78 (m, 5H), 7.87-7.91 (m, 2H), 8.01-8.03 (d, J=7.8 Hz, 1H), 8.24-8.27 (d, J=8.4 Hz, 1H), 8.31-8.34 (d, J=7.5 Hz, 1H), 8.54-8.57 (m, 2H).

Example 11: Synthesis of Compound 15

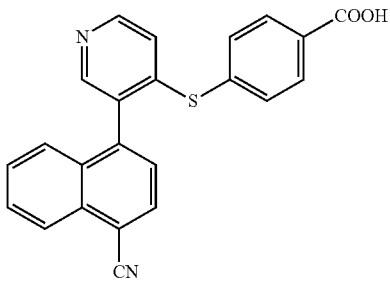 [SMILES: N#Cc1ccc(-c2cnccc2Sc2ccc(C(=O)O)cc2)c2ccccc12]

Compound 15 was synthesized by a method similar to that in Example 5, except that methyl 2-(1-(mercaptomethyl)cyclopropyl)acetate was replaced with the corresponding compound in step 1.

LC-MS (ES, m/z): 383 [M+H]$^+$. H-NMR (300 MHz, CD$_3$OD, ppm): δ 7.31-7.33 (d, J=6.3 Hz, 1H), 7.62-7.65 (d, J=8.1 Hz, 2H), 7.72-7.79 (m, 3H), 7.86-7.91 (m, 1H), 8.12-8.15 (d, J=8.4 Hz, 2H), 8.19-8.22 (d, J=7.5 Hz, 1H), 8.35-8.37 (d, J=8.4 Hz, 1H), 8.55-8.57 (d, J=6.3 Hz, 1H), 8.63 (s, 1H).

Example 12: Synthesis of Compound 20

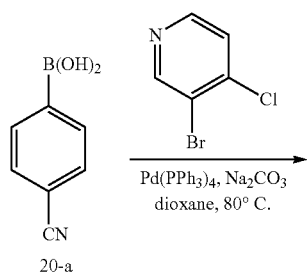

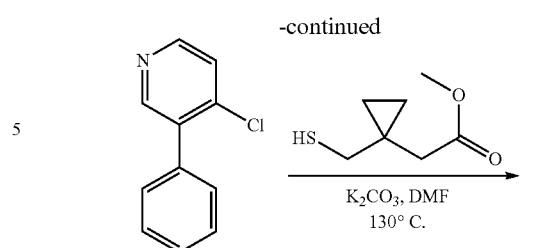

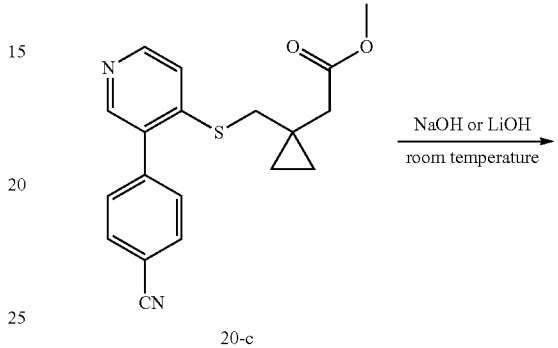

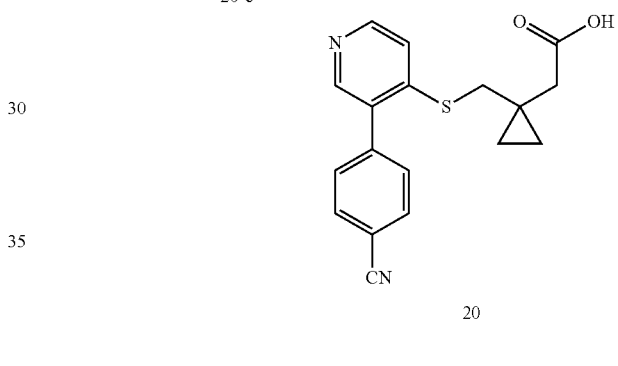

Step 1: Synthesis of 4-(4-chloropyridin-3-yl)benzonitrile (20-b)

3-bromo-4-chloropyridine (573 mg, 3 mmol), aqueous solution of sodium carbonate (6 mL, 12 mmol, 2 M), 4-cyanophenylboronic acid (441 mg, 3 mmol) and tetrakis(triphenylphosphine)palladium (0) (173 mg, 0.15 mmol) were added to dioxane (18 mL) in a single-necked flask (50 mL), and then purged with nitrogen 3 times, the mixture was heated to 80° C. and reacted for 5 hours. The reaction solution was cooled, added with ethyl acetate (100 mL), and washed with water (100 mL) and brine (100 mL). The organic phase was dried, filtered, concentrated, and purified by preparative silica gel plate (ethyl acetate/petroleum ether: 1/4) to yield a yellow solid product.

Step 2: Synthesis of methyl 2-(1-(((3-(4-cyanophenyl)pyridin-4-yl)thio)methyl)cyclopropyl)acetate (20-c)

Methyl 2-(1-(mercaptomethyl)cyclopropyl)acetate (840 mg, 5.25 mmol), potassium carbonate (1.45 g, 10.5 mmol) and 4-(4-chloropyridin-3-yl)benzonitrile (450 mg, 2.1 mmol) were dissolved in dimethyl formamide (20 mL) in a single-necked flask (50 mL), the mixture was heated to 130° C. and reacted for 0.5 hour. The reaction solution was cooled, added with ethyl acetate (100 ml), and washed with water (100 ml) and brine (100×3 mL). The organic phase was dried, filtered, concentrated, and purified by preparative silica gel plate (ethyl acetate/petroleum ether: 1/2) to yield a yellow oily product.

Step 3: Synthesis of 2-(1-(((3-(4-cyanophenyl)pyridin-4-yl)thio)methyl)cyclopropyl)acetic acid (20)

Methyl 2-(1-(((3-(4-cyanophenyl)pyridin-4-yl)thio)methyl)cyclopropyl)acetate (67 mg, 0.2 mmol) and aqueous solution of sodium hydroxide (0.5 mL, 0.5 mmol, 1 M) were added to methanol (3 mL) in a single-necked flask (50 mL), and the mixture was reacted at room temperature for 5 hours. The reaction solution was adjusted to pH=3 with concentrated hydrochloric acid, concentrated and purified by preparative reverse-phase chromatography to yield a white solid product.

LC-MS (ES, m/z): 325 [M+H]$^+$; H-NMR (400 MHz, CDCl$_3$, ppm): δ 8.42 (s, 1H), 8.24 (s, 1H), 7.75 (d, J=8.4 Hz, 2H), 7.53 (d, J=8.4 Hz, 2H), 7.35-7.33 (m, 1H), 3.19 (s, 2H), 2.38 (s, 2H), 0.62-0.60 (m, 4H).

Example 13: Synthesis of Compound 17

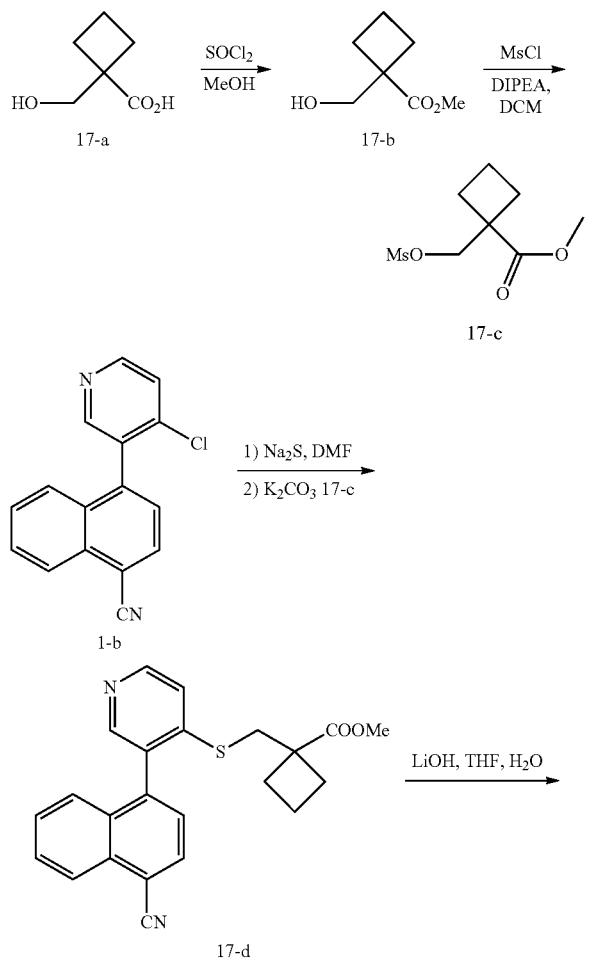

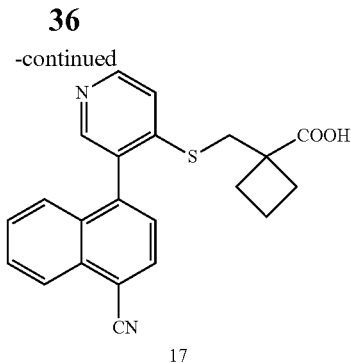

Step 1: Synthesis of methyl 1-(hydroxymethyl)cyclobutanecarboxylate (17-b)

1-(hydroxymethyl)cyclobutanecarboxylic acid (390 mg, 3 mmol) was dissolved in methanol (20 mL) in a single-necked flask (50 mL), thionyl chloride (1.7 g, 15 mmol) was added thereto at 0° C., then the mixture was stirred at 65° C. for 4 hours. The reaction solution was cooled, concentrated, and extracted by addition of ethyl acetate (50 mL), and washed with aqueous solution of sodium bicarbonate (20 mL) and brine (10 mL). The organic phase was dried, filtered and concentrated to yield a yellow oily product.

Step 2: Synthesis of methyl 1-(((methylsulfonyl)oxy)methyl)cyclobutanecarboxylate (17-c)

17-b (124 mg, 0.86 mmol) was dissolved in dichloromethane (6 mL) in a single-necked flask (50 mL), N,N-diisopropylethylamine (332 mg, 2.6 mmol) and methane sulfonyl chloride (137 mg, 1.2 mmol) were added thereto at 0° C., then the mixture was stirred at room temperature for 4 hours. The reaction solution was washed with water (20 mL) and aqueous solution of sodium bicarbonate (15 mL). The organic phase was dried, filtered and concentrated to yield a yellow oily product.

Step 3: Synthesis of methyl 1-(((3-(4-cyanonaphthalen-1-yl)pyridin-4-yl)thio)methyl)cyclobutanecarboxylate (17-d)

1-b (400 mg, 1.5 mmol) was dissolved in N,N-dimethylformamide (10 mL) in a single-necked flask (50 mL), sodium sulfide (234 mg, 4.5 mmol) was added thereto, and the mixture was reacted at 130° C. for 2 hours. The reaction solution was cooled and added with water (30 mL), after that, the reaction solution was adjusted to pH=4 with 1 N aqueous solution of hydrochloric acid, added with ethyl acetate (50 mL), then organic phase was washed with water (30 mL) and brine (30 mL). The organic phase was dried, filtered, and concentrated to yield a yellow solid product.

The above yellow solid product (100 mg, 0.38 mmol), potassium carbonate (210 mg, 1.52 mmol) and 17-c (200 mg, 0.9 mmol) were added to N,N-dimethylformamide (10 mL) in a single-necked flask (50 mL), and the mixture was reacted at 60° C. for 2 hours. The reaction solution was cooled, added with ethyl acetate (50 mL), and washed with water (30 mL) and brine (30 mL). The organic phase was dried, filtered, concentrated and purified by preparative silica gel plate (ethyl acetate/petroleum ether: 1/1) to yield a yellow solid product.

Step 4: Synthesis of 1-(((3-(4-cyanonaphthalen-1-yl)pyridin-4-yl)thio)methyl)cyclobutanecarboxylic acid (17)

17-d (64 mg, 0.165 mmol) and 1 M of aqueous solution of lithium hydroxide (0.82 mL, 0.82 mmol) were added to tetrahydrofuran (4 mL) in a single-necked flask (50 mL), and the mixture was reacted at room temperature for 36 hours. The reaction solution was adjusted to pH=4 with 1 N of hydrochloric acid, then added with ethyl acetate (50 mL), and washed with water (20 mL). The organic phase was dried, filtered, concentrated and purified by preparative silica gel plate (ethyl acetate/petroleum ether: 2/1) to yield a white solid product.

LC-MS (ES, m/z): 375 [M+H]$^+$. H-NMR (400 MHz, DMSO-d$_6$, ppm): δ 12.42 (s, 1H), 8.56 (d, J=5.2 Hz, 1H), 8.18-8.26 (m, 3H), 7.83 (m, 1H), 7.63 (m, 2H), 7.55 (d, J=7.2 Hz, 1H), 7.44 (d, J=8.8 Hz, 1H), 3.42 (s, 2H), 2.20 (m, 2H), 1.86 (m, 4H).

Example 14: Synthesis of Compound 7

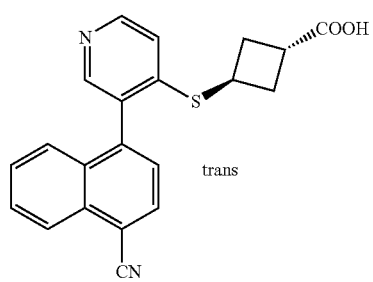 [SMILES: N#Cc1ccc(-c2cnccc2S[C@H]2C[C@H](C(=O)O)C2)c2ccccc12]

trans

Compound 7 was synthesized by a method similar to that in Example 13, except that 1-(hydroxymethyl)cyclobutanecarboxylic acid was replaced with the corresponding compound in step 1.

LC-MS (ES, m/z): 361 [M+H]$^+$. H-NMR (300 MHz, CD$_3$OD, ppm): δ 2.20-2.29 (m, 2H), 2.85-2.95 (m, 2H), 3.20-3.23 (m, 1H), 4.21-4.25 (m, 1H), 7.59-7.71 (m, 4H), 7.82-7.87 (t, J=7.5 Hz, 1H), 8.16-8.18 (d, J=7.2 Hz, 1H), 8.33-8.35 (d, J=8.4 Hz, 1H), 8.47 (m, 1H), 8.64 (m, 1H).

Example 15: Synthesis of Compound 16

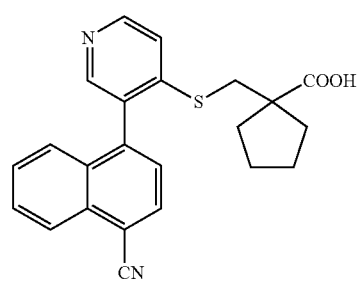 [SMILES: N#Cc1ccc(-c2cnccc2SCC2(C(=O)O)CCCC2)c2ccccc12]

Compound 16 was synthesized by a method similar to that in Example 13, except that 1-(hydroxymethyl)cyclobutanecarboxylic acid was replaced with the corresponding compound in step 1.

LC-MS (ES, m/z): 389 [M+H]$^+$. H-NMR (400 MHz, DMSO-d6, ppm): δ 8.55 (br s, 1H), 8.18-8.24 (m, 3H), 7.83 (br s, 1H), 7.55-7.59 (m, 3H), 7.44 (br s, 1H), 3.24 (br s, 2H), 1.87 (br s, 2H), 1.54-1.50 (m, 6H).

Example 16: Synthesis of Compound 11

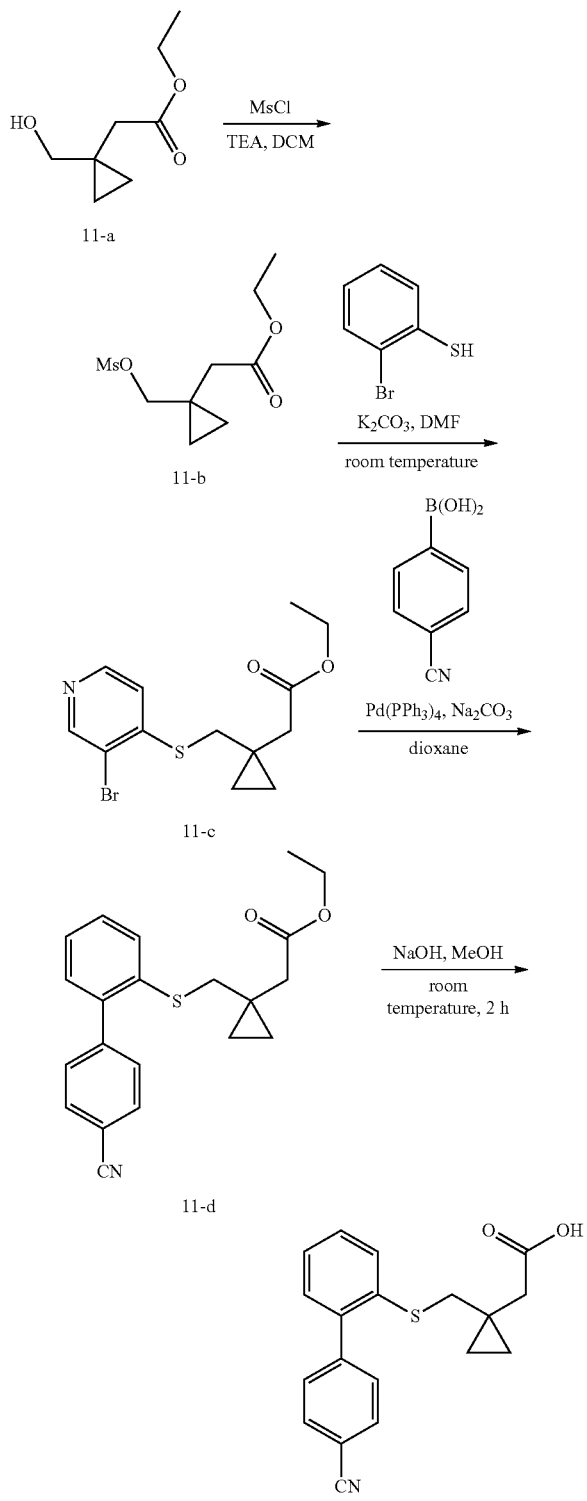

Step 1: Synthesis of (1-((ethoxycarbonyl)methyl)cyclopropyl)methyl methanesulfonate (11-b)

Ethyl 2-(1-(hydroxymethyl)cyclopropyl)acetate (288 mg, 2 mmol) and triethylamine (404 mg, 4 mmol) were dissolved in dichloromethane (3 mL) in a single-necked flask (50 mL), methanesulfonyl chloride (342 mg, 3 mmol) was added thereto under ice water bath condition, then the mixture was held at room temperature and reacted for 3 hours. Then, the reaction solution was added with ethyl acetate (50 mL), and washed with water (50 mL) and brine (50 mL). The organic phase was dried, filtered, and concentrated to yield a yellow oily product.

Step 2: Synthesis of ethyl 2-(1-((2-bromophenylthio)methyl)cyclopropyl)acetate (11-c)

(1-((ethoxycarbonyl)methyl)cyclopropyl)methyl methanesulfonate (340 mg, 1.5 mmol), anhydrous potassium carbonate (242 mg, 1.75 mmol) and 2-bromobenzenethiol (235 mg, 1.25 mmol) were dissolved in dimethyl formamide (25 mL) in a single-necked flask (50 mL), and the mixture was reacted at room temperature for 12 hours. Then, the reaction solution was added with ethyl acetate (100 ml), and washed 3 times with water (50 mL) and brine (50 mL). The organic phase was dried, filtered, concentrated, and purified by preparative silica gel plate (ethyl acetate/petroleum ether: 1/7) to yield a yellow oily product.

Step 3: Synthesis of ethyl 2-(1-((2-(4-cyanophenyl)phenylthio)methyl)cyclopropyl)acetate (11-d)

Ethyl 2-(1-((2-bromophenylthio)methyl)cyclopropyl)acetate (65 mg, 0.2 mmol), aqueous solution of sodium carbonate (0.4 mL, 0.8 mmol, 2 M), 4-cyanophenylboronic acid (30 mg, 0.2 mmol) and tetrakis(triphenylphosphine)palladium (0) (23 mg, 0.02 mmol) were added to dioxane (2 mL) in a single-necked flask (50 mL), and then purged with nitrogen 3 times, the mixture was heated to 80° C. and reacted for 4 hours. Then, the reaction solution was added with ethyl acetate (50 ml), washed with water (50 mL) and brine (50 mL). The organic phase was dried, filtered, concentrated, and purified by preparative silica gel plate (ethyl acetate/petroleum ether: 1/5) to yield a yellow oily product.

Step 4: Synthesis of 2-(1-((2-(4-cyanophenyl)phenylthio)methyl)cyclopropyl)acetic acid (compound 11)

Ethyl 2-(1-((2-(4-cyanophenyl)phenylthio)methyl)cyclopropyl)acetate (50 mg, 0.14 mmol) and aqueous solution of sodium hydroxide (1 mL, 1 mmol, 1 M) were added to methanol (3 mL) in a single-necked flask (50 mL), and the mixture was reacted at room temperature for 16 hours. Then, the reaction solution was adjusted to pH=3 with concentrated hydrochloric acid, added with ethyl acetate (50 mL), and washed with water (50 mL) and brine (50 mL). The organic phase was dried, filtered, concentrated, and purified by preparative silica gel plate (ethyl acetate/petroleum ether: 2/3) to yield a colorless oily product.

LCMS (ES, m/z): 324 [M+H]$^+$. H-NMR (400 MHz, CDCl$_3$, ppm): δ 7.72 (d, J=8.0 Hz, 2H), 7.56 (d, J=, 8.0 Hz, 2H), 7.48-7.46 (m, 1H), 7.33-7.24 (m, 2H), 7.20-7.18 (m, 1H), 2.89 (s, 2H), 2.32 (s, 2H), 0.50-0.42 (m, 4H).

Example 17: Synthesis of Compound 21

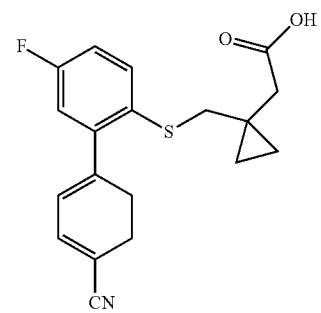 [SMILES: N#CC1=CC=C(c2cc(F)ccc2SCC2(CC(=O)O)CC2)CC1]

Compound 21 was synthesized by a method similar to that in Example 16, except that 2-bromobenzenethiol was replaced with the corresponding compound in step 2.

LC-MS (ES, m/z): 342 [M+H]$^+$; H-NMR: (400 MHz, CDCl$_3$, ppm): δ 7.73-7.70 (m, 2H), 7.55-7.50 (m, 3H), 7.06-6.95 (m, 2H), 2.79 (s, 2H), 2.28 (s, 2H), 0.45-0.37 (m, 4H).

Example 18: Synthesis of Compound 23

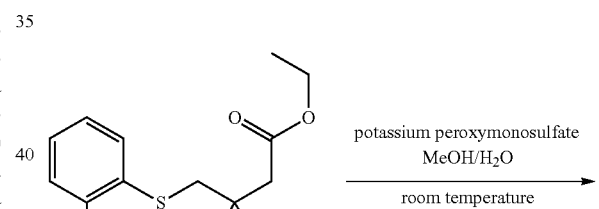

11-d

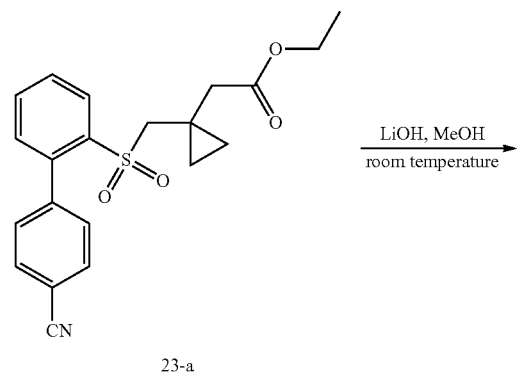

23-a

-continued

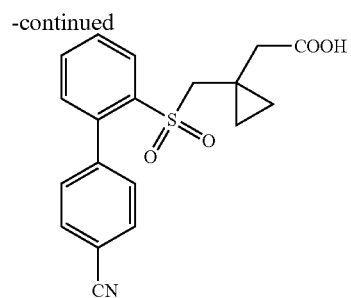

23

-continued

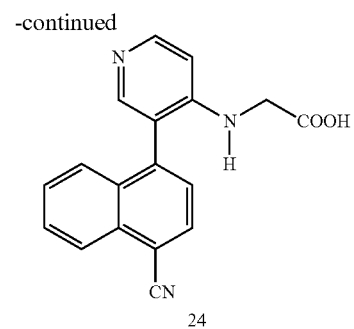

24

Step 1: Synthesis of ethyl 2-(1-((2-(4-cyanophenyl)sulfonyl)methyl)cyclopropyl)acetate (23-a)

Ethyl 2-(1-((4-cyanophenyl)phenylthio)methyl)cyclopropyl)acetate (90 mg, 0.25 mmol), and potassium monopersulfate triple salt (473 mg, 0.75 mmol) were dissolved in methanol/water (5 mL, 4/1) in a single-necked flask (50 mL), then the mixture was reacted at room temperature for 24 hours. The reaction solution was added with ethyl acetate (100 mL), washed with water (50 mL) and brine (50×3 mL). The organic phase was dried, filtered, concentrated, and purified by silica gel plate (ethyl acetate/petroleum ether: 1/2) to yield a colorless oily product.

Step 2: Synthesis of 2-(1-((2-(4-cyanophenyl)sulfonyl)methyl)cyclopropyl)acetic acid (23)

Ethyl 2-(1-((2-(4-cyanobiphenyl)sulfonyl)methyl)cyclopropyl)acetate (64 mg, 0.17 mmol), and aqueous solution of lithium hydroxide (0.4 mL, 0.4 mmol, 1 M) were added to methanol (3 mL) in a single-necked flask (50 mL), then the mixture was reacted at room temperature for 24 hours. The reaction solution was adjusted to pH=3 with concentrated hydrochloric acid and purified by preparative reverse-phase chromatography to yield a white solid product.

LC-MS (ES, m/z): 354 [M−H]−; H-NMR: (400 MHz, DMSO-$d_6$, ppm): δ 8.06 (d, J=7.6 Hz, 1H), 7.86 (d, J=8.0 Hz, 2H), 7.80-7.77 (m, 1H), 7.73-7.69 (m, 1H), 7.53 (d, J=8.4 Hz, 2H), 7.38 (d, J=7.2 Hz, 1H), 3.13 (s, 2H), 2.17 (s, 2H), 0.35-0.33 (m, 4H).

Example 19: Synthesis of 2-(3-(1-cyanonaphthalen-4-yl)pyridin-4-ylamino)acetic acid (compound 24)

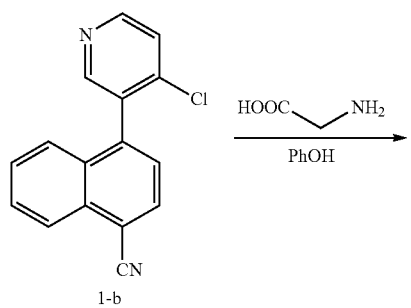

4-(4-chloropyridin-3-yl)naphtha-1-carbonitrile (53 mg, 0.2 mmol), 2-glycine (37 mg, 0.5 mmol) and phenol (113 mg, 1.2 mmol) were added in turn into a pipe sealing reaction bottle, the mixture was heated to 120 degrees and reacted overnight. Then, the reaction solution was cooled to room temperature, added with ether and filtered. Filter cake was purified by preparative reverse-phase chromatography to yield a white solid product.

LCMS (ES, m/z): 304 [M+H]+. H-NMR: (400 MHz, CD$_3$OD, ppm): δ 8.33-8.31 (m, 2H), 8.19-8.15 (m, 2H), 7.84-7.76 (m, 2H), 7.70-7.67 (m, 2H), 7.08 (d, J=7.2 Hz, 1H), 4.06 (s, 2H).

Example 20: Synthesis of Compound 25

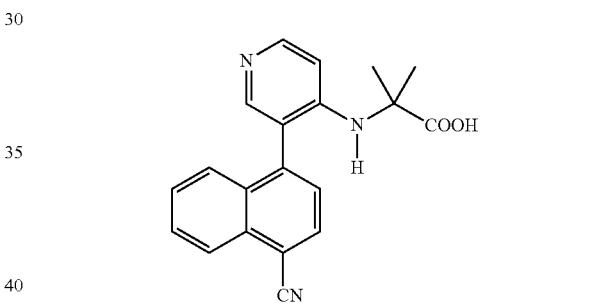

Compound 25 was synthesized by a method similar to that in Example 19, except that glycine was replaced with the corresponding compound in the step.

LC-MS (ES, m/z): 332 [M+H]+; H-NMR (400 MHz, CD$_3$OD, ppm): δ 8.19-8.13 (m, 4H), 7.85-7.67 (m, 4H), 7.17 (d, J=7.2 Hz, 1H), 1.53 (s, 3H), 1.52 (s, 3H).

Example 21: Synthesis of Compound 26

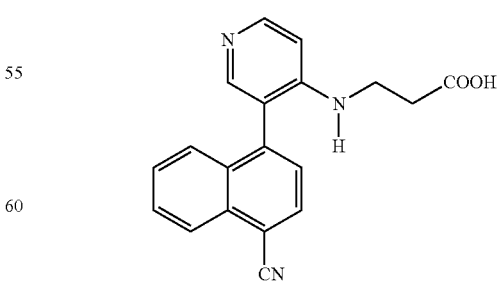

Compound 26 was synthesized by a method similar to that in Example 19, except that glycine was replaced with the corresponding compound in the step.

LC-MS (ES, m/z): 318 [M+H]+; H-NMR: (400 MHz, DMSO-d6, ppm): δ 8.23-8.17 (m, 3H), 7.90 (s, 1H), 7.83-7.79 (m, 1H), 7.65-7.62 (m, 1H), 7.57-7.52 (m, 2H), 6.75 (d, J=6.4 Hz, 1H), 5.46 (s, 1H), 3.25-3.23 (m, 2H), 2.29-2.28 (m, 2H).

Example 22: Synthesis of Compound 27

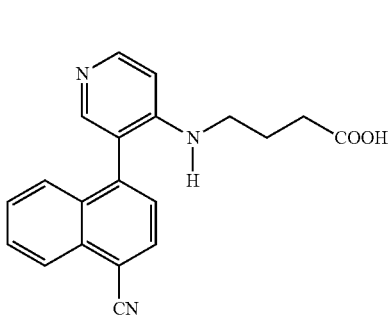 [SMILES: N#Cc1ccc(-c2cnccc2NCCCC(=O)O)c2ccccc12]

Compound 27 was synthesized by a method similar to that in Example 19, except that glycine was replaced with the corresponding compound in the step.

LC-MS (ES, m/z): 332 [M+H]+; H-NMR: (400 MHz, DMSO-d6, ppm): δ 8.20-8.17 (m, 3H), 7.88 (s, 1H), 7.83-7.79 (m, 1H), 7.65-7.62 (m, 1H), 7.57-7.53 (m, 2H), 6.73 (d, J=6.0 Hz, 1H), 5.54 (s, 1H), 3.01 (d, J=6.4 Hz, 2H), 2.10 (d, J=7.2 Hz, 2H), 1.60-1.56 (m, 2H).

Example 23: Synthesis of Compound 28

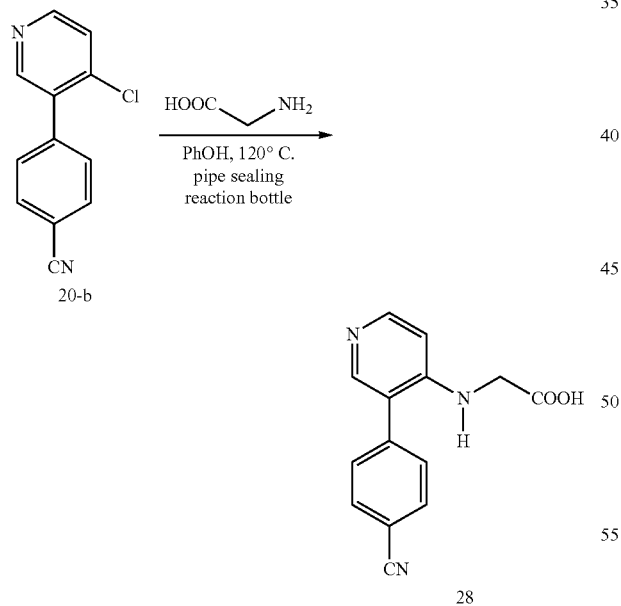

4-(4-chloropyridin-3-yl)benzonitrile (67 mg, 0.3 mmol), glycine (56 mg, 0.75 mmol) and phenol (169 mg, 1.8 mmol) were added in turn into a pipe sealing reaction bottle, the mixture was heated to 120 degrees and reacted overnight. The reaction solution was cooled to room temperature, added with ether and filtered. Filter cake was purified by preparative reverse-phase chromatography to yield a white solid product.

LCMS (ES, m/z): 254 [M+H]+; H-NMR: (400 MHz, CD3OD, ppm): δ 8.47 (br s, 2H), 8.15 (d, J=6.8 Hz, 1H), 8.00 (s, 1H), 7.90 (d, J=8.0 Hz, 1H), 7.71 (d, J=8.0 Hz, 1H), 6.80 (d, J=6.8 Hz, 1H), 3.81 (s, 2H).

Example 24: Synthesis of Compound 29

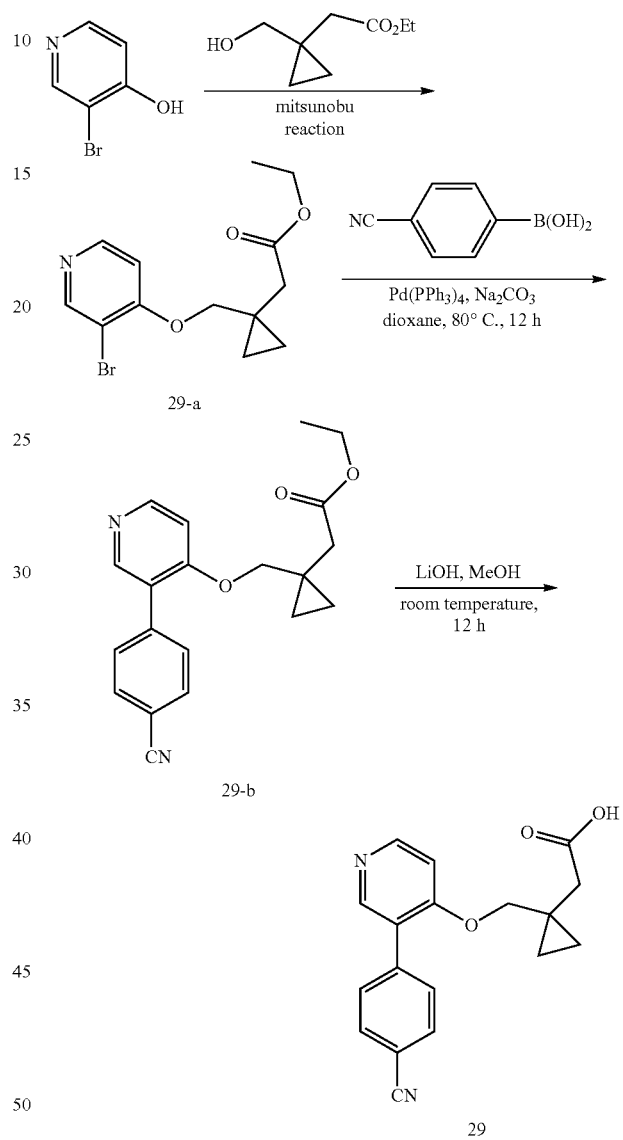

Step 1: Synthesis of ethyl 2-(1-(((3-bromopyridin-4-yl)oxy)methyl)cyclopropyl)acetate (29-a)

3-bromopyridin-4-ol (500 mg, 2.9 mmol) was dissolved in tetrahydrofuran (10 mL) in a three-necked flask (100 mL), ethyl 2-(1-(hydroxymethyl)cyclopropyl)acetate (428 mg, 2.9 mmol), triphenylphosphine (909 mg, 3.5 mmol) and diethylazodicarboxylate (609 mg, 3.5 mmol) were added thereto in turn at 0° C. under the protection of nitrogen, and then the mixture was heated to room temperature and allowed to carry out Mitsunobu Reaction for 16 hours. The reaction solution was directly concentrated, and purified by preparative silica gel plate (ethyl acetate/petroleum ether: 2/1) to yield a white solid.

Step 2: Synthesis of ethyl 2-(1-(((3-(4-cyanophenyl)pyridin-4-yl)oxy)methyl)cyclopropyl)acetate(29-b)

Ethyl 2-(1-(((3-bromopyridin-4-yl)oxy)methyl)cyclopropyl)acetate (29-a) (90 mg, 0.29 mmol), aqueous solution of sodium carbonate (1 mL, 2 mmol, 2 M), 4-cyanophenylboronic acid (43 mg, 0.29 mmol) and tetrakis(triphenylphosphine)palladium (0) (33 mg, 0.03 mmol) were added to dioxane (3 mL) in a single-necked flask (50 mL), purged with nitrogen 3 times, and then the mixture was heated to 80° C. and reacted for 12 hours. The reaction solution was cooled to room temperature, added with ethyl acetate (50 mL), and washed with water (50 mL) and brine (50 mL). The organic phase was dried, filtered, concentrated, and purified by preparative silica gel plate (dichloromethane/methanol: 20/1) to yield a yellow oily product.

Step 3: Synthesis of 2-(1-(((3-(4-cyanophenyl)pyridin-4-yl)oxy)methyl)cyclopropyl)acetic acid (29)

Ethyl 2-(1-(((3-(4-cyanophenyl)pyridin-4-yl)oxy)methyl)cyclopropyl)acetate (60 mg, 0.18 mmol) and lithium hydroxide (41 mg, 0.97 mmol) were added to tetrahydrofuran/water (3 mL/1 mL) in a single-necked flask (50 mL), and the mixture was reacted at room temperature for 16 hours. The reaction solution was adjusted to pH=4 with concentrated hydrochloric acid, added with ethyl acetate (50 mL), and washed with water (50 mL) and brine (50 mL). The organic phase was dried, filtered, concentrated, and purified by preparative silica gel plate (dichloromethane/methanol: 20/1) to yield a white solid product.

LC-MS (ES, m/z): 309 [M+H]⁺. H-NMR: (400 MHz, CDCl₃, ppm): δ 8.05 (d, J=2.0 Hz, 1H), 7.83-7.75 (m, 5H), 6.57-6.55 (m, 1H), 4.07 (s, 2H), 2.22 (s, 2H), 0.84-0.82 (m, 2H), 0.73-0.72 (m, 2H).

Example 25: Synthesis of Compound 30

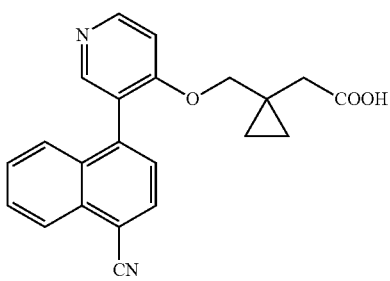 [SMILES: N#Cc1ccc(-c2cnccc2OCC2(CC(=O)O)CC2)c2ccccc12]

Compound 30 was synthesized by a method similar to that in Example 24, except that (4-cyanophenyl)boronic acid was replaced with the corresponding compound in step 2.

LC-MS (ES, m/z): 359 [M+H]⁺; H-NMR (400 MHz, CD₃OD, ppm): δ 8.22 (d, J=8.4 Hz, 1H), 8.05 (d, J=7.6 Hz, 1H), 8.02-8.00 (m, 2H), 7.82 (d, J=8.4 Hz, 1H), 7.75 (m, 1H), 7.62 (m, 1H), 7.54 (d, J=7.6 Hz, 1H), 6.61 (d, J=7.2 Hz, 1H), 4.12-4.09 (m, 2H), 2.25 (s, 2H), 0.81 (m, 2H), 0.71 (m, 2H).

Example 26: Synthesis of Compound 31

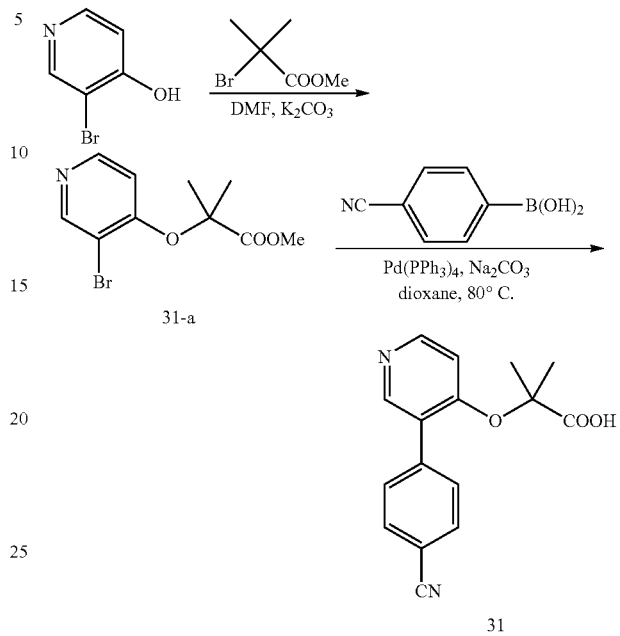

Step 1: Synthesis of methyl 2-(3-bromopyridin-4-yloxy)-2-methylpropanoate (31-a)

Methyl 2-bromo-2-methylpropanoate (724 mg, 4 mmol), potassium carbonate (828 mg, 6 mmol) and 3-bromo-4-hydroxypyridine (348 mg, 2 mmol) were dissolved in dimethyl formamide (20 mL) in a single-necked flask (50 mL), then the mixture was reacted at 60° C. for 12 hours. The reaction solution was cooled to room temperature, added with ethyl acetate (100 mL), and washed with water (50 mL) and brine (50×3 mL). The organic phase was dried, filtered, concentrated, and purified by silica gel column (dichloromethane/methanol: 50/1-20/1) to yield a colorless oily product.

Step 2: Synthesis of 2-(3-(4-cyanophenyl)pyridin-4-yloxy)-2-methylpropanoic acid (31)

Methyl 2-(3-bromopyridin-4-yloxy)-2-methylpropanoate (109 mg, 0.4 mmol), aqueous solution of sodium carbonate (0.8 mL, 1.6 mmol, 2 M), 4-cyanophenylboronic acid (59 mg, 0.4 mmol) and tetrakis(triphenylphosphine)palladium (0) (46 mg, 0.04 mmol) were added to dioxane (2.4 mL) in a single-necked flask (50 mL), purged with nitrogen 3 times, and then the mixture was heated to 80° C. and reacted for 12 hours. The reaction solution was cooled to room temperature, adjusted to pH=4, added with ethyl acetate (100 mL), and washed with water (100 mL) and brine (100 mL). The organic phase was dried, filtered, concentrated, and purified by preparative reverse-phase chromatography to yield a white solid product.

LC-MS (ES, m/z): 283 [M+H]⁺; H-NMR (400 MHz, CD₃OD, ppm): δ 8.35-8.30 (m, 2H), 7.82-7.77 (m, 4H), 6.98-6.97 (m, 1H), 1.59 (s, 6H).

Example 27: Synthesis of Compound 10

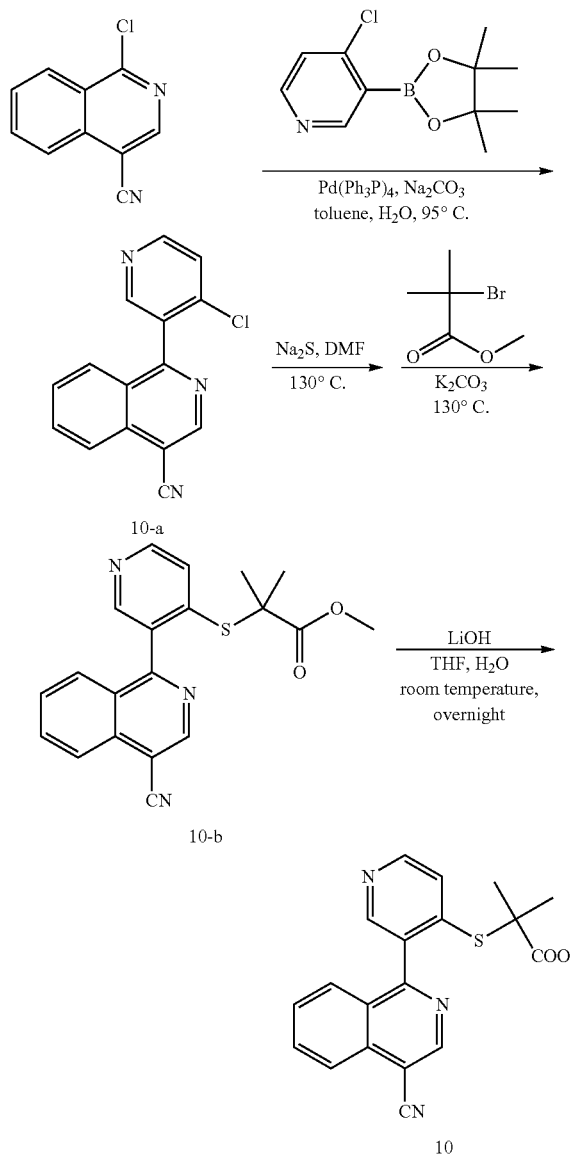

Step 1: Synthesis of 1-(4-chloropyridin-3-yl)isoquinoline-4-carbonitrile (10-a)

In a three-necked flask (100 mL), under the protection of nitrogen, 1-chloroisoquinoline-4-carbonitrile (450 mg, 2.39 mmol) was dissolved in toluene (30 mL) and water (3 mL), and 4-chloro-3-(4,4,5,5-tetramethyl-1,3,2-dioxaborolan-2-yl)pyridine (687 mg, 2.87 mmol), sodium carbonate (761 mg, 7.18 mmol) and palladium catalyst tetrakis(triphenylphosphine)palladium (0) (138 mg, 0.12 mmol) were added thereto, then the mixture was heated to 95° C. and reacted for 2 hours. The reaction solution was cooled, and the reaction was quenched by addition of 50 mL of ice water, then the reaction solution was extracted with ethyl acetate (100 mL, 3 times), reversely washed with saturated brine (100 mL, 3 times), dried over anhydrous sodium sulfate, rotary evaporated, and purified by column chromatography (petroleum ether/ethyl acetate=10:1~petroleum ether/ethyl acetate/dichloromethane=1:1:1), to yield an off-white solid product.

Step 2: Synthesis of methyl 2-((3-(4-cyanoisoquinolin-1-yl)pyridin-4-yl)thio)-2-methylpropanoate (10-b)

In a three-necked flask (100 mL), under the protection of nitrogen, 1-(4-chloropyridin-3-yl)isoquinoline-4-carbonitrile (110 mg, 0.41 mmol) obtained in step 2 was dissolved in dimethyl formamide (20 mL), the solution was then added with sodium sulfide (194 mg, 2.49 mmol), the mixture was heated to 130° C. and reacted for about 1.5 hours, then cooled to room temperature, followed by addition of anhydrous potassium carbonate (286 mg, 2.07 mmol) and then methyl 1-(bromomethyl)cyclopropanecarboxylate (224 mg, 1.24 mmol), the mixture was then heated to 130° C. and allowed to further react for about 1.5 hours until the reaction was completed. The reaction solution was cooled and poured into 50 mL of ice water to quench the reaction, then the reaction solution was extracted with ethyl acetate (50 mL, 3 times), the organic phase was dried over anhydrous sodium sulfate, rotatory evaporated, and purified through column chromatography (petroleum ether/ethyl acetate=10:1~petroleum ether/ethyl acetate/dichloromethane=1:1:1), to yield a yellow oily product.

Step 3: Synthesis of 2-((3-(4-cyanoisoquinolin-1-yl)pyridin-4-yl)thio)-2-methylpropanoic acid (compound 10)

methyl 2-((3-(4-cyanoisoquinolin-1-yl)pyridin-4-yl)thio)-2-methylpropanoate (60 mg, 0.17 mmol) obtained in step 3, lithium hydroxide (12 mg, 0.50 mmol), tetrahydrofuran (24 mL) and water (8 mL) were added into a three-necked flask (100 mL) under the protection of $N_2$, the mixture was reacted at room temperature overnight. Tetrahydrofuran was removed by concentration; aqueous phase was extracted 3 times with dichloromethane (50 mL) and collected. Then the aqueous phase was adjusted to pH=4-5 with 2 N of hydrochloric acid regulating system and extracted with dichloromethane (100 mL, 3 times); the organic phase was combined, then dried with sodium sulfate, and rotatory evaporated. The crude product was subject to high pressure to yield a white solid product.

LC-MS (ES, m/z): 350 [M+H]$^+$; H-NMR (300 MHz, CD$_3$OD, ppm): δ 1.55 (s, 6H), 7.83-7.95 (m, 3H), 8.09-8.14 (m, 1H), 8.33-8.36 (d, J=8.4 Hz, 1H), 8.67-8.74 (m, 2H), 9.09 (s, 1H).

Example 28: Synthesis of Compound 8

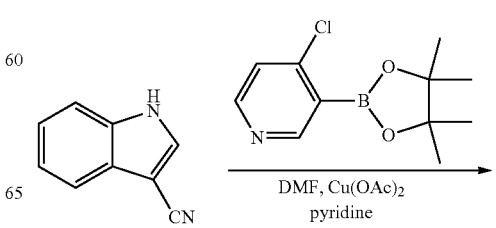

-continued

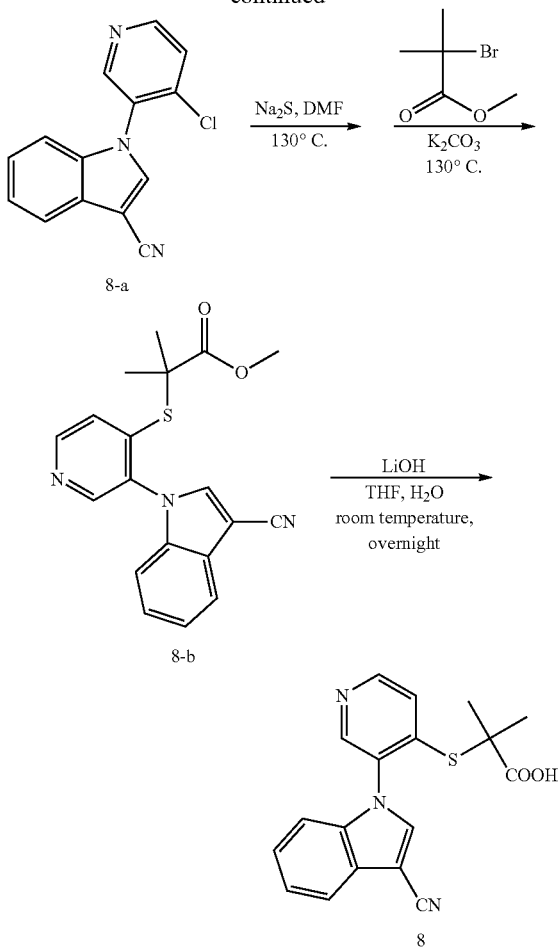

Step 1: Synthesis of 1-(4-chloropyridin-3-yl)-1H-indole-3-carbonitrile (8-a)

In a three-necked flask (100 under the protection of $N_2$, copper acetate (1800 mg, 9.9 mmol) and pyridine (1200 mg, 15.1 mmol) were sequentially added to 1H-indole-3-carbonitrile (700 mg, 4.9 mmol) and 4-chloro-3-(4,4,5,5-tetramethyl-1,3,2-dioxaborolan-2-yl)pyridine (1300 mg, 5.4 mmol) which were dissolved in dimethyl formamide (50 mL), then the mixture was stirred at room temperature. 4-chloro-3-(4,4,5,5-tetramethyl-1,3,2-dioxaborolan-2-yl) pyridine (700 mg, 3.0 mmol) was replenished every 4 hours, 5 times in total. The reaction solution was poured into 100 mL of ice water to make the reaction quenched, then the reaction solution was extracted with ethyl acetate (150 mL, 3 times) and washed with saturated brine (150 mL, 3 times). The organic phase was dried over anhydrous sodium sulfate, rotatory evaporated and subject to high pressure to yield a white solid.

Step 2: Synthesis of methyl 2-((3-(3-cyano-1H-indol-1-yl)pyridin-4-yl)thio)-2-methylpropanoate (8-b)

In a three-necked flask (100 mL), under the protection of $N_2$, 1-(4-chloropyridin-3-yl)-1H-indole-3-carbonitrile (100 mg, 0.39 mmol) obtained in step 1 was dissolved in dimethyl formamide (50 mL), then sodium sulfide (185 mg, 2.37 mmol) was added thereto, the mixture was heated to 130° C. and reacted for about 1 hour, then cooled to room temperature, followed by addition of anhydrous potassium carbonate (273 mg, 1.98 mmol) and then methyl 1-(bromomethyl) cyclopropanecarboxylate (213 mg, 1.18 mmol), the mixture was heated to 130° C. and allowed to further react for about 1.5 hour until the reaction was completed. The reaction solution was cooled and poured into 100 mL ice water, thus the reaction was quenched. The reaction solution was extracted with ethyl acetate (150 mL, 3 times), the organic phase was dried over anhydrous sodium sulfate, rotatory evaporated and subject to high pressure to yield a light yellow solid.

Step 3: Synthesis of 2-((3-(3-cyano-1H-indol-1-yl) pyridin-4-yl)thio)-2-methylpropanoic acid (compound 8)

Methyl 2-((3-(3-cyano-1H-indol-1-yl)pyridin-4-yl)thio)-2-methylpropanoate (50 mg, 0.10 mmol) obtained in step 2, lithium hydroxide (11 mg, 0.40 mmol), tetrahydrofuran (24 mL) and water (8 mL) were added into a three-necked flask (50 mL) under the protection of $N_2$, and reacted at room temperature overnight. Tetrahydrofuran was removed by concentration; aqueous phase was extracted 3 times with dichloromethane (50 mL) and collected. Then the aqueous phase was adjusted to pH=4-5 with 2N of hydrochloric acid regulating system and extracted with dichloromethane (100 mL, 3 times); the organic phase was combined, dried over sodium sulfate and then rotatory evaporated. The crude product was subject to high pressure to yield a light yellow solid.

LC-MS (ES, m/z): 338 [M+H]$^+$; H-NMR (300 MHz, CD$_3$OD, ppm): δ1.54 (s, 6H), 7.13-16 (m, 1H), 7.36-43 (m, 2H), 7.76-7.82 (m, 2H), 8.13 (s, 1H), 8.63-8.68 (m, 2H).

Example 29: Synthesis of Compound 9

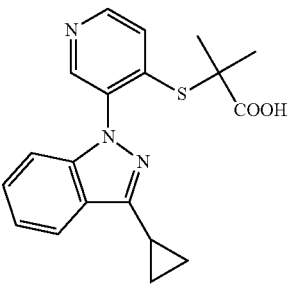 [SMILES: CC(C)(Sc1ccncc1-n1nc(C2CC2)c2ccccc21)C(=O)O]

Compound 9 was synthesized by a method similar to that in Example 28, except that 1H-indole-3-carbonitrile was replaced with the corresponding compound in step 1.

LC-MS (ES, m/z): 354 [M+H]$^+$; H-NMR (300 MHz, CD$_3$OD, ppm): δ 1.12-1.14 (m, 4H), 1.51 (s, 6H), 2.32-2.41 (m, 1H), 7.16-7.19 (d, J=8.4 Hz, 1H), 7.24-7.28 (m, 1H), 7.43-7.48 (m, 1H), 7.685 (m, 1H), 7.88-7.91 (d, J=8.1 Hz, 1H), 8.50 (br s, 2H).

Example 30: Synthesis of Compound 22

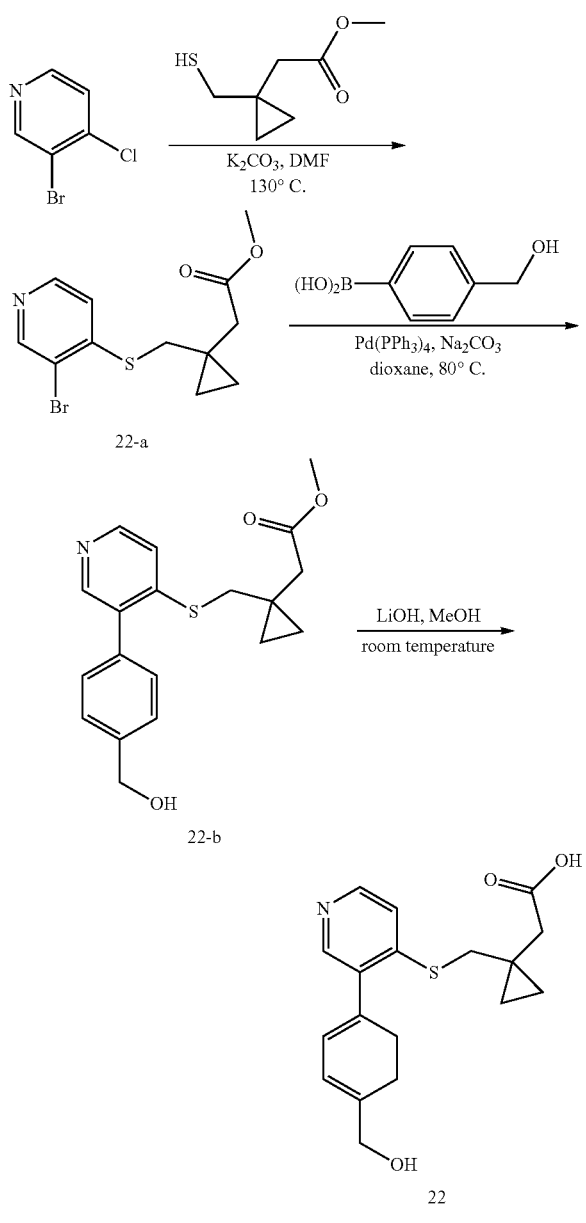

Step 1: Synthesis of methyl 2-(1-((3-bromopyridin-4-ylthio)methyl)cyclopropyl)acetate (22-a)

In a single-necked flask (50 mL), methyl 2-(1-(mercaptomethyl)cyclopropyl)acetate (2 g, 12.5 mmol), potassium carbonate (3.45 g, 25 mmol), and 3-bromo-4-chloropyridine (955 mg, 5 mmol) were dissolved in dimethyl formamide (30 mL), the mixture was heated to 130° C. and reacted for 2 hours. The reaction solution was cooled to room temperature, added with ethyl acetate (100 ml), and washed with water (100 mL) and brine (100 mL, 3 times). The organic phase was dried, filtered, concentrated and purified by silica gel column (ethyl acetate/petroleum ether: 1/10-1/6) to yield a yellow solid product.

Step 2: Synthesis of methyl 2-(1-((3-(4-(hydroxymethyl)phenylpyridin-4-yl)thio)methyl)cyclopropyl)acetate (22-b)

Methyl 2-(1-((3-bromopyridin-4-ylthio)methyl)cyclopropyl)acetate (160 mg, 0.5 mmol), aqueous solution of sodium carbonate (1 mL, 2 mmol, 2 M), 4-hydroxymethylphenylboric acid (76 mg, 0.5 mmol) and tetrakis(triphenylphosphine)palladium(0) (60 mg, 0.05 mmol) were added to dioxane (3 mL) in a single-necked flask (50 mL), purged with nitrogen 3 times, and then the mixture was heated to 80° C. and reacted for 12 hours. The reaction solution was cooled to room temperature, added with ethyl acetate (100 ml), and washed with water (100 mL) and brine (100 mL). The organic phase was dried, filtered, concentrated and purified by preparative silica gel plate (ethyl acetate/petroleum ether: 1/1) to yield a yellow solid product.

Step 3: Synthesis of 2-(1-((3-(4-(hydroxymethyl)phenyl)pyridin-4-ylthio)methyl)cyclopropyl)acetic acid (22)

In a single-necked flask (50 mL), methyl 2-(1-(((3-(4-(hydroxymethyl)phenyl)pyridin-4-yl)thio)methyl)cyclopropyl)acetate (140 mg, 0.4 mmol) and aqueous solution of aluminum hydroxide (0.8 mL, 0.8 mmol, 1 M) were added to methanol (3 mL), then the mixture was reacted at room temperature for 2 hours. The reaction solution was adjusted to pH=3 with concentrated hydrochloric acid, concentrated and purified by preparative silica gel plate (dichloromethane/methanol: 10/1) to yield a white solid product.

LC-MS (ES, m/z): 330 [M+H]$^+$; H-NMR (400 MHz, DMSO-$d_6$, ppm): δ 8.35 (d, J=6.4 Hz, 1H), 8.19 (s, 1H), 7.42-7.33 (m, 5H), 5.25 (s, 1H), 4.50 (d, J=6.4 Hz, 2H), 3.12 (s, 2H), 2.24 (s, 2H), 0.52-0.50 (m, 4H).

Example 31: Synthesis of Compound 36

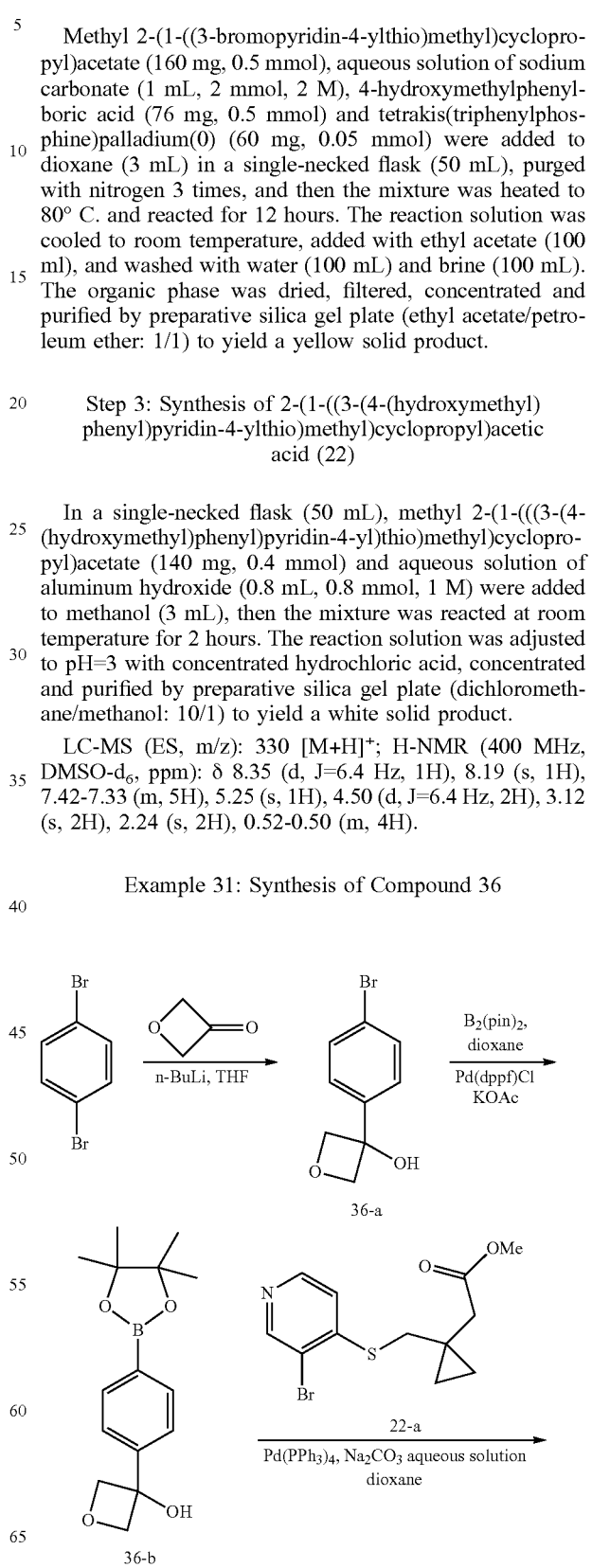

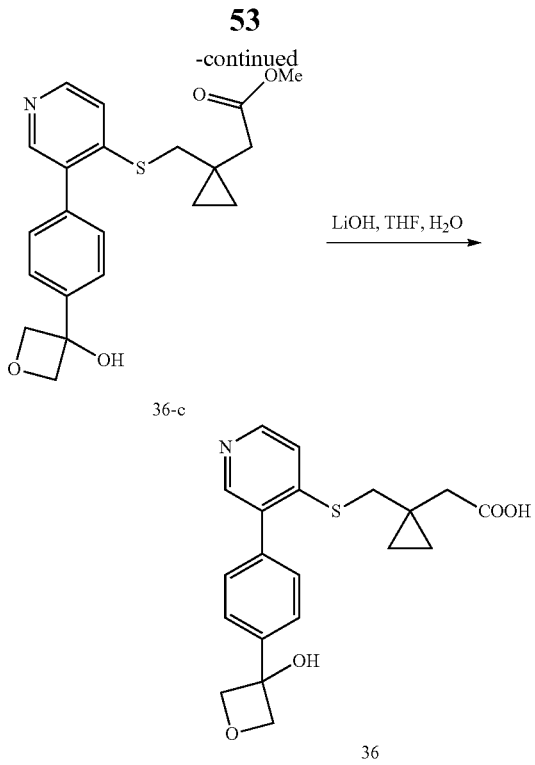

36-c

36

Step 1: Synthesis of 3-(4-bromophenyl)oxetan-3-ol (36-a)

In a three-necked flask (50 mL), under the protection of nitrogen, 1,4-dibromobenzene (600 mg, 2.55 mmol) was dissolved in tetrahydrofuran (15 mL), then the solution was cooled to 78° C. and added with n-butyllithium (1.05 mL, 2.55 mmol, 2.5 M in hexane). The mixture was reacted for 0.5 hour, then added dropwise with oxetan-3-one (153 mg, 2.55 mmol), and the resulting mixture was further reacted for 3 hours. The reaction was quenched with saturated aqueous solution of ammonium chloride (20 mL), the reaction solution was added with ethyl acetate (50 ml), then washed with brine (10 mL). The organic phase was dried, filtered, concentrated and purified by preparative silica gel plate (petroleum ether/ethyl acetate: 3/1) to yield a white solid.

Step 2: Synthesis of 3-(4-(4,4,5,5-tetramethyl-1,3,2-dioxaborolan-2-yl)phenyl)oxetan-3-ol (36-b)

36-a (300 mg, 1.2 mmol), potassium acetate (323 mg, 3.3 mmol), bis(pinacolato)diboron (B$_2$(pin)$_2$) (420 mg, 1.6 mmol), and [1,1'-bis(diphenylphosphino)ferrocene]dichloropalladium (100 mg, 0.12 mmol) were added to 1,4-dioxane (15 mL) in a single-necked flask (100 mL), purged with nitrogen 3 times, and then the mixture was heated to 90° C. and reacted for 16 hours. The reaction solution was cooled, added with ethyl acetate (60 ml), and washed with water (40 mL). The organic phase was dried, filtered, concentrated and purified by silica gel column (petroleum ether/ethyl acetate: 3/1) to yield a white solid.

Step 3: Synthesis of methyl 2-(1-(((3-(4-(3-hydroxyoxetan-3-yl)phenyl)pyridin-4-yl)thio)methyl)cyclopropyl)acetate (36-c)

36-b (150 mg, 0.54 mmol), aqueous solution of sodium carbonate (2.2 mL, 2.2 mmol, 1 M), 22-a (170 mg, 0.54 mmol), and tetrakis(triphenylphosphine)palladium(0) (62 mg, 0.054 mmol) were added to dioxane (8 mL) in a single-necked flask (100 mL), and then purged with nitrogen 3 times. The mixture was heated to 80° C. and reacted for 16 hours. The reaction solution was cooled, added with ethyl acetate (50 mL), and washed with water (40 mL). The organic phase was dried, filtered, concentrated and purified by preparative silica gel plate (petroleum ether/ethyl acetate: 1/1) to yield a white solid.

Step 4: Synthesis of 2-(1-(((3-(4-(3-hydroxyoxetan-3-yl)phenyl)pyridin-4-yl)thio)methyl)cyclopropyl) acetic acid (36)

Experimental process: In a single-necked flask (50 mL), 36-c (70 mg, 0.18 mmol) and 1 M of aqueous solution of lithium hydroxide (1 mL, 1 mmol) were added to tetrahydrofuran (3 mL), and the mixture was reacted at room temperature for 16 hours. The reaction solution was adjusted to pH=4 with 1 N of hydrochloric acid, added with chloroform-d/isopropanol (30 mL/10 mL) and washed with brine (50 mL). The organic phase was dried, filtered, concentrated and purified by preparative reverse-phase chromatography to yield a white solid product.

LC-MS (ES, m/z): 372 [M+H]$^+$; H-NMR (400 MHz, DMSO-d6, ppm): δ 8.35 (d, J=5.6 Hz, 1H), 8.20 (s, 1H), 7.68 (m, 2H), 7.43 (m, 2H), 7.35 (d, J=5.2 Hz, 1H), 6.41 (br s, 1H), 4.77 (d, J=6.4 Hz, 2H), 4.72 (d, J=6.8 Hz, 2H), 3.15 (s, 2H), 2.22 (s, 2H), 0.49 (m, 4H).

Example 32: Synthesis of Compound 35

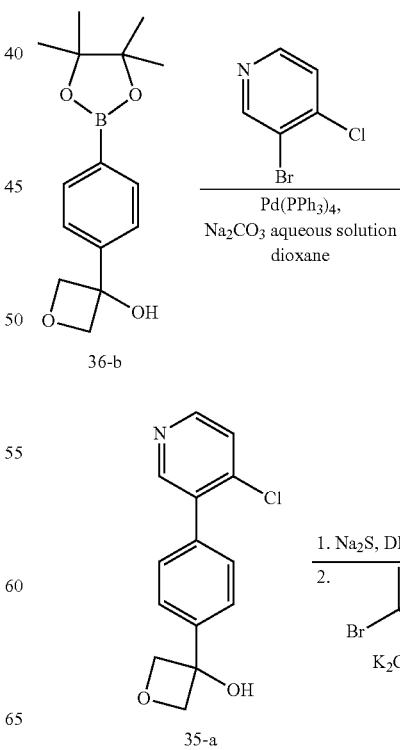

35-a

-continued

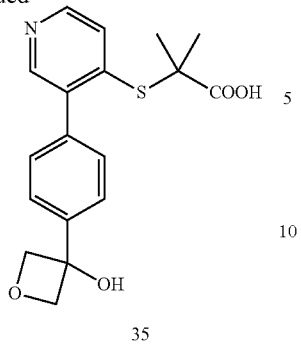

35

-continued

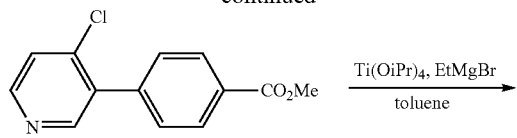

34-a

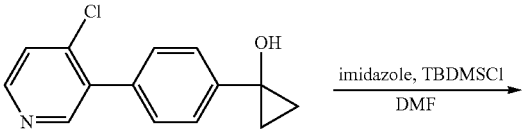

34-b

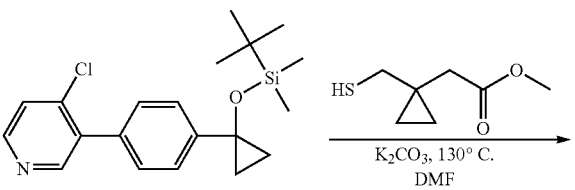

34-c

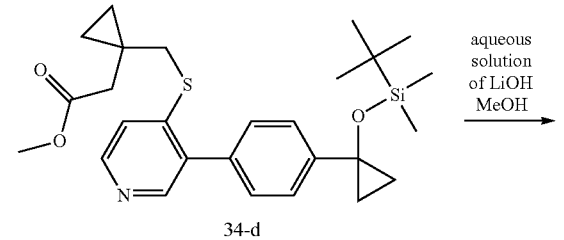

34-d

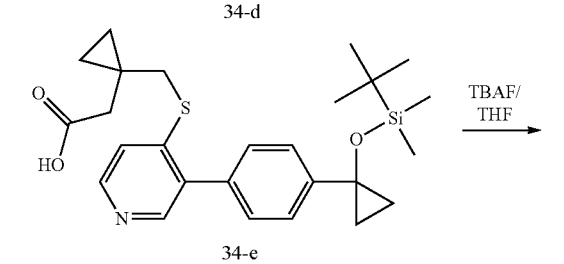

34-e

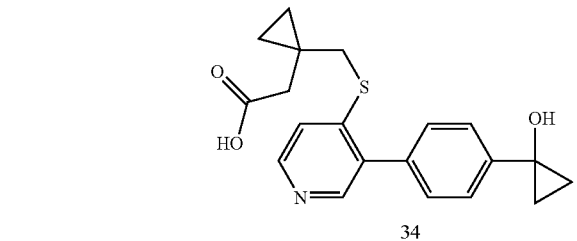

34

Step 1: Synthesis of 3-(4-(4-chloropyridin-3-yl)phenyl)oxetan-3-ol (35-a)

36-b (200 mg, 0.72 mmol), aqueous solution of sodium carbonate (1.4 mL, 2.8 mmol, 2 M), 3-bromo-4-chloropyridine (139 mg, 0.72 mmol), and tetrakis(triphenylphosphine)palladium(0) (83 mg, 0.072 mmol) were added to dioxane (6 mL) in a single-necked flask (50 mL), purged with nitrogen 3 times, and then the mixture was heated to 80° C. and reacted for 16 hours. The reaction solution was added with ethyl acetate (50 ml) and washed with water (40 mL). The organic phase was dried, filtered, concentrated and purified by preparative silica gel plate (ethyl acetate/petroleum ether: 1/1) to yield a white solid product.

Step 2: Synthesis of 2-((3-(4-(3-hydroxyoxetan-3-yl)phenyl)pyridin-4-yl)thio)-2-methylpropanoic acid (35)

In a single-necked flask (50 mL), 35-a (140 mg, 0.54 mmol) and sodium sulfide (125 mg, 1.6 mmol) were added to dimethyl formamide (6 mL), the mixture was heated to 130° C. and reacted for 1 hour. After being cooled, the reaction solution was added with anhydrous potassium carbonate (220 mg, 1.6 mmol), methyl 2-bromoisobutyrate (289 mg, 1.6 mmol), and the resulting solution was reacted for another 1 hour at 130° C. The reaction solution was added with ether (50 mL) and water (50 mL), aqueous phase was adjusted to pH=4 with dilute hydrochloric acid (1 M), then extracted by addition of chloroform-d/isopropanol (30 mL/10 mL), and washed with brine (20 mL). The organic phase was dried, filtered, concentrated and preparatively purified to yield a white solid product.

LC-MS (ES, m/z): 346 [M+H]$^+$; H-NMR (400 MHz, DMSO-d6, ppm): δ 8.40 (d, J=5.6 Hz, 1H), 8.29 (s, 1H), 7.66 (m, 2H), 7.38 (m, 3H), 6.42 (br s, 1H), 4.77 (d, J=6.4 Hz, 2H), 4.71 (d, J=6.8 Hz, 2H), 1.44 (s, 6H).

Example 33: Synthesis of Compound 34

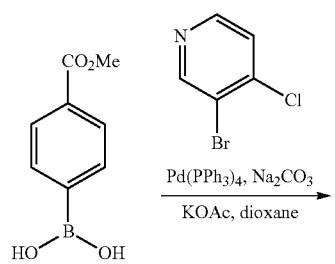

Step 1: Synthesis of methyl 4-(4-chloropyridin-3-yl)benzoate (34-a)

3-bromo-4-chloropyridine (764 mg, 4 mmol), aqueous solution of sodium carbonate (8 mL, 16 mmol, 2 M), 4-(methoxycarbonyl)phenylboronic acid (860 mg, 4 mmol), potassium acetate (392 mg, 4 mmol), and tetrakis(triphenylphosphine)palladium(0) (164 mg, 0.2 mmol) were added to dioxane (24 mL) in a single-necked flask (100 mL), purged with nitrogen 3 times, then the mixture was heated to 80° C. and reacted for 12 hours. The reaction solution was added with ethyl acetate (100 mL), and washed with water (100 mL) and brine (100 mL). The organic phase was dried, filtered, concentrated and purified by silica gel column (ethyl acetate/petroleum ether: 1/8-1/4) to yield a white solid product.

Step 2: Synthesis of 1-(4-(4-chloropyridin-3-yl)phenyl)cyclopropanol (34-b)

In a three-necked flask (50 mL), ethylmagnesium bromide (in ether (1 M), 6.8 mL, 6.8 mmol) was slowly added dropwise to the solution of 34-a (838 mg, 3.4 mmol) and titanium tetraisopropoxide (0.85 g, 3.4 mmol) in toluene (30 mL) under room temperature condition within 30 min, then the mixture was reacted for 1 hour. The reaction solution was further added with titanium tetraisopropoxide (0.85 g, 3.4 mmol) and ethylmagnesium bromide (1 M, in Et$_2$O, 6.8 mL, 6.8 mmol) and reacted for another 0.5 hour. The reaction was quenched with water, extracted with ethyl acetate (100 mL) and washed with water (100 mL) and brine (100 mL). The organic phase was dried, filtered, concentrated and purified by preparative reverse-phase chromatography to yield a white solid product.

Step 3: Synthesis of 3-(4-(1-((tert-butyldimethylsilyl)oxy)cyclopropyl)phenyl)-4-chloropyridine (34-c)

In a single-necked flask (50 mL), under ice bath condition, the solution of 34-b (150 mg, 0.6 mmol) and imidazole (204 mg, 3 mmol) in dimethyl formamide (5 mL) was added with tert-butyldimethylsilyl chloride (453 mg, 3 mmol), then the mixture was reacted at room temperature for 2 hours. The reaction solution was added with ethyl acetate (50 mL), and washed with water (50 mL) and brine (50 mL). The organic phase was dried, filtered, concentrated and purified by silica gel plate (ethyl acetate/petroleum ether: 1/4) to yield a white solid product.

Step 4: Synthesis of methyl 2-(1-(((3-(4-(1-((tert-butyldimethylsilyl)oxy)cyclopropyl)phenyl)pyridin-4-yl)thio)methyl)cyclopropyl)acetate (34-d)

In a single-necked flask (50 mL), 34-c (70 mg, 0.2 mmol), anhydrous potassium carbonate (138 mg, 1 mmol), and methyl 2-(1-(mercaptomethyl)cyclopropyl)acetate (80 mg, 0.5 mmol) were dissolved in dimethyl formamide (3 mL), the mixture was heated to 130° C. and reacted for 0.5 hour. The reaction solution was added with ethyl acetate (100 mL), and washed with water (100 mL) and brine (100×3 mL). The organic phase was dried, filtered, concentrated and purified by preparative silica gel plate (ethyl acetate/petroleum ether: 1/3) to yield a yellow oily product.

Step 5: Synthesis of 2-(1-(((3-(4-(1-(tert-butyldimethylsilyl)oxy)cyclopropyl)phenyl)pyridin-4-yl)thio)methyl)cyclopropyl)acetic acid (34-e)

In a single-necked flask (50 mL), 34-d (120 mg, 0.25 mmol) and aqueous solution of lithium hydroxide (0.75 mL, 0.75 mmol, 1 M) were added to methanol (3 mL), and reacted for 2 hours at room temperature. The reaction solution was adjusted to pH=3 with concentrated hydrochloric acid, and concentrated to dryness.

Step 6: Synthesis of 2-(1-(((3-(4-(1-hydroxycyclopropyl)phenyl)pyridin-4-yl)thio)methyl)cyclopropyl)acetic acid (34)

In a single-necked flask (50 mL), 34-e (obtained in the last step, 0.25 mmol) and tetrabutylammonium fluoride (TBAF) (0.5 mL, 0.5 mmol, 1 M) were added to tetrahydrofuran (3 mL), and reacted at room temperature for 0.5 hour. The reaction solution was added with ethyl acetate (50 mL) and washed with water (50 mL) and brine (50×3 mL). The organic phase was dried, filtered, concentrated and purified by preparative reverse-phase chromatography to yield a white solid product.

LC-MS (ES, m/z): 356 [M+H]$^+$; H-NMR (400 MHz, CD$_3$OD, ppm): δ 8.48 (d, J=6.4 Hz, 1H), 8.35 (s, 1H), 7.93 (d, J=6.8 Hz, 1H), 7.48-7.42 (m, 4H), 3.38 (s, 2H), 2.36 (s, 2H), 1.28-1.25 (m, 2H), 1.12-1.09 (m, 2H), 0.66-0.65 (m, 4H).

Example 34: Synthesis of Compound 33

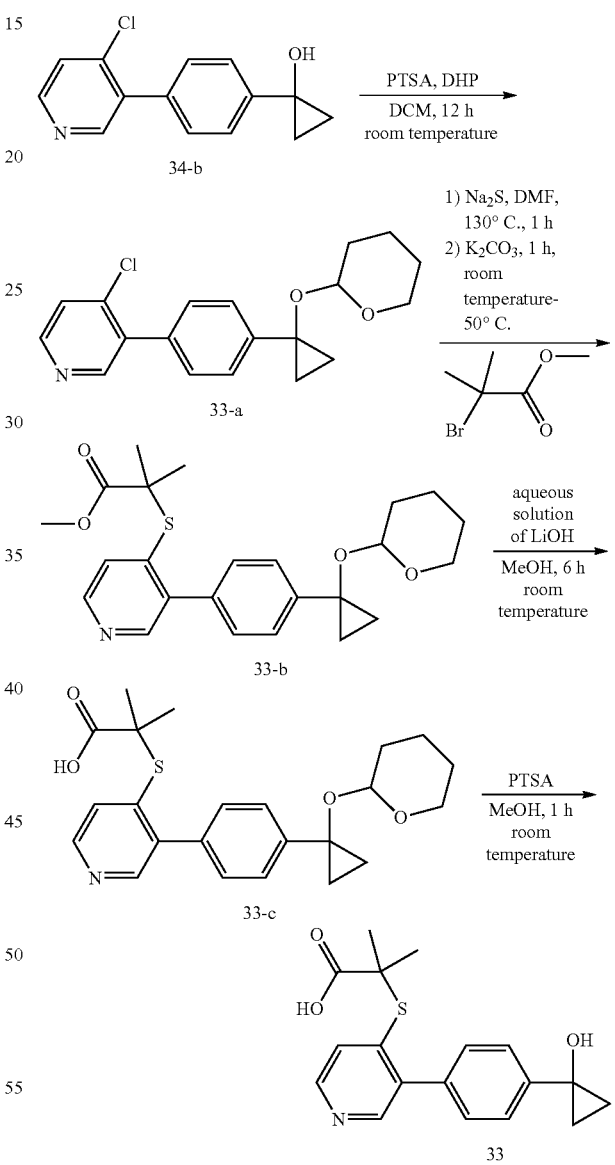

Step 1: Synthesis of 4-chloro-3-(4-(1-((tetrahydro-2H-pyran-2-yl)oxy)cyclopropyl)phenyl)pyridine (33-a)

In a single-necked flask (50 mL), the solution of 34-b (50 mg, 0.2 mmol) and p-toluene sulfonic acid (PTSA) (7 mg, 0.04 mmol) in dichloromethane (5 mL) was added with dihydropyran (DHP) (33 mg, 0.4 mmol), and the mixture was reacted at room temperature for 12 hours. The reaction solution was added with ethyl acetate (50 ml), and then washed with water (50 mL) and brine (50 mL). The organic phase was dried, filtered, concentrated and purified by silica gel plate (ethyl acetate/petroleum ether: 1/4) to yield a colorless oily product.

Step 2: Synthesis of methyl 2-methyl-2-((3-(4-(1-((tetrahydro-2H-pyran-2-yl)oxy)cyclopropyl)phenyl)pyridin-4-yl)thio)propanoate (33-b)

In a single-necked flask (50 mL), 33-a (37 mg, 0.11 mmol) and sodium sulfide (26 mg, 0.33 mmol) were dissolved in dimethyl formamide (4 mL), the mixture was heated to 130° C. and reacted for 1 hour. After being cooled, the mixture was added with anhydrous potassium carbonate (76 mg, 0.55 mmol) and methyl 2-bromoisobutyrate (60 mg, 0.33 mmol), then heated to 50° C. and the resulting mixture was allowed to further react for 1 hour. The reaction solution was added with ethyl acetate (50 mL), and washed with water (50 mL) and brine (50 mL). The organic phase was dried, filtered, concentrated and purified by preparative silica gel plate (ethyl acetate/petroleum ether: 1/3) to yield a yellow oily substance.

Step 3: Synthesis of 2-methyl-2-((3-(4-(1-((tetrahydro-2H-pyran-2-yl)oxy)cyclopropyl)phenyl)pyridin-4-yl)thio)propanoic acid (33-c)

In a single-necked flask (50 mL), 33-b (35 mg, 0.08 mmol) and the aqueous solution of lithium hydroxide (0.24 mL, 0.24 mmol, 1 M) were added to methanol (3 mL), and reacted for 6 hours at room temperature. The reaction solution was adjusted to pH=5 with concentrated hydrochloric acid, and then concentrated to yield a yellow oily substance.

Step 4: Synthesis of 2-((3-(4-(1-hydroxycyclopropyl)phenyl)pyridin-4-yl)thio)-2-methylpropanoic acid (33)

In a single-necked flask (50 mL), 33 (25 mg, 0.06 mmol) and p-toluene sulfonic acid (2 mg, 0.01 mmol) were added to methanol (3 mL), and reacted for 1 hour at room temperature. The reaction solution was added with ethyl acetate (50 ml), and washed with water (50 mL) and brine (50×3 mL). The organic phase was dried, filtered, concentrated and purified by preparative silica gel plate (dichloromethane/methanol: 8/1) to yield a light yellow solid product.

LC-MS (ES, m/z): 330 [M+H]⁺; H-NMR (400 MHz, DMSO-d6, ppm): δ 13.17 (s, 1H), 8.41 (d, J=6.4 Hz, 1H), 8.29 (s, 1H), 7.33-7.25 (m, 5H), 5.99 (s, 1H), 1.44 (s, 6H), 1.13-1.12 (m, 2H), 0.99-0.98 (m, 2H).

Example 35: Synthesis of Compound 37

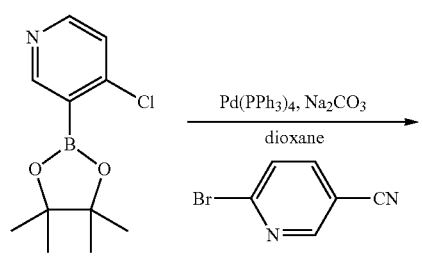

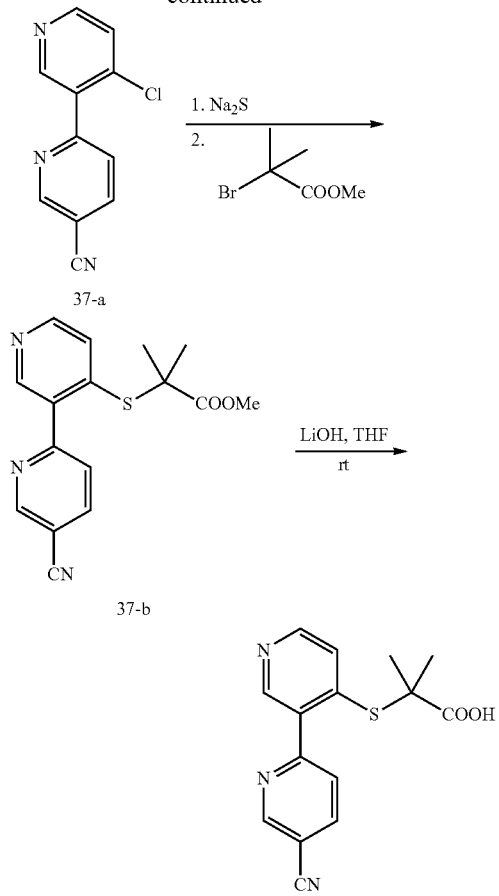

Step 1: Synthesis of 4'-chloro-[2,3'-bipyridine]-5-nitrile (37-a)

4-chloro-3-(4,4,5,5-tetramethyl-1,3,2-dioxaborolan-2-yl)pyridine (400 mg, 1.64 mmol), the aqueous solution of sodium carbonate (3.3 mL, 6.6 mmol, 2 M), 6-bromopyridin-3-carbonitrile (300 mg, 1.64 mmol) and tetrakis(triphenylphosphine)palladium (0) (180 mg, 0.16 mmol) were added to dioxane (10 mL) in a single-necked flask (50 mL), and purged with nitrogen 3 times, and then the mixture was heated to 80° C. and reacted for 5 hours. The reaction solution was added with ethyl acetate (50 mL), and washed with water (50 mL) and brine (50 mL). The organic phase was dried, filtered, concentrated and purified by preparative silica gel plate (ethyl acetate/petroleum ether: 1/3) to yield a yellow solid product.

Step 2: Synthesis of methyl 2-((5-cyano-[2,3'-bipyridine]-4'-yl)thio)-2-methylpropanoate (37-b)

In a single-necked flask (50 mL), 37-a (108 mg, 0.5 mmol) and sodium sulfide (117 mg, 1.5 mmol) were dissolved in dimethyl formamide (10 mL), the mixture was heated to 130° C. and reacted for 1 hour. After being cooled, the mixture was further added with anhydrous potassium carbonate (207 mg, 1.5 mmol) and methyl 2-bromoisobutyrate (272 mg, 1.5 mmol), and was allowed to further react for 1 hour at 130° C. The reaction solution was added with ethyl acetate (50 mL), and washed with water (50 mL) and brine (50 mL). The organic phase was dried, filtered, concentrated and purified by preparative silica gel plate (ethyl acetate/petroleum ether: 1/1) to yield a yellow oily substance.

Step 3: Synthesis of 2-((5-cyano-[2,3'-bipyridine]-4'-yl)thio)-2-methylpropanoic acid (37)

In a single-necked flask (50 mL), 37-b (60 mg, 0.19 mmol) and lithium hydroxide (41 mg, 0.97 mmol) were added to tetrahydrofuran/water (3 mL/1 mL) and reacted at room temperature for 6 hours. The reaction solution was adjusted to pH=4 with dilute hydrochloric acid (1 M), added with ethyl acetate (50 mL) and washed with water (50 mL) and brine (50 mL). The organic phase was dried, filtered, concentrated and preparatively purified to yield a white solid product.

LC-MS (ES, m/z): 300 [M+H]$^+$; H-NMR: (400 MHz, CD$_3$OD, ppm): δ 9.02 (d, J=2 Hz, 1H), 8.59 (s, 1H), 8.48 (d, J=5.2 Hz, 1H), 8.29-8.26 (m, 1H), 7.90-7.88 (m, 1H), 7.62 (d, J=5.6 Hz, 1H), 1.50 (s, 6H).

Example 36: Synthesis of Compound 19

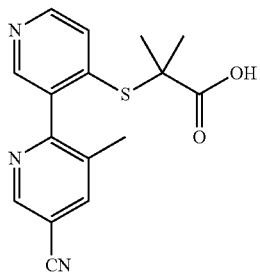 [SMILES: Cc1cc(C#N)cnc1-c1cnccc1SC(C)(C)C(=O)O]

Compound 19 was synthesized by a method similar to that in Example 35, except that 6-bromopyridin-3-carbonitrile was replaced with the corresponding compound in step 1.

LC-MS (ES, m/z): 314 [M+H]$^+$; H-NMR (400 MHz, CD$_3$OD, ppm): δ 8.81 (d, J=1.6 Hz, 1H), 8.49 (d, J=6.4 Hz, 1H), 8.31 (s, 1H), 8.18 (d, J=1.2 Hz, 1H), 7.61 (d, J=6.4 Hz, 1H), 2.22 (s, 3H), 1.53 (s, 6H).

Example 37: Synthesis of Compound 38

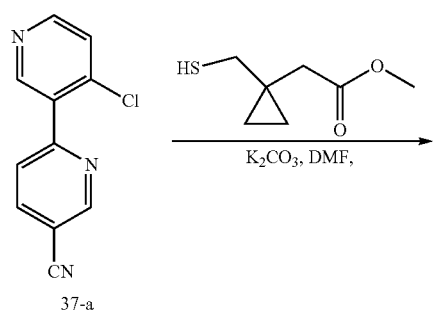

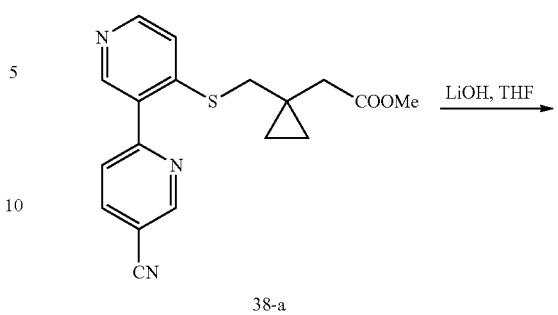

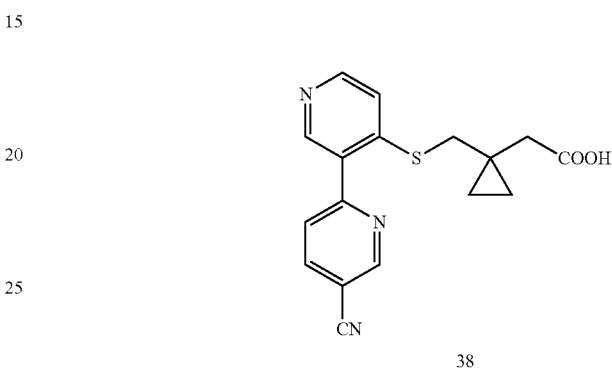

Step 1: Synthesis of methyl 2-(1-(((5-cyano-[2,3'-bipyridine]-4'-yl)thio)methyl)cyclopropyl)propionate (38-a)

In a single-necked flask (50 mL), 37-a (100 mg, 0.46 mmol) and methyl 2-(1-(mercaptomethyl)cyclopropyl)propionate (160 mg, 0.92 mmol) were dissolved in dimethyl formamide (2 mL), anhydrous potassium carbonate (256 mg, 1.84 mmol) was added thereto, and the reaction was carried out at 130° C. for 0.5 hour. The reaction solution was added with ethyl acetate (50 mL), and washed with water (50 mL) and brine (50 mL). The organic phase was dried, filtered, concentrated and purified by preparative silica gel plate (ethyl acetate/petroleum ether: 1/1) to yield a white solid.

Step 2: Synthesis of 2-(1-(((5-cyano-2,3'-bipyridin-4'-yl)thio)methyl)cyclopropyl)acetic acid (38)

In a single-necked flask (50 mL), 38-a (90 mg, 0.26 mmol) and lithium hydroxide (41 mg, 0.97 mmol) were added to tetrahydrofuran/water (3 mL/1 mL) and reacted at 0° C. for 6 hours. The reaction solution was adjusted to pH=4 with dilute hydrochloric acid (1 M), added with ethyl acetate (50 mL) and washed with water (50 mL) and brine (50 mL). The organic phase was dried, filtered, concentrated and preparatively purified to yield a white solid product.

LC-MS (ES, m/z): 326 [M+H]$^+$; H-NMR: (400 MHz, CD$_3$OD, ppm): 9.11 (d, J=1.6 Hz, 1H), 8.73 (s, 1H), 8.56 (d, J=6.0 Hz, 1H), 8.38 (dd, J=2.0 Hz, J=8.0 Hz, 1H), 8.02-8.04 (m, 2H), 3.44 (s, 2H), 2.39 (s, 2H), 0.67 (m, 4H).

Example 38: Synthesis of Compound 39

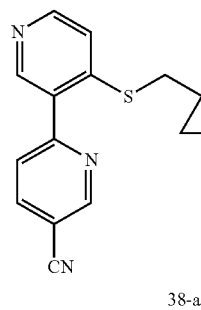

38-a

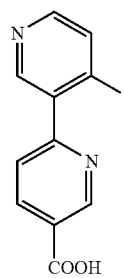

39

Step 1: Synthesis of 4'-(((1-(carboxymethyl)cyclopropyl)methyl)thio)-[2,3'-bipyridine]-5-carboxylic acid (39)

In a single-necked flask (50 mL), 38-a (40 mg, 0.12 mmol) and lithium hydroxide (15 mg, 0.36 mmol) were added to tetrahydrofuran/water (3 mL/1 mL) and reacted for 16 hours. The reaction solution was adjusted to pH=4 with dilute hydrochloric acid (1 M), added with ethyl acetate (50 mL), and washed with water (50 mL) and brine (50 mL). The organic phase was dried, filtered, concentrated and preparatively purified to yield a white solid product.

LC-MS (ES, m/z): 345.0 [M+H]$^+$; H-NMR: (400 MHz, CD$_3$OD, ppm): 9.30 (d, J=1.2 Hz, 1H), 8.72 (s, 1H), 8.55 (m, 2H), 8.04 (d, J=6.4 Hz, 1H), 7.95 (d, J=8.4 Hz, 1H), 3.45 (s, 2H), 2.39 (s, 2H), 0.67 (m, 4H).

Example 39: Synthesis of Compound 32

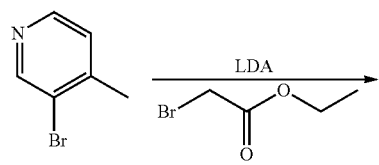

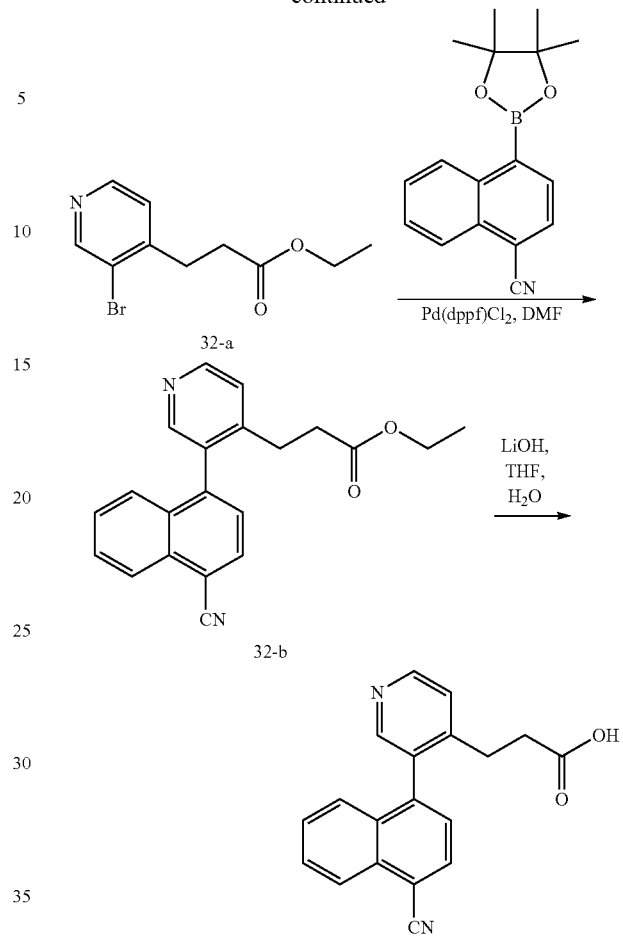

Step 1: Synthesis of ethyl 3-(3-bromopyridin-4-yl)propanoate (32-a)

In a single-necked flask (100 mL), under the protection of nitrogen, 3-bromo-4-methylpyridine (500 mg, 2.9 mmol) was dissolved in the tetrahydrofuran (10 mL), the solution was then cooled to −78° C., and added with homemade lithium diisopropylamide (LDA) (3.5 mL, 3.5 mmol), after reacted for 1 hour, ethyl 2-bromoacetate (1.22 g, 7.3 mmol) was further added dropwise thereto and reacted for another 2 hours. The reaction was quenched with saturated sodium bicarbonate solution, the reaction solution was added with ethyl acetate (50 mL), and washed with water (50 mL) and brine (50 mL). The organic phase was dried, filtered, concentrated and purified by preparative silica gel plate (petroleum ether/ethyl acetate: 2/1) to yield a yellow oily substance.

Step 2: Synthesis of ethyl 3-(3-(4-cyanonaphthalen-1-yl)pyridin-4-yl) propanoate (32-b)

32-a (100 mg, 0.39 mmol), the aqueous solution of sodium carbonate (0.8 mL, 1.6 mmol, 2 M), 4-(4,4,5,5-tetramethyl-1,3,2-dioxaborolan-2-yl)-1-cyano-naphthalene (108 mg, 0.39 mmol), and [1,1'-bis(diphenylphosphino)ferrocene]dichloropalladium (29 mg, 0.04 mmol) were added to dimethyl formamide (3 mL) in a single-necked flask (50 mL), purged with nitrogen 3 times, and then the mixture was heated to 130° C. and reacted for 5 hours. The reaction solution was added with ethyl acetate (50 mL), and washed with water (50 mL) and brine (50 mL). The organic phase was dried, filtered, concentrated and purified by preparative silica gel plate (petroleum ether/ethyl acetate: 1/1) to yield a light yellow solid.

Step 3: Synthesis of 3-(3-(4-cyanonaphthalen-1-yl) pyridin-4-yl) propanoic acid (32)

In a single-necked flask (50 mL), 32-b (30 mg, 0.1 mmol) and lithium hydroxide (41 mg, 0.97 mmol) were added to tetrahydrofuran/water (3 mL/1 mL), and the mixture was reacted at room temperature for 16 hours. The reaction solution was adjusted to pH=4 with dilute hydrochloric acid (1M), added with ethyl acetate (50 mL), and then washed with water (50 mL) and brine (50 mL). The organic phase was dried, filtered, concentrated, and preparatively purified to yield a white solid product.

LC-MS (ES, m/z): 301 [M–H]$^-$; H-NMR: (400 MHz, CD$_3$OD, ppm): δ 8.60 (d, J=5.2 Hz, 1H), 8.36 (s, 1H), 8.32-8.30 (m, 1H), 8.15-8.13 (m, 1H), 7.83-7.79 (m, 1H), 7.69-7.65 (m, 1H), 7.63-7.59 (m, 2H), 7.51-7.48 (m, 1H), 2.73-2.56 (m, 2H), 2.45-2.40 (m, 2H).

Example 40: Synthesis of Compound 40

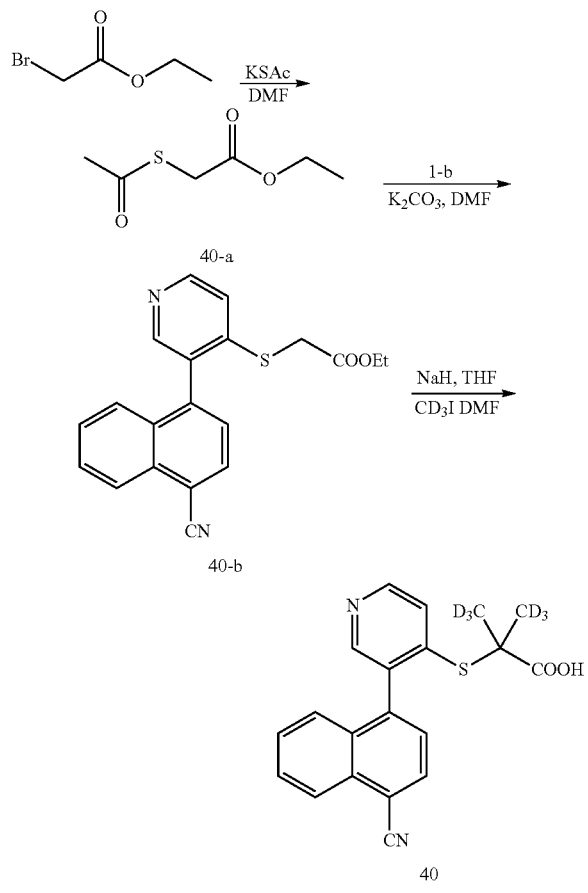

Step 1: Synthesis of ethyl 2-(acetylthio)acetate (40-a)

In a three-necked flask (250 mL), the mixture of ethyl 2-bromoacetate (4.17 g, 0.025 mol) and potassium thioacetate (5.7 g, 0.05 mol) was dissolved in dimethyl formamide (100 mL), and the resulting solution was stirred at room temperature overnight. The reaction solution was added with water and ethyl acetate, organic layer was washed with saturated brine and dried over sodium sulfate, the solvent was removed by reduced pressure evaporation, thereby a brown oily substance was obtained and directly subject to the next step for reaction.

Step 2: Synthesis of ethyl 2-((3-(4-cyanonaphthalen-1-yl)pyridin-4-yl)thio)acetate (40-b)

In a single-necked flask (100 mL), 40-a (1.46 g, 9 mmol), anhydrous potassium carbonate (1.24 g, 9 mmol) and 1-b (0.795 g, 3 mmol) were added to dimethyl formamide (20 mL), the mixture was stirred at room temperature for 1 hour, then heated to 130° C., and stirred with heating for 1 hour. After being cooled to room temperature, the reaction solution was added with water and ethyl acetate, organic layer was washed with saturated brine, dried over sodium sulfate, then the solvent was removed by reduced pressure evaporation, to give a crude brown oil, which was purified by column chromatography (petroleum ether/ethyl acetate=1:1) to yield an oil.

H-NMR: (400 MHz, CDCl$_3$, ppm): δ 8.60 (d, J=5.6 Hz, 1H), 8.35-8.33 (m, 2H), 7.99 (d, J=7.2 Hz, 1H), 7.75-7.72 (m, 1H), 7.58-7.55 (M, 2H), 7.49 (d, J=7.2 Hz, 1H), 7.36-7.34 (m, 1H), 4.20-4.16 (m, 2H), 3.63 (s, 2H), 1.26-1.24 (m, 3H).

Step 3: Synthesis of di(methyl-d3)-2-((3-(4-cyanonaphthalen-1-yl)pyridin-4-yl)thio)acetic acid (40)

In a three-necked flask (50 mL), 40-b (110 mg, 0.3 mmol) dissolved in tetrahydrofuran (1 mL) was slowly added dropwise into a suspension of sodium hydride (60%, 28 mg, 0.69 mmol) in dimethyl formamide (1 mL) at 0° C., after being stirred for 10 min, the mixture was further added dropwise with a solution of iodomethane-d3 (136 mg, 0.94 mmol) in dimethyl formamide (1 mL) at 0° C., then the mixture was stirred at room temperature overnight. After being quenched with water, the reaction solution was adjusted to pH=4 with 1 N of hydrochloric acid, then the solvent was removed by reduced pressure evaporation, and the remaining oil was purified by preparative HPLC to yield a light yellow solid.

LC-MS (ES, m/z): 355 [M+H]$^+$; H-NMR: (400 MHz, CD$_3$OD, ppm): δ 8.52-8.50 (m, 1H), 8.30-8.27 (m, 2H), 8.12-8.09 (m, 1H), 7.82-7.77 (m, 1H), 7.68-7.60 (m, 2H), 7.55-7.48 (m, 2H).

Example 41: Synthesis of Compound 41

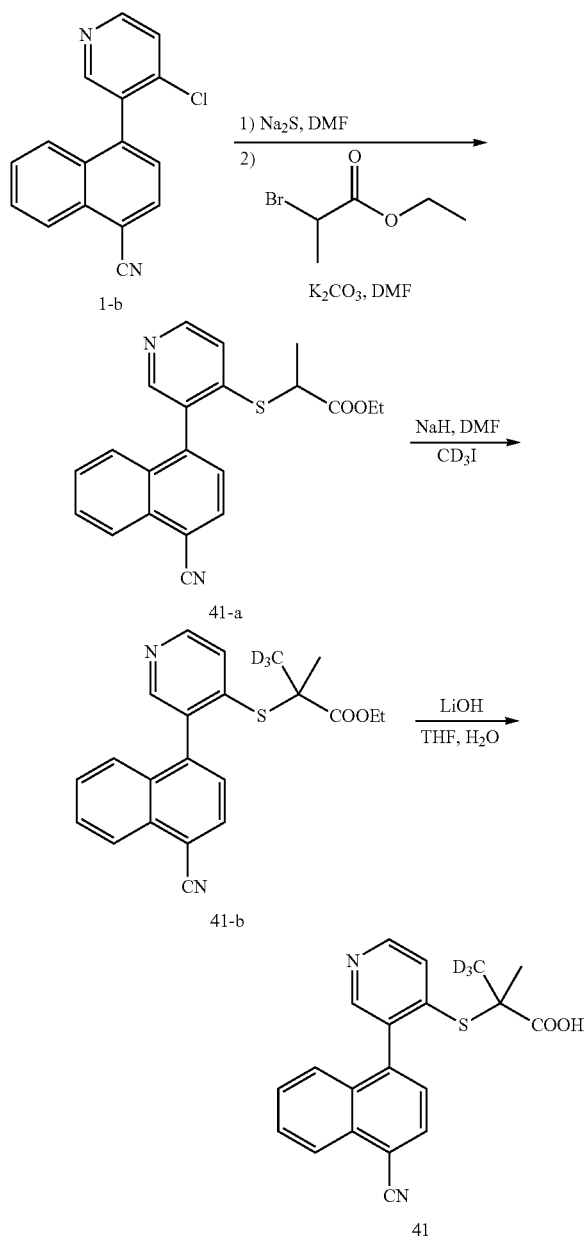

Step 1: Synthesis of ethyl 2-((3-(4-cyanonaphthalen-1-yl)pyridin-4-yl)thio)propanoate (41-a)

In a single-necked flask (50 mL), 1-b (264 mg, 1 mmol) and sodium sulfide (234 mg, 3 mmol) were added to dimethyl formamide (10 mL), the mixture was heated to 130° C. and reacted for 1 hour. After being cooled, the mixture was further added with hydrous potassium carbonate (414 mg, 3 mmol) and ethyl 2-bromoacetate (716 mg, 4 mmol), then heated to 130° C. and was allowed to further react for 1 hour. After being cooled, the reaction solution was added with ethyl acetate (50 mL), and washed with water (50 mL) and brine (50 mL). The organic phase was dried, filtered, concentrated and purified by preparative silica gel plate (ethyl acetate/petroleum ether: 1/2) to yield a white solid product.

H-NMR: (400 MHz, d6-DMSO, ppm): δ 8.61 (dd, J=2.0 Hz, J=5.2 Hz, 1H), 8.34 (d, J=5.6 Hz, 1H), 8.33-8.25 (m, 1H), 8.22 (d, J=8.4 Hz, 1H), 7.85-7.84 (m, 1H), 7.66-7.63 (m, 1H), 7.63 (d, J=6.4 Hz, 1H), 7.58 (dd, J=3.2 Hz, J=7.6 Hz, 1H), 7.44-7.41 (m, 1H), 4.44-4.39 (m, 1H), 4.07-4.02 (m, 2H), 1.32-1.30 (m, 3H), 1.10-1.06 (m, 3H).

Step 2: Synthesis of ethyl 2-methyl-d3-2-((3-(4-cyanonaphthalen-1-yl)pyridin-4-yl)thio)propanoate (41-b)

In a three-necked flask (100 mL), under the protection of nitrogen, sodium hydride (16 mg, in oil (60%), 0.4 mmol) was added to dimethyl formamide (5 mL), the mixture was then cooled to 0° C., and a solution of 41-a (120 mg, 0.33 mmol) in tetrahydrofuran (2.5 mL) was added thereto. The mixture was reacted at 0° C. for 0.5 hour, the reaction solution was further added dropwise with a solution of iodomethane-d3(58 mg, 0.4 mmol) in dimethyl formamide (1.5 mL), then heated to room temperature and reacted for another 16 hours. The reaction solution was added with ethyl acetate (50 mL), and washed with water (20 mL) and brine (10 mL). The organic phase was dried, filtered, concentrated and purified by preparative silica gel plate (ethyl acetate/petroleum ether: 1/2) to yield a white solid product.

H-NMR: (400 MHz, d6-DMSO, ppm): δ 8.64 (d, J=5.2 Hz, 1H), 8.41 (s, 1H), 8.28 (d, J=7.2 Hz, 1H), 8.22 (d, J=8.4 Hz, 1H), 7.83 (t, J=7.6 Hz, 1H), 7.69 (t, J=7.6 Hz, 1H), 7.57 (d, J=7.2 Hz, 1H), 7.42-7.38 (m, 2H), 4.08 (q, J=7.2 Hz, 2H), 1.37 (d, J=3.2 Hz, 3H), 1.10 (t, J=7.2 Hz, 3H).

Step 3: Synthesis of 2-methyl-d3-2-((3-(4-cyanonaphthalen-1-yl)pyridin-4-yl)thio) propanoic acid (41)

In a single-necked flask (50 mL), 41-b (60 mg, 0.16 mmol) and lithium hydroxide (41 mg, 0.97 mmol) were added to tetrahydrofuran/water (3 mL/1 mL) and reacted at room temperature for 12 hours. The reaction solution was adjusted to pH=4 with dilute hydrochloric acid (1 M), added with ethyl acetate (30 mL), and washed with brine (20 mL). The organic phase was dried, filtered, concentrated and preparatively purified to yield a white solid product.

LC-MS (ES, m/z): 352 [M−H]−; H-NMR: (400 MHz, d6-DMSO, ppm): δ 13.18 (br, 1H), 8.61 (d, J=5.2 Hz, 1H), 8.36 (s, 1H), 8.26 (d, J=7.2 Hz, 1H), 8.21 (d, J=8.4 Hz, 1H), 7.83 (t, J=7.6 Hz, 1H), 7.66 (t, J=7.6 Hz, 1H), 7.57 (d, J=7.2 Hz, 1H), 77.51 (d, J=5.2 Hz, 1H), 7.41 (d, J=8.4 Hz, 1H), 1.37 (d, J=10.8 Hz, 3H).

Experimental Example 1: Evaluation of Bioactivity of Chemicals for Inhibiting Absorption of Uric Acid Using URAT1 Cell Model Human kidney embryonic cells HEK-293T were grown in a petri dish (diameter=10 cm) containing DMEM and 10% of bovine fetal serum culture solution, and incubated in an 5% of carbon dioxide-containing incubator at 37° C. Plasmids carrying human URAT1 were transfected to HEK-293T cells using TransIT-293 (Mirus Bio LLC). After 72 hours, the petri dish containing HEK-293T cells transfected with URAT1 was removed from the incubator and the cells were inoculated on Poly-D-Lysine Coated 96-well Plates at a density of 60,000 cells per well. After the cells on the 96-well plates were grown overnight (at least 12 hours) in an incubator at 37 degrees, these cells were gently rinsed 3 times with warm and no chloride ions-containing HBSS buffer (125 mM sodium gluconate, 4.8 mM potassium gluconate, 1.3 mM calcium gluconate, 1.2 mM monopotassium phosphate, 1.2 mM magnesium sulfate, 5.6 mM glucose, 25 mM HEPES, pH 7.4). 50 microliter of HBSS buffer (not containing chloride ions) containing 0.2 microcurie of $^{14}$C-uric acid and compounds of the present application or benzbromarone, and vector was added in each well, then the cell plates were put back to the incubator at 37 degrees. After 5 min, the buffer was removed from cell wells, added with 100 microliter of ice-cold and no chloride ions-containing HBSS buffer to gently rinse cells within wells so as to stop them from absorbing $^{14}$C-uric acid, the rinsing was repeated 3 times in the same manner. 150 microliter of cell lysate (100 mM of NaOH) was added in each well. Cell plate was placed on a vibrating plate and vibrated for 10 min at a speed of 600 rpm such that the cells were completely lysed. The cell plate was put in a centrifuge and spun for 5 min at a speed of 1000 rpm, then 45 microliter of supernatant was sucked out from each well and transferred to 96-well plate (Isoplate-96 Microplate from PerkinElmer). In the new 96-well plate, 150 microliter of Ultima Gold XR scintillation solution was added in each well. The 96-well plate was vibrated for 10 min at a speed of 600 rpm on a vibrating plate. Finally, the 96-well plate was put in a MicroBeta Trilux Counter from PerkinElmer and was read, then IC$_{50}$ values were calculated, and the results are shown in Table 1 below. Wherein

TABLE 1

| Compound No. | URAT1 IC$_{50}$ Activity level |
|---|---|
| 1 | I |
| 2 | II |
| 3 | I |
| 4 | I |
| 5 | II |
| 6 | III |
| 7 | II |
| 8 | III |
| 9 | III |
| 10 | III |
| 11 | I |
| 12 | II |
| 13 | II |
| 14 | II |
| 15 | II |
| 16 | I |
| 17 | I |
| 18 | I |
| 19 | III |
| 20 | I |
| 21 | I |
| 22 | II |
| 23 | III |
| 24 | III |
| 25 | III |
| 26 | III |
| 27 | III |
| 28 | III |
| 29 | III |
| 30 | III |
| 31 | III |
| 32 | III |
| 33 | II |
| 34 | II |
| 35 | II |
| 36 | III |
| 37 | III |
| 38 | III |
| 39 | III |

TABLE 1-continued

| Compound No. | URAT1 IC$_{50}$ Activity level |
|---|---|
| 40 | I |
| 41 | I |
| benzbromarone | II |

I represents that IC$_{50}$ value is in the range of less than or equal to 100 nM;

II represents that IC$_{50}$ value is in the range of less than or equal to 1000 nM and more than 100 nM; and III represents that IC$_{50}$ value is more than 1000 nM.

From the experimental data listed in the above Table 1, it can be seen that, compared with existing compound benzbromarone, the compounds of the present invention have lower or similar IC$_{50}$ values, thereby it is demonstrated that the compounds of the present invention have higher activities of inhibiting the reabsorption of uric acid, and can be used as novel and efficient drugs for reducing blood uric acid.

The examples and embodiments disclosed herein are merely for the illustrative purpose, and various amendments and modifications made by a person skilled in the art will be included in the spirit and scope of the present application and are within the scope of the appended claims.

The invention claimed is:

1. A compound selected from the group consisting of

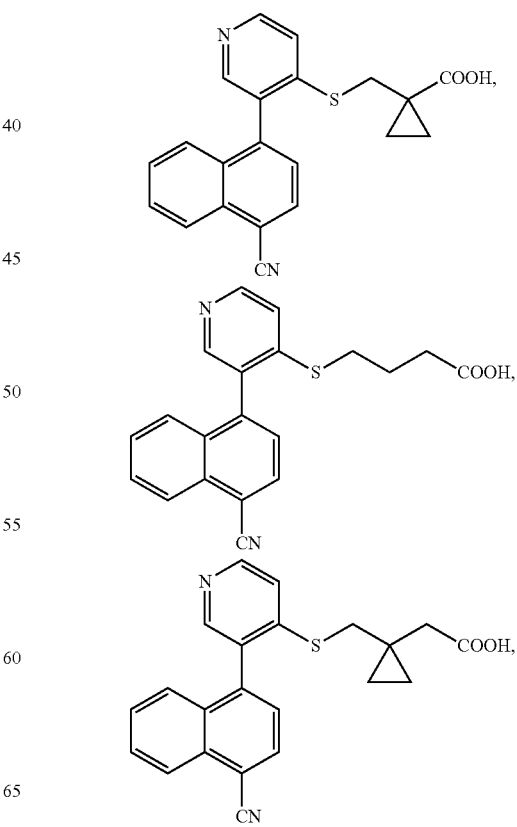

-continued

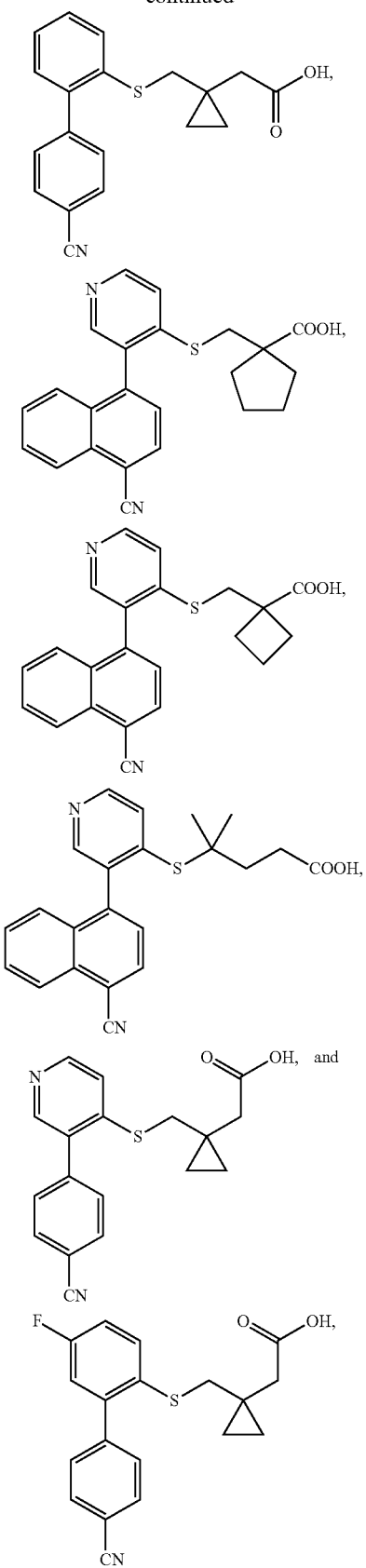

or a pharmaceutically acceptable salt thereof.

2. The compound of claim 1, which is

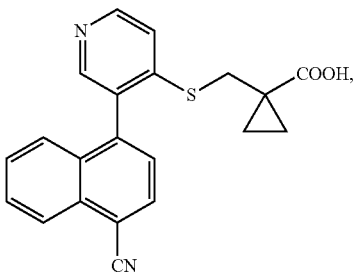 [SMILES: N#Cc1ccc(-c2cnccc2SCC2(C(=O)O)CC2)c2ccccc12]

or a pharmaceutically acceptable salt thereof.

3. The compound of claim 1, which is

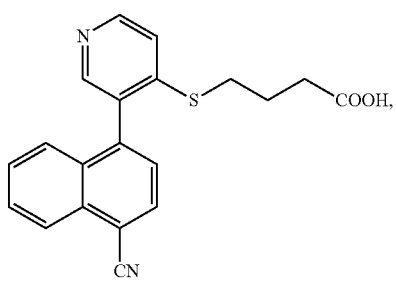 [SMILES: N#Cc1ccc(-c2cnccc2SCCCC(=O)O)c2ccccc12]

or a pharmaceutically acceptable salt thereof.

4. The compound of claim 1, which is

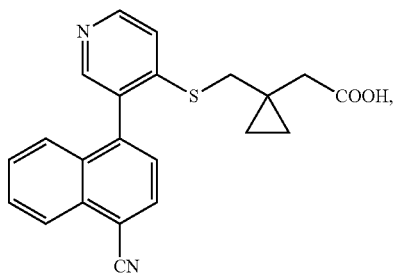 [SMILES: N#Cc1ccc(-c2cnccc2SCC2(CC(=O)O)CC2)c2ccccc12]

or a pharmaceutically acceptable salt thereof.

5. The compound of claim 1, which is

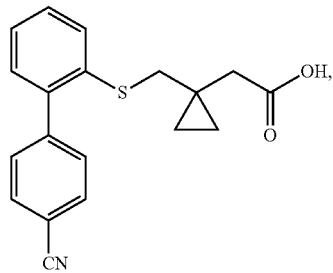 [SMILES: N#Cc1ccc(-c2ccccc2SCC2(CC(=O)O)CC2)cc1]

or a pharmaceutically acceptable salt thereof.

6. The compound of claim 1, which is

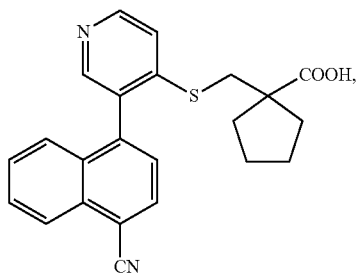 [SMILES: N#Cc1ccc(-c2cnccc2SCC2(C(=O)O)CCCC2)c2ccccc12]

or a pharmaceutically acceptable salt thereof.

7. The compound of claim 1, which is

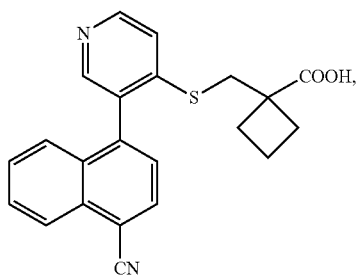 [SMILES: N#Cc1ccc(-c2cnccc2SCC2(C(=O)O)CCC2)c2ccccc12]

or a pharmaceutically acceptable salt thereof.

8. The compound of claim 1, which is

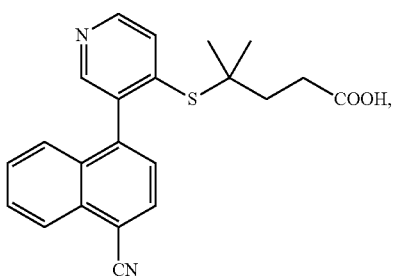 [SMILES: CC(C)(CCC(=O)O)Sc1ccncc1-c1ccc(C#N)c2ccccc12]

or a pharmaceutically acceptable salt thereof.

9. The compound of claim 1, which is

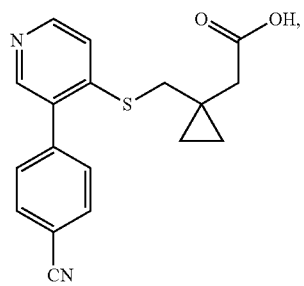 [SMILES: N#Cc1ccc(-c2cnccc2SCC2(CC(=O)O)CC2)cc1]

or a pharmaceutically acceptable salt thereof.

10. The compound of claim 1, which is

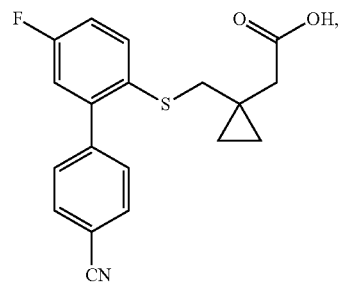 [SMILES: N#Cc1ccc(-c2cc(F)ccc2SCC2(CC(=O)O)CC2)cc1]

or a pharmaceutically acceptable salt thereof.

11. A pharmaceutical composition comprising the carboxylic acid compound according to claim 1, or a pharmaceutically acceptable salt thereof, and a pharmaceutically acceptable carrier.

12. A method of treating gout in a human, comprising administering to the human an effective amount of a compound selected from the group consisting of

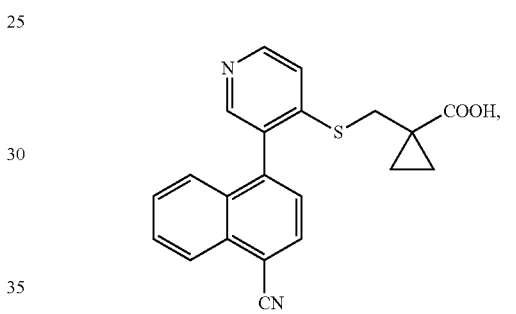

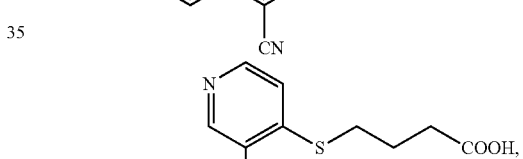

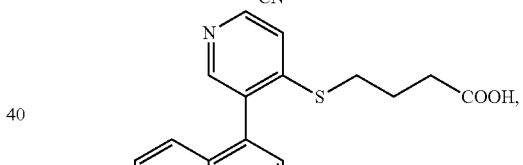

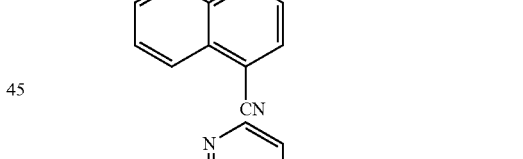

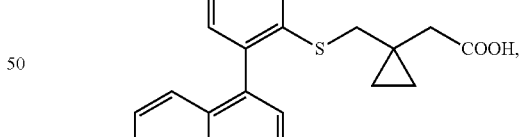

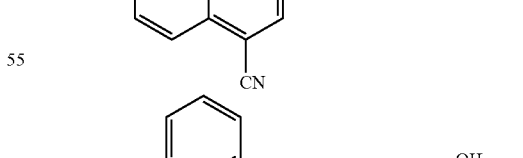

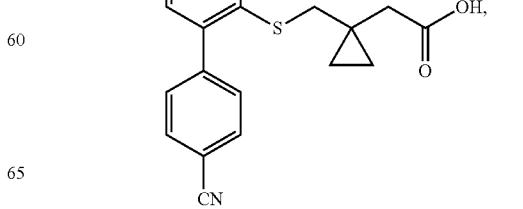

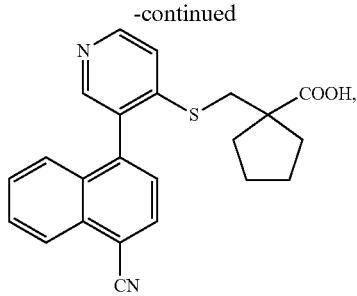

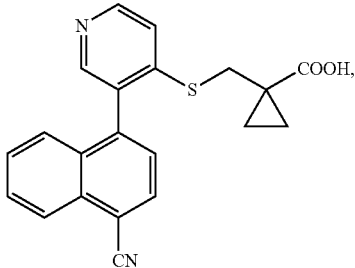 [SMILES: N#Cc1ccc(-c2cnccc2SCC2(C(=O)O)CC2)c2ccccc12]

or a pharmaceutically acceptable salt thereof.

14. The method of claim 12, comprising administering to the human an effective amount of compound

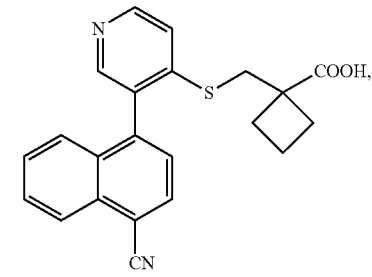

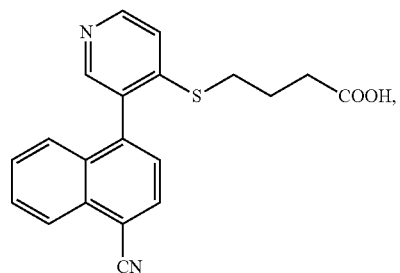 [SMILES: N#Cc1ccc(-c2cnccc2SCCCC(=O)O)c2ccccc12]

or a pharmaceutically acceptable salt thereof.

15. The method of claim 12, comprising administering to the human an effective amount of compound

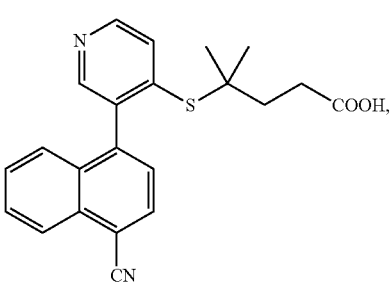

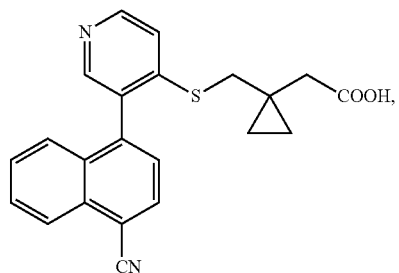 [SMILES: N#Cc1ccc(-c2cnccc2SCC2(CC(=O)O)CC2)c2ccccc12]

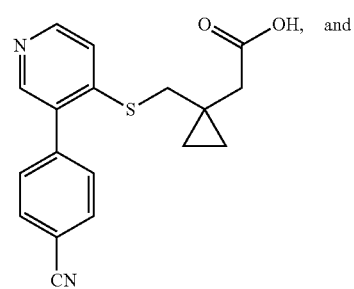 and or a pharmaceutically acceptable salt thereof.

16. The method of claim 12, comprising administering to the human an effective amount of compound

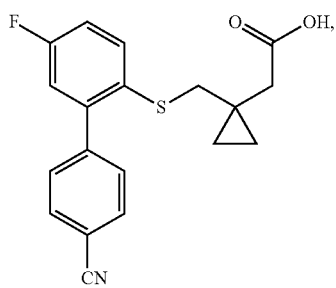

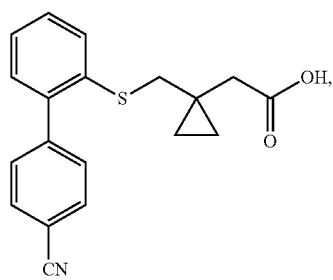 [SMILES: N#Cc1ccc(-c2ccccc2SCC2(CC(=O)O)CC2)cc1]

or a pharmaceutically acceptable salt thereof.

13. The method of claim 12, comprising administering to the human an effective amount of compound or a pharmaceutically acceptable salt thereof.

17. The method of claim 12, comprising administering to the human an effective amount of compound

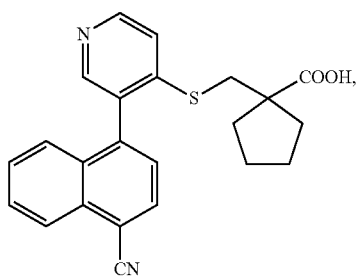 [SMILES: N#Cc1ccc(-c2cnccc2SCC2(C(=O)O)CCCC2)c2ccccc12]

or a pharmaceutically acceptable salt thereof.

18. The method of claim 12, comprising administering to the human an effective amount of compound

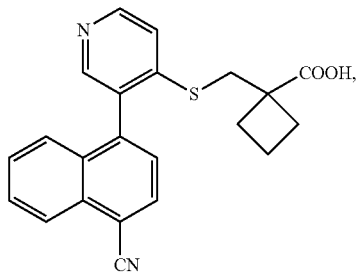 [SMILES: N#Cc1ccc(-c2cnccc2SCC2(C(=O)O)CCC2)c2ccccc12]

or a pharmaceutically acceptable salt thereof.

19. The method of claim 12, comprising administering to the human an effective amount of compound

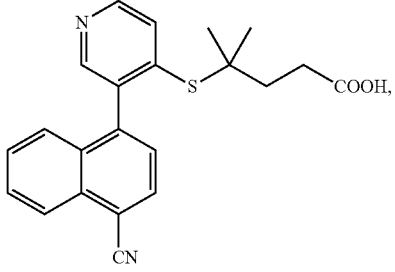 [SMILES: CC(C)(CCC(=O)O)Sc1ccncc1-c1ccc(C#N)c2ccccc12]

or a pharmaceutically acceptable salt thereof.

20. The method of claim 12, comprising administering to the human an effective amount of compound

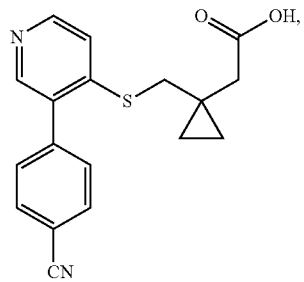 [SMILES: N#Cc1ccc(-c2cnccc2SCC2(CC(=O)O)CC2)cc1]

or a pharmaceutically acceptable salt thereof.

21. The method of claim 12, comprising administering to the human an effective amount of compound

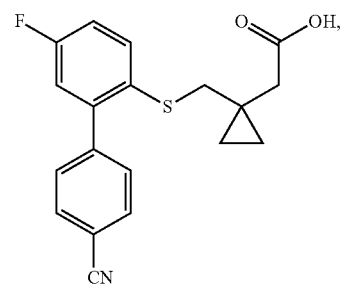 [SMILES: N#Cc1ccc(-c2cc(F)ccc2SCC2(CC(=O)O)CC2)cc1]

or a pharmaceutically acceptable salt thereof.

22. A method of reducing the blood uric acid level in a human, comprising administering to the human an effective amount of a compound selected from the group consisting of

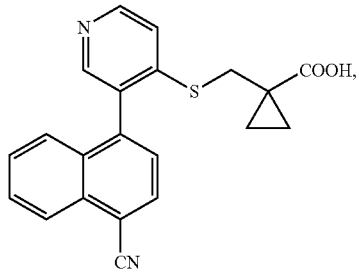

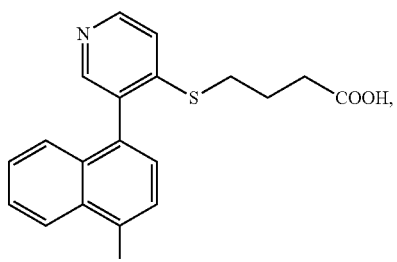

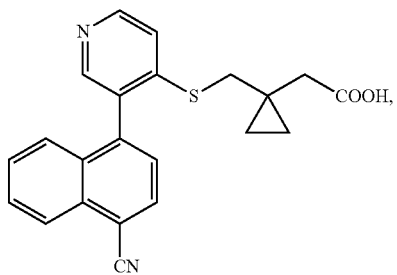

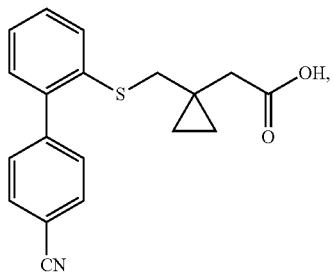

-continued
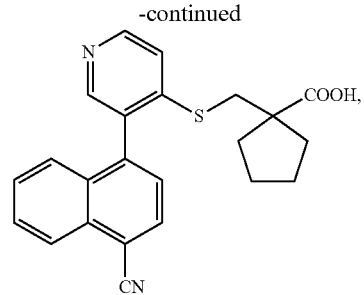
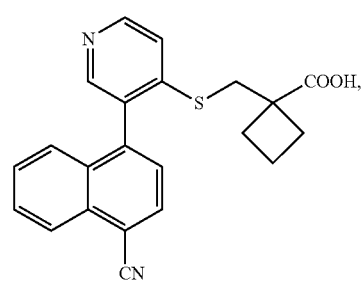
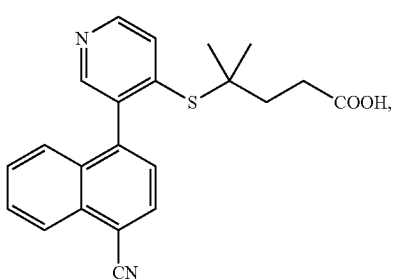
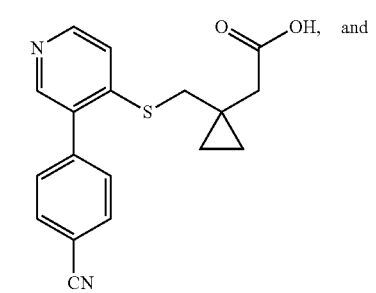
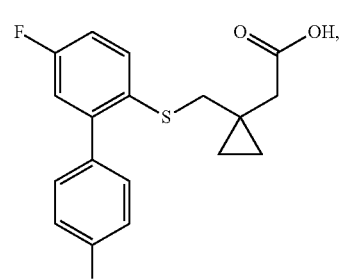
or a pharmaceutically acceptable salt thereof.
23. A method of treating hyperuricemia in a human, comprising administering to the human an effective amount of a compound selected from the group consisting of
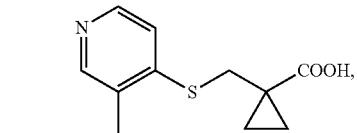
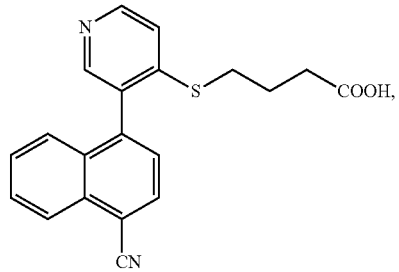
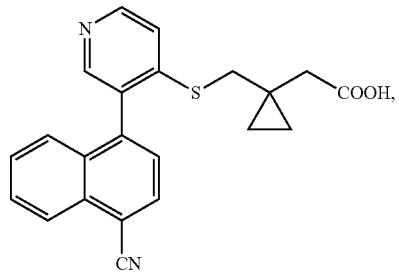
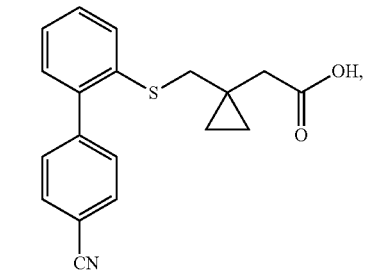
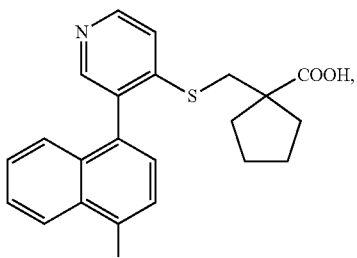
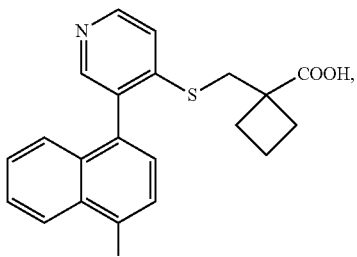

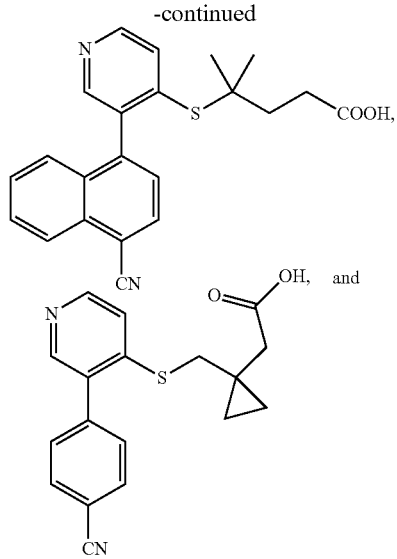
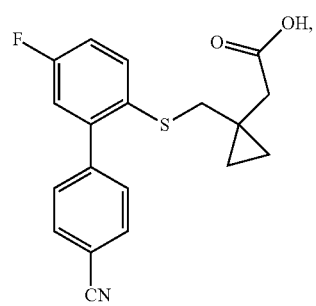
or a pharmaceutically acceptable salt thereof.
* * * * *